(12) United States Patent
Al-Jamal et al.

(10) Patent No.: US 8,741,579 B2
(45) Date of Patent: Jun. 3, 2014

(54) COMPOUNDS AND METHODS FOR THE MODULATION OF BETA-1 INTEGRIN FUNCTION TO MEDIATE TISSUE REPAIR

(75) Inventors: Rehab Al-Jamal, Edinburgh (GB); David Harrison, Edinburgh (GB)

(73) Assignees: Rehab Al-Jamal, Edinburgh (GB); Robert John Naylor, Bradford (GB)

(*) Notice: Subject to any disclaimer, the term of this patent is extended or adjusted under 35 U.S.C. 154(b) by 501 days.

(21) Appl. No.: 12/528,749

(22) PCT Filed: Feb. 26, 2008

(86) PCT No.: PCT/GB2008/050131
§ 371 (c)(1),
(2), (4) Date: Dec. 3, 2009

(87) PCT Pub. No.: WO2008/104808
PCT Pub. Date: Sep. 4, 2008

(65) Prior Publication Data
US 2010/0092472 A1   Apr. 15, 2010

(30) Foreign Application Priority Data
Feb. 26, 2007 (GB) .................................. 0703652.8

(51) Int. Cl.
*G01N 33/53* (2006.01)
(52) U.S. Cl.
USPC .......................................... 435/7.1; 435/7.21
(58) Field of Classification Search
None
See application file for complete search history.

(56) References Cited

U.S. PATENT DOCUMENTS

| | | | |
|---|---|---|---|
| 6,123,941 A | 9/2000 | Bissell et al. | |
| 6,177,475 B1 | 1/2001 | Tatrintsev et al. | |
| 6,251,419 B1 | 6/2001 | Graber et al. | |
| 2003/0109435 A1 | 6/2003 | Prenner et al. | |
| 2003/0186334 A1 | 10/2003 | Marcinkiewicz | |
| 2007/0048321 A1 | 3/2007 | Gotwals et al. | |

FOREIGN PATENT DOCUMENTS

| | | |
|---|---|---|
| WO | WO 97/25031 A1 | 1/1997 |
| WO | WO 00/15175 A2 | 3/2000 |
| WO | WO 01/54690 A1 | 8/2001 |
| WO | WO 03/063893 A2 | 1/2003 |
| WO | WO 2005/037313 A | 4/2005 |

OTHER PUBLICATIONS

Takagi et al. Global Conformational Rearrangements in Integrin Extracellular Domains in Outside-In and Inside-Out Signaling Cell, vol. 110, 599-611, Sep. 6, 2002.*
Shamri et al. Lymphocyte arrest requires instantaneous induction of an extended LFA-1 conformation mediated by endothelium-bound chemokines. Nature Immunology 6, 497-506 (2005).*
Weigel-Kelley et al. requirement of functional activation of beta1 integrin for viral entry alpha5beta1 integrin as a cellular coreceptor for human parvovirus B19 Blood. 2003;102:3927-3933.*
Non-Final Official Action for U.S. Appl. No. 10/576,264 (Jan. 13, 2011).
Ma et al., "Selective Inhibition of Matrix Metalloproteinase Isozymes and in Viro Protection against Emphysema by Substituted y-Keto Carboxylic Acids," J. Med. Chem. 2006, vol. 46, pp. 456-458 (Nov. 1, 2005).
Weigel-Kelley et al., "{alpha}5{beta}1 Integrin as a Cellular Coreceptor for Human Parvovirus B19: Requirement of Functional Activation of {beta}1 Integrin for Viral Entry," Blood, vol. 102, pp. 3927-3933 (Aug. 2003).
Chen et al., "The Angiogenic Factors Cyr61 and Connective Tissue Growth Factor Induce Adhesive Signaling in Primary Human Skin Fibroblasts," The Journal of Biological Chemistry, vol. 276, No. 13, pp. 10445-10452 (Mar. 2001).
Examination Report for UK Patent Application No. 0916943.4 (Oct. 25, 2010).
Japanese Examination Report for JP Patent Application No. 2006-534832 (partial translation) (Oct. 5, 2010).
Albequerque et al., "Lamellipodial Motility in Wounded Endothelial Cells Exposed to Physiologic Flow is Associated with Different Patterns of β1-Integrin and Vinculin Localization," Journal of Cellular Physiology, vol. 195, No. 1, pp. 50-60 (Apr. 2003).
DiPersio et al., "Mouse Keratinocytes Immortalized with large T Antigen Acquire α3β1 Integrin-dependent Secretion of MMP-9/gelatinase B," British Journal of Cell Science, vol. 113, No. 16, pp. 2909-2921 (Aug. 2000).
Ni et al., "Localizatin of a Novel Adhesion Blocking Epitope on the Human β1 Integrin Chain," vol. 5, No. 4, pp. 257-271 (Jun. 1998).
Kamiguti et al., "Inhibition of Collagen-induced Platelet Aggregation as the Result of Cleavage of α2β1-Integrin by the Snake Venom Metalloproteinase Jararhagin," Biochemistry Journal, vol. 320, No. 2, pp. 635-641 (Dec. 1996).
Zhang et al., "The α5β1 Integrin Supports Survival of Cells on Fibronectin and Up-regulates Bcl-2 Expression," Proc. National Academy of Science USA, vol. 92, No. 13, pp. 6161-6165 (Jun. 1995).
Rahilly et al., "The Specificity of Integrin-ligand Interactions in Cultured Human Renal Epithelium," Journal of Pathology, vol. 170, No. 3, pp. 297-303 (Jul. 1993).
Arroyo et al., "Regulation of the VLA Integrin-ligand Interactions Through the β1 Subunit," Journal of Cell Biology, vol. 117, No. 3, pp. 659-670 (May 1992).
Official Action for U.S. Appl. No. 10/576,274 (Jan. 28, 2010).
Final Official Action for U.S. Appl. No. 10/576,274 (Jul. 28, 2009).
Official Action for U.S. Appl. No. 10/576,274 (Dec. 3, 2008).
Restriction Requirements for U.S. Appl. No. 10/576,274 (Jul. 31, 2008).
Al-Jamal et al., "Beta1 Integrin in Tissue Remodeling and Repair: From Phenomena to Concepts," Pharmacology and Therapeutics, vol. 120, pp. 81-101 (2008).

(Continued)

*Primary Examiner* — Maher Haddad
(74) *Attorney, Agent, or Firm* — Jenkins, Wilson, Taylor & Hunt, P.A.

(57) ABSTRACT

The present invention provides methods and compositions which modulate beta 1 integrin activity by functioning as allosteric antagonists. In particular, the present invention provides methods for mediating tissue repair where insult or injury has occurred by antagonising the allosteric function of beta 1 integrin.

7 Claims, 28 Drawing Sheets

(56) References Cited

OTHER PUBLICATIONS

Wright et al., "α2β1 and αVβ1 Integrin Signaling Pathways Mediate Amyloid-β-Induced Neurotoxicity," Neurbiology of Again 28, vol. 28, Issue 2, pp. 226-237 (Feb. 2007).

Zweers et al., "Integrin α2β1 is Required for Regulation of Murine Wound Angiogenesis but is Dispensable for Reepithelialization," The Society for Investigative Dermatology, vol. 127, pp. 467-478 (Sep. 14, 2006).

International Search Report and Written Opinion of the International Searching Authority for International Application No. PCT/GB2004/004406 (Aug. 2, 2005).

Luo et al., "Allosteric β1 Integrin Antibodies That Stablizie the Low Affinity State by Preventing the Swing-out of the Hybrid Domain," The Journal of Biological Chemistry, vol. 279, No. 26, pp. 27466-27471 (Jun. 25, 2004).

Hassanieh et al., "Generation of a Monoclonal Antibody to a Cryptic Site Common to Both Integrin β1 as Well as Gelatinase MMP9," Hybridoma and Hybridomics, vol. 22, No. 5, pp. 285-292 (Oct. 2003).

Leu et al., "Identification of a Novel Integrin α6β1 Binding Site in the Angiogenic Inducer CCN1 (CYR61)," The Journal of Biological Chemistry, vol. 278, No. 36, pp. 33801-33808 (Sep. 5, 2003).

Lin et al., "CCN3 (NOV) is a Novel Angiogenic Regulator of the CCN Protein Family," The Journal of Biological Chemistry, vol. 278, No. 26, pp. 24200-24208 (Jun. 27, 2003).

Sun et al., "Temporal Response and Localization of Integrins β1 and β3 in the Heart After Myocardial infarction: Regulation by Cytokines," Circulation, vol. 107, No. 7, pp. 1045-1052 (Feb. 25, 2003).

Chemicon International, Catalog No. MAB 1965, 5 pages (Sep. 23, 2002).

Wu et al., "β1-Integrin-Mediated Glioma Cell Adhesion and Free Radical-Induced Apoptosis are Regulated by Binding to a C-terminal Domain of PG-M/Versican," Journal of Biological Chemistry, vol. 277, No. 14, pp. 12294-12301 (Apr. 5, 2002).

Binda, "Bypassing Immunization in an Attempt to Develop β1 Specific Monoclonal Human Antibodies From Semi-Synthetic Repertoires," Thesis submitted to the University of Manitoba (Jun. 1999).

Herard et al., "Fibronectin and its α5β1-Integrin Receptor are Involved in the Wound-Repair Process of Airway Epithelium," The American Physiological Society, vol. 271, pp. L726-L733 (Nov. 1996).

Miyake et al., "A Calcium- or Manganese-Dependent Epitope on the Integrin β1 Chain Recognized by a Unique mAB," International Immunology, vol. 6, No. 8, pp. 1221-1226 (Aug. 1994).

Owens et al., "The Genetic Engineering of Monoclonal Antibodies," Journal of Immunological Methods, vol. 168, No. 2, pp. 149-165 (Feb. 20, 1994).

Clark, "Fibronectin Matrix Deposition and Fibronectin Receptor Expression in Healing and Normal Skin," The Journal for Investigative Dermatology, vol. 94, No. 6, pp. 128S-134S (Jun. 1990).

Search Report under Section 18(3) for Application No. GB0916943.4 (May 17, 2010).

Final Official Action for U.S. Appl. No. 10/576,274 (May 28, 2010).

Corry et al., "Overlapping and Independent Contributions of MMP2 and MMP9 to Lung Allergic Inflammatory Cell Egression Through Decreased CC Chemokines," The FASEB Journal, vol. 18, pp. 995-997 (2004).

Fischer et al., "Lymphocyte-Endothelial interactions in Inflamed Synovia: Involvement of Serval Adhesion Molecules and Integrin Epitopes," Scandinavian Journal of Immunology., vol. 38, Issue 2, pp. 158-166 (Aug. 1993).

International Search Report for International Application No. PCT/GB2008/050131 (Oct. 16, 2008).

Piraino et al., "Prolonged reversal of chronic EAE using an inhibitor of alpha4 integrin," Society for Neuroscience Abstracts, vol. 26, No. 1-2, pgs. Abstract (2000).

Yamada et al., "Mechanisms regulating expression of cell-cell junction proteins in the heart," Circulation, vol. 110, No. 17, Suppl. S, p. 636 (Oct. 2004).

Arroyo et al., "Expression and Functional Significance of an Activation-Dependent Epitope of the Beta-1 Integrins in Chronic Inflammatory Diseases," European Journal of Immunology, vol. 25, No. 6, pp. 1720-1728 (Jan. 1, 1995).

Grose et al., "A crucial role of beta1 integrins for keratinocyte migration in vitro and during cutaneous wound reapir," Development, Company of Biologists, vol. 129, No. 9, pp. 2303-2315 (May 1, 2002).

Wilkins et al., "Control of beta-1 integrin function: Localization of stimulatory epitopes," Journal of Biological Chemistry, American Society of Biolchemical Biologists, vol. 271, No. 6, pp. 3046-3051 (Feb. 9, 1996).

Brakebusch et al., "Genetic analysis of beta1 integrin function: Confirmed, new and revised roles for a crucial family of cell adhesion molecules," Journal of Cell Science, vol. 110, No. 23, pp. 2895-2904 (Dec. 1, 1997).

* cited by examiner

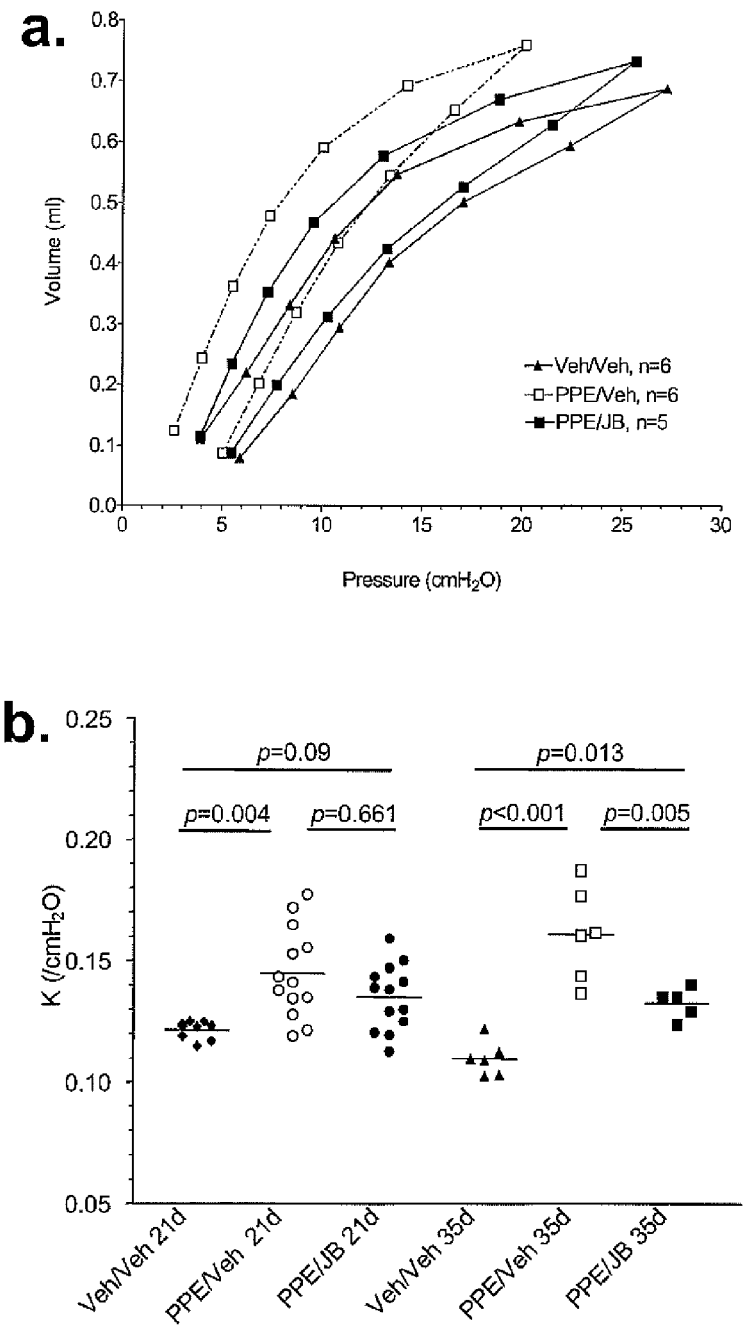
Figure 1 (a) and (b)

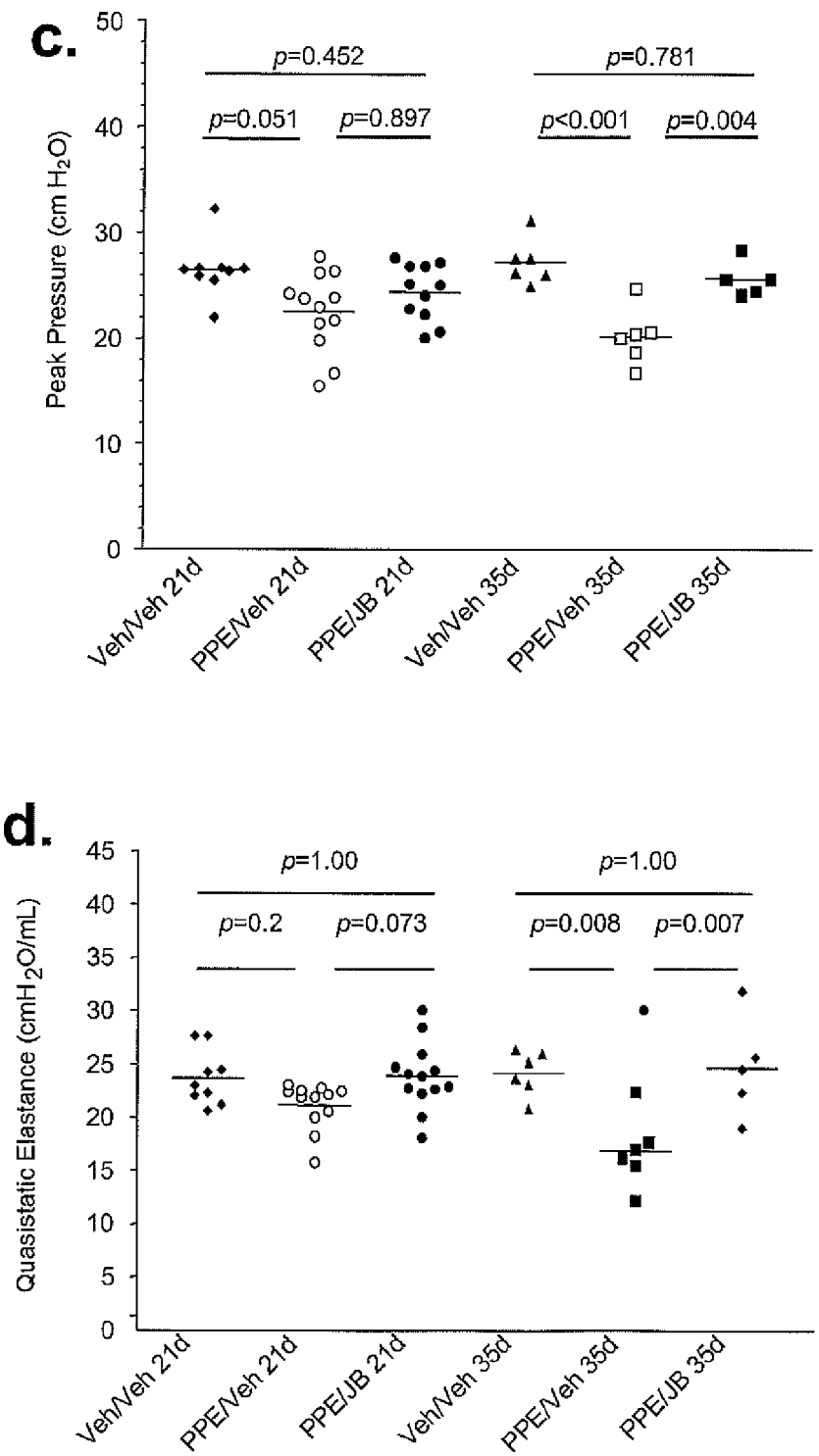
Figure 1 (c) and (d)

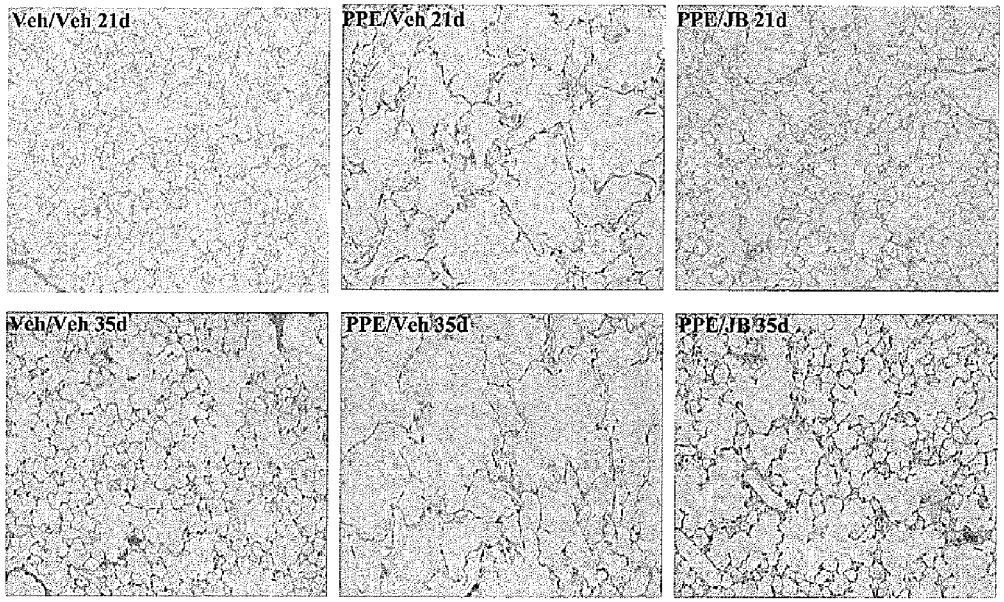
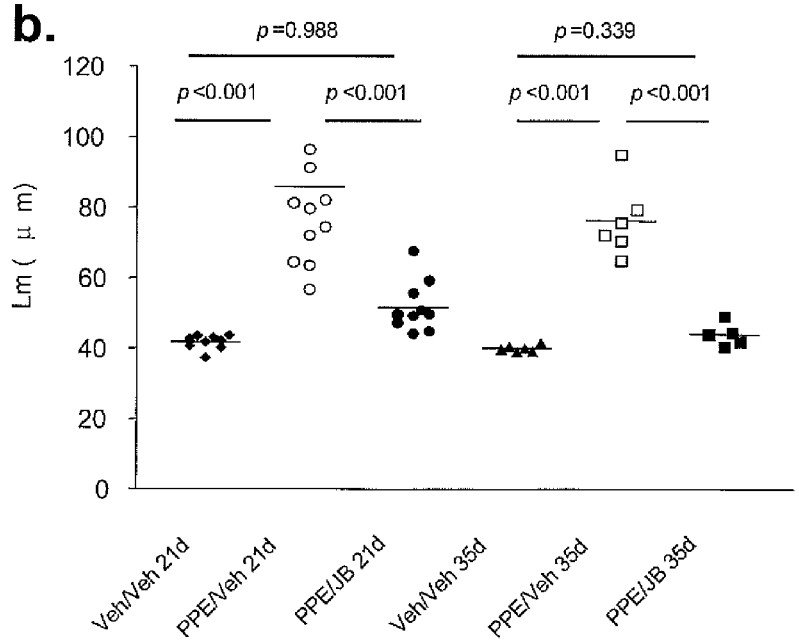
Figure 2 (a) and (b)

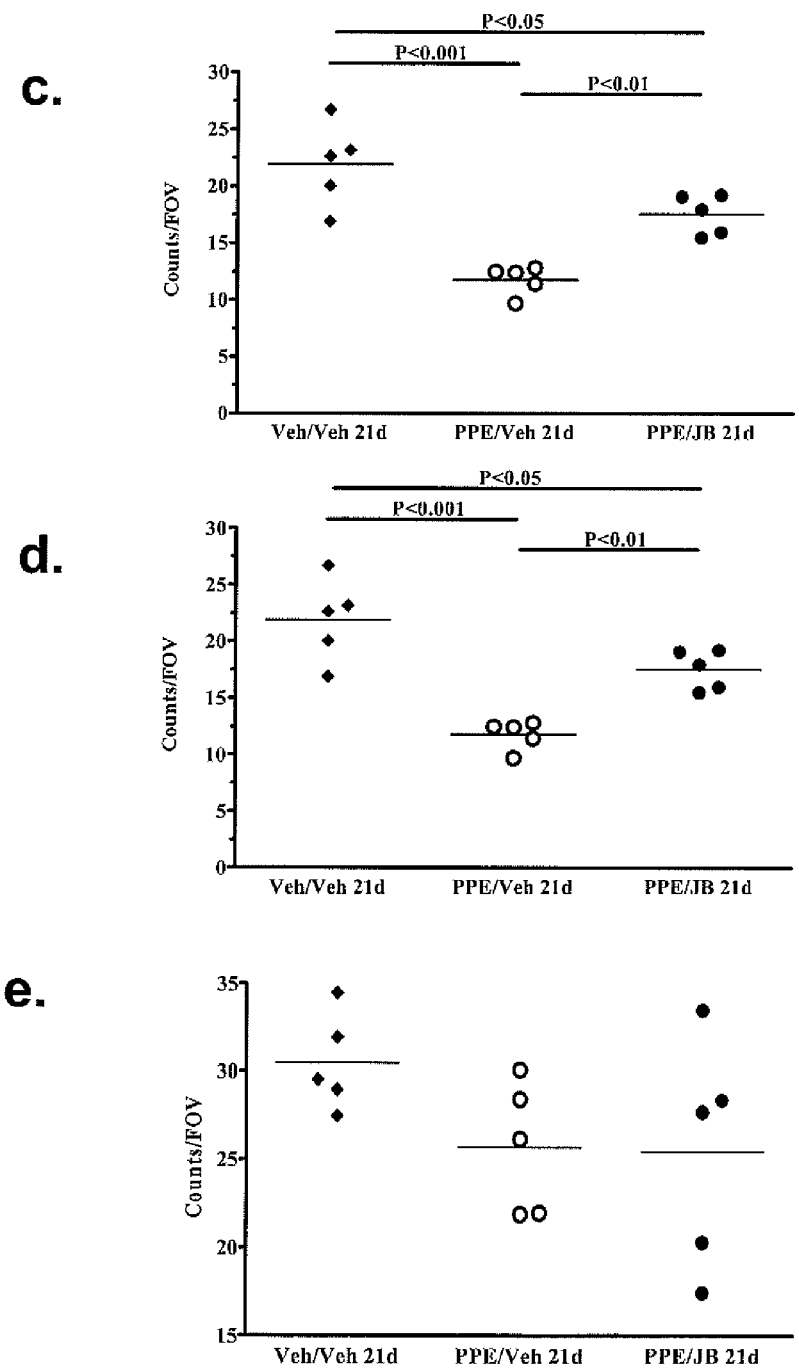
Figure 2 (c), (d) and (e)

b.
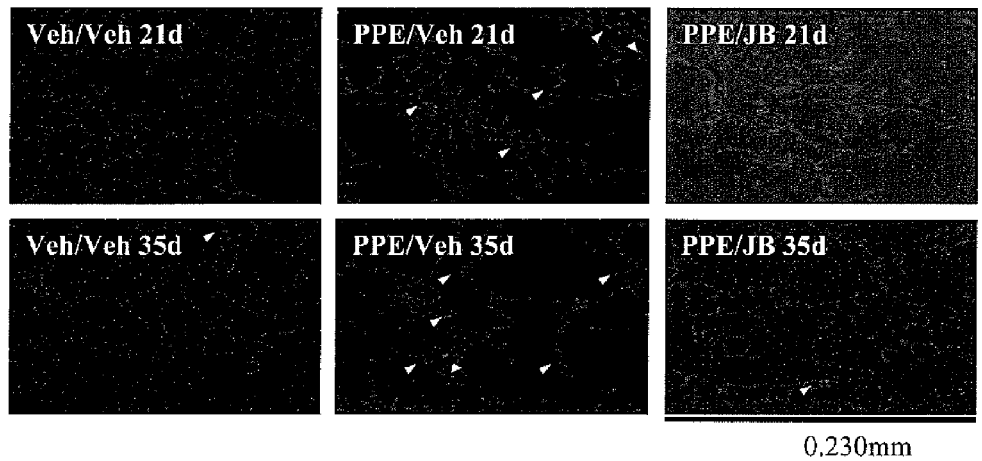
c.
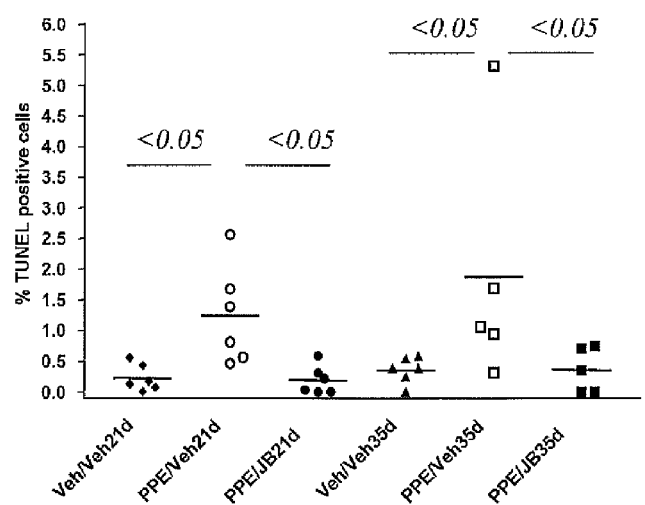
Figure 3 (b) and (c)

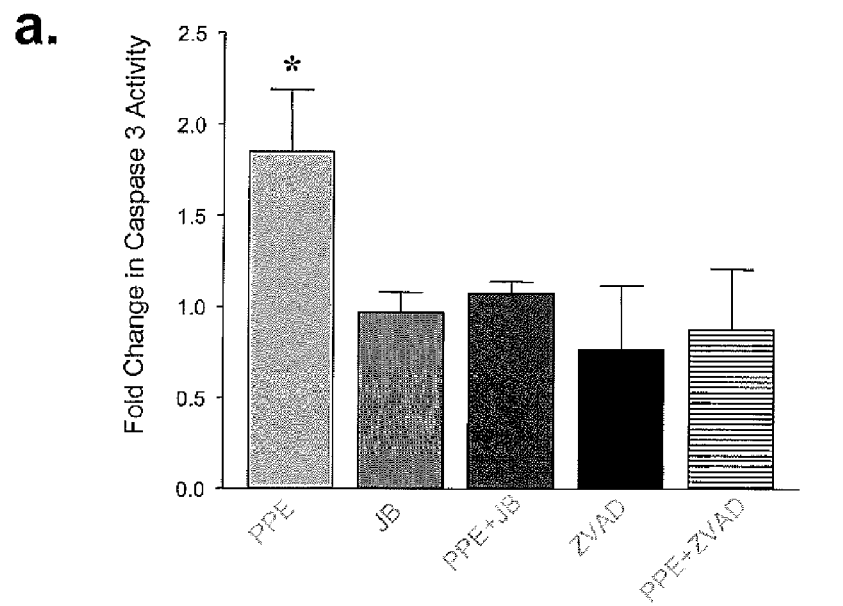
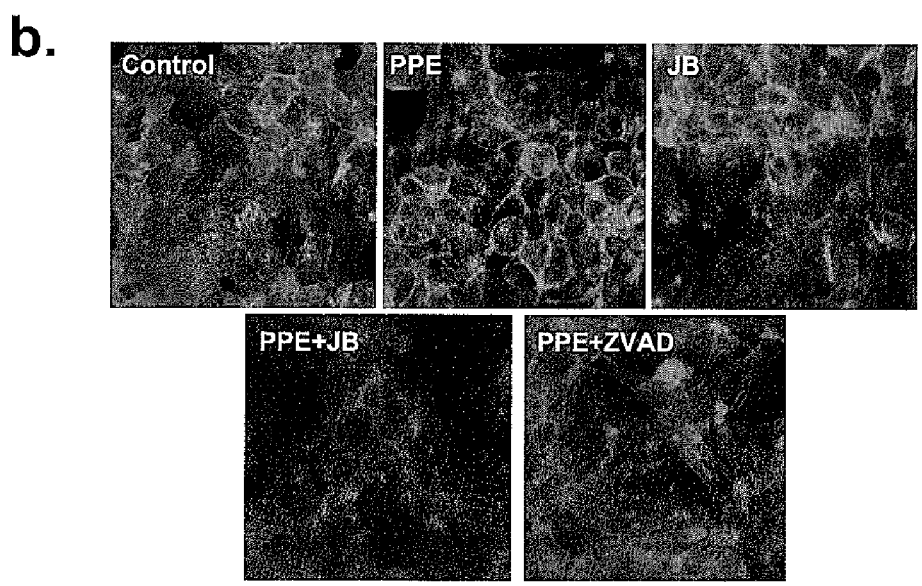
Figure 4 (a) and (b)

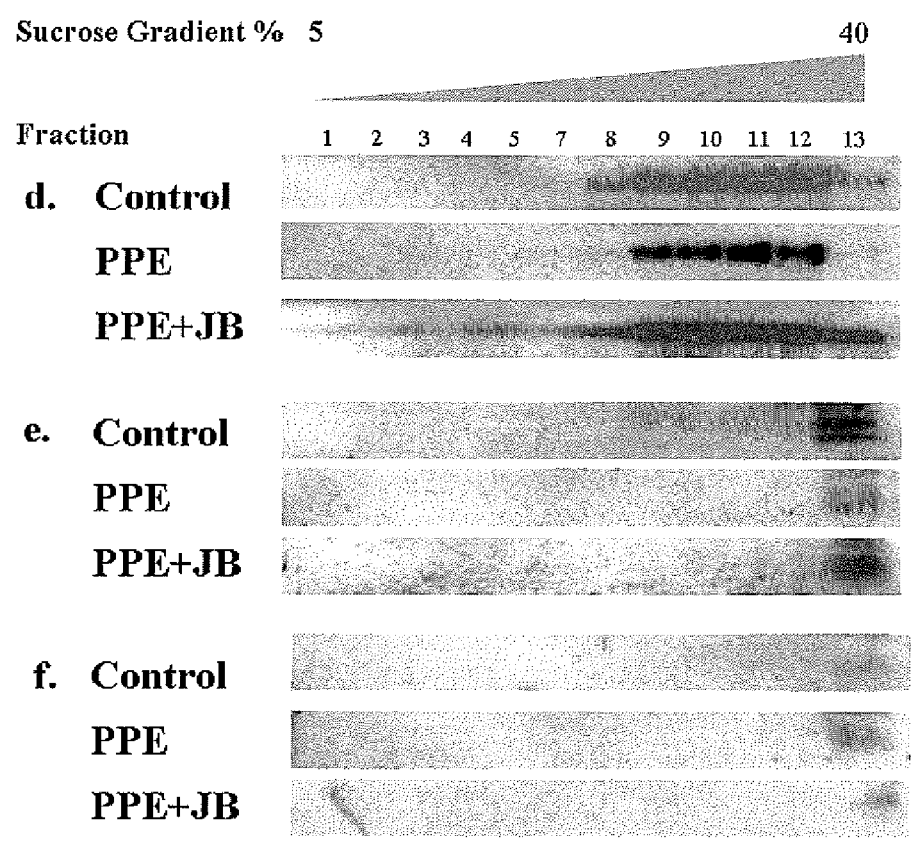
Figure 4 (d), (e), (f)

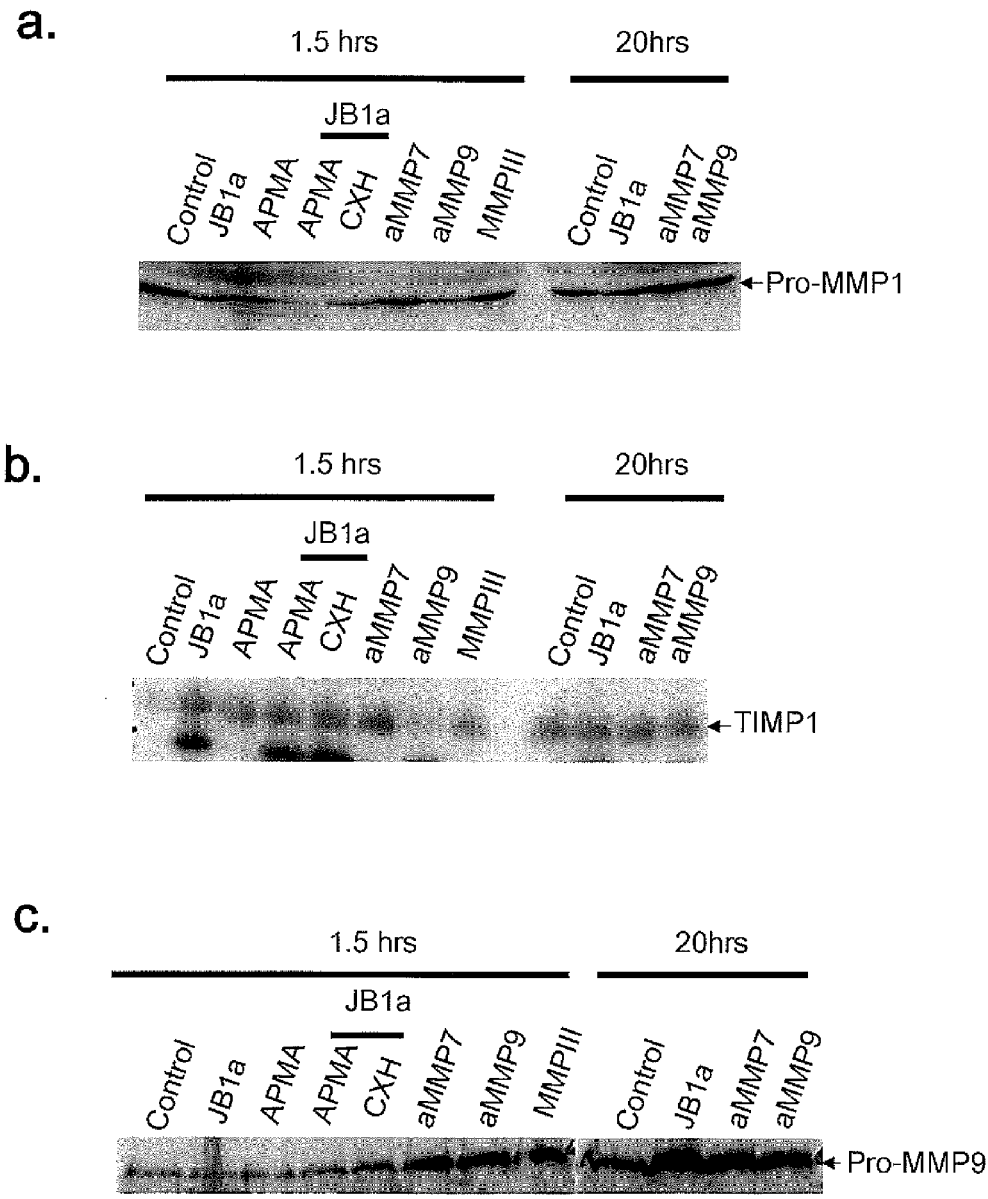
Figure 5 (a), (b) and (c)

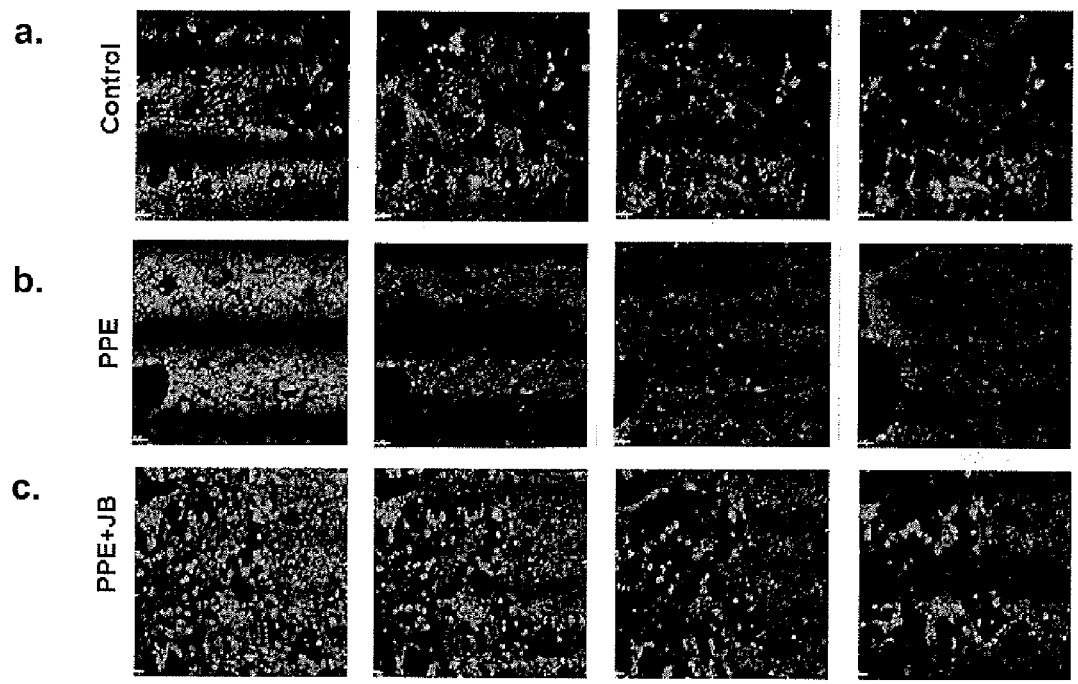
Figure 7 (a), (b) and (c)

Iso-Surface 3D reconstruction
a. Control 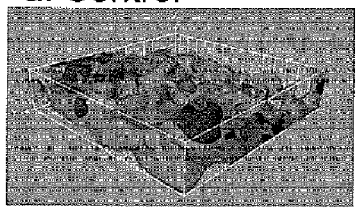 b. Elastase  c. Elastase+JB1a 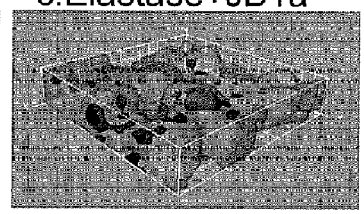
Wireframe Mesh 3D reconstruction
d. Control 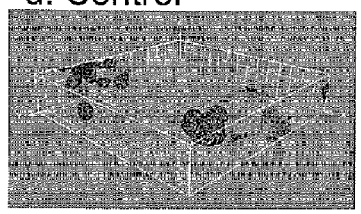 e. Elastase  f. Elastase+JB1a 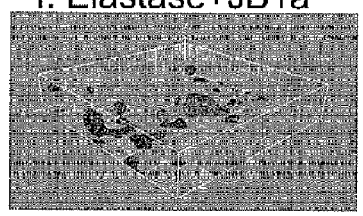
Figure 8 (a), (b), (c), (d), (e) and (f)

a. Vehicle/Vehicle b. PPE/Vehicle
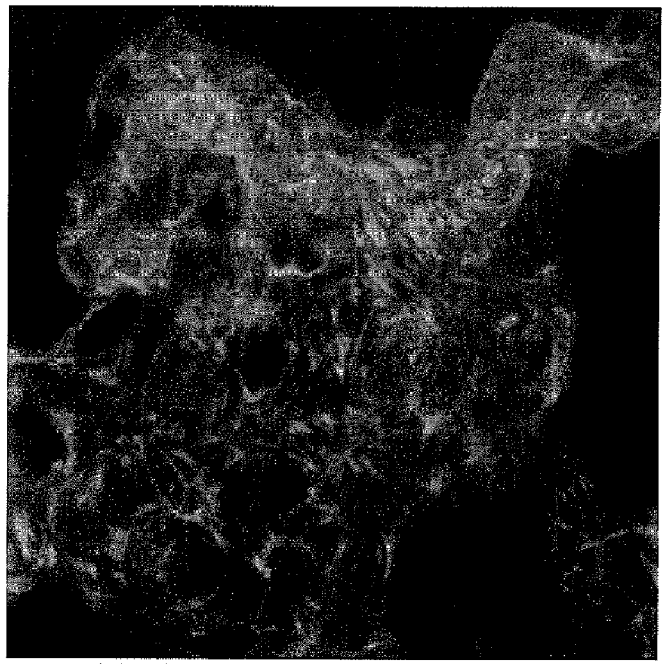
c.
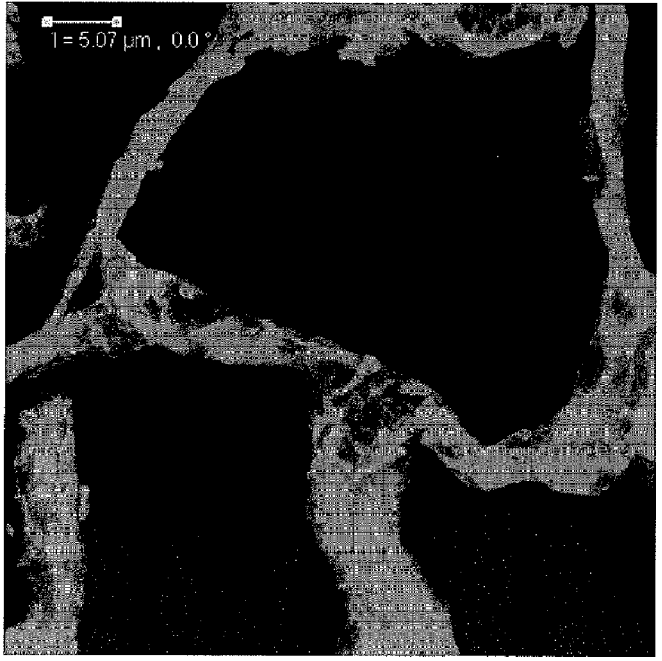
Figure 9 (b) and (c)

PPE/JB1a
d.
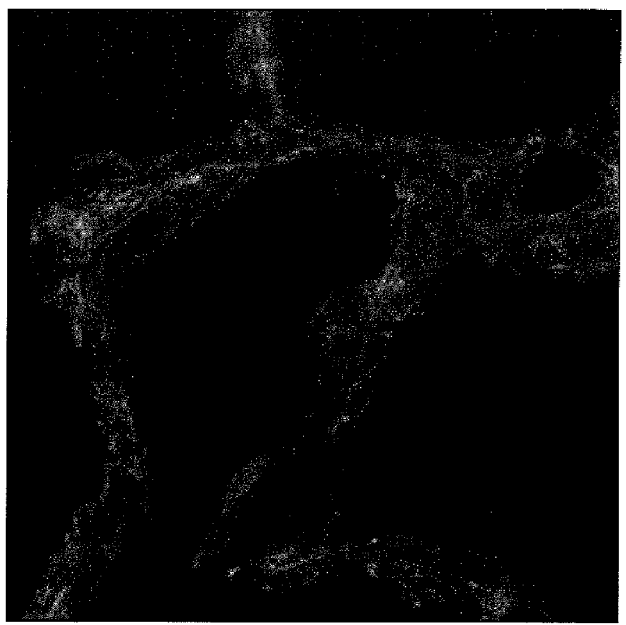
e.
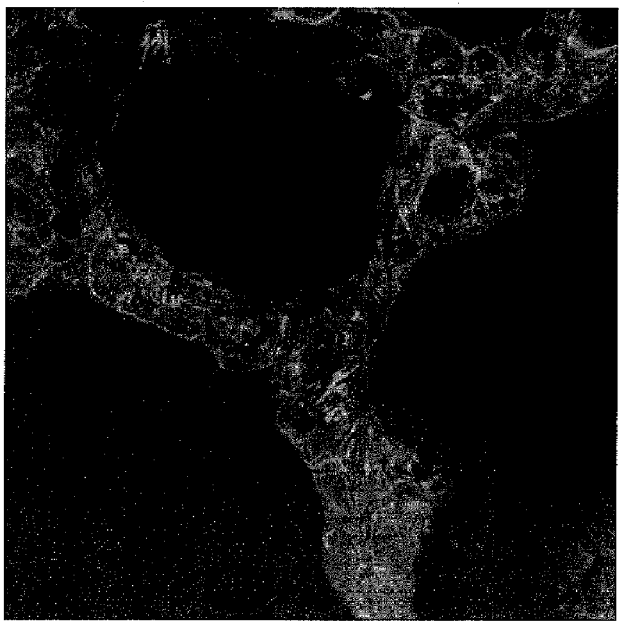
Figure 9(d) and (e)

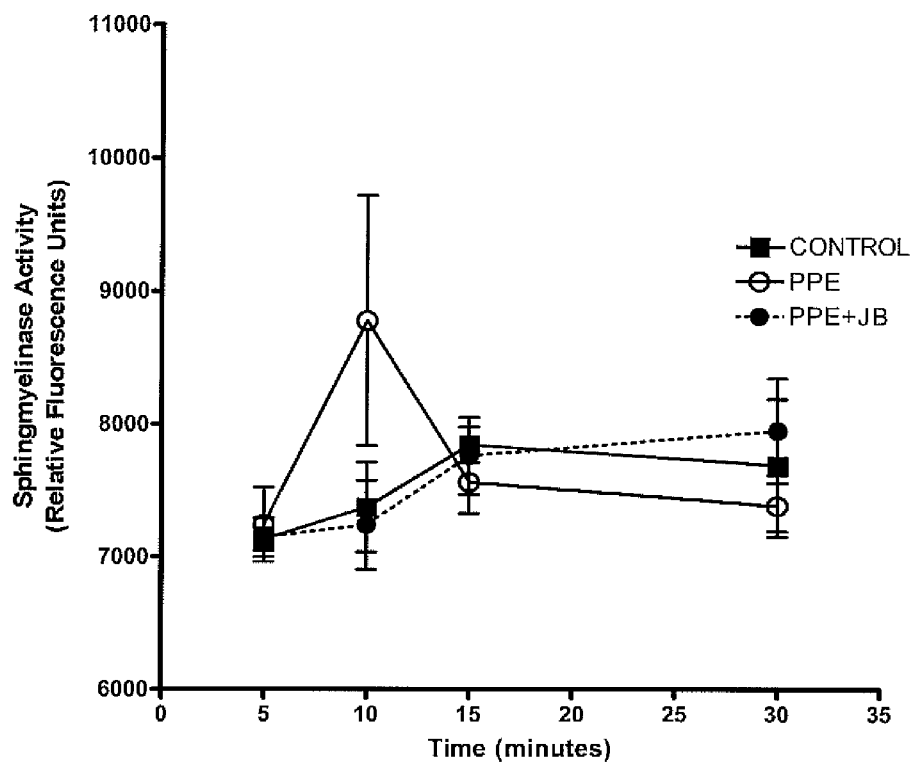
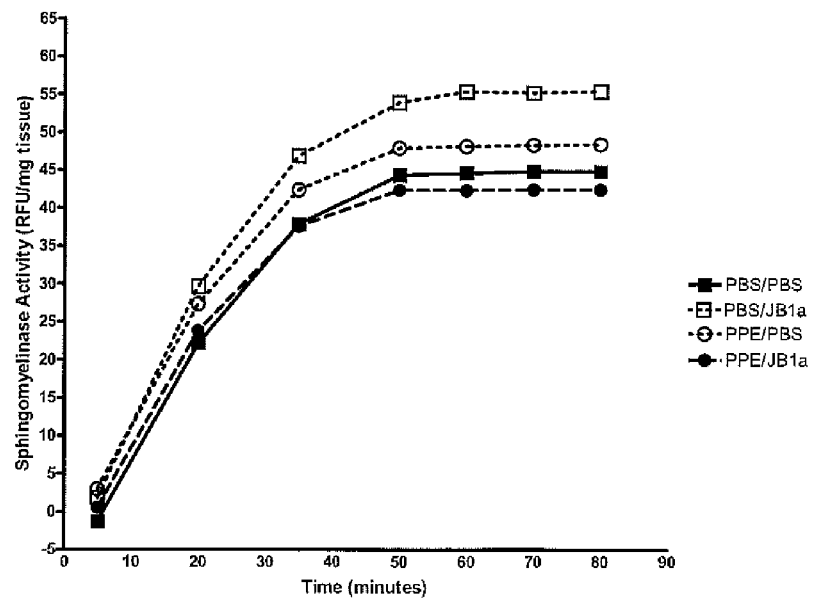
Figure 10 (a) and (b)

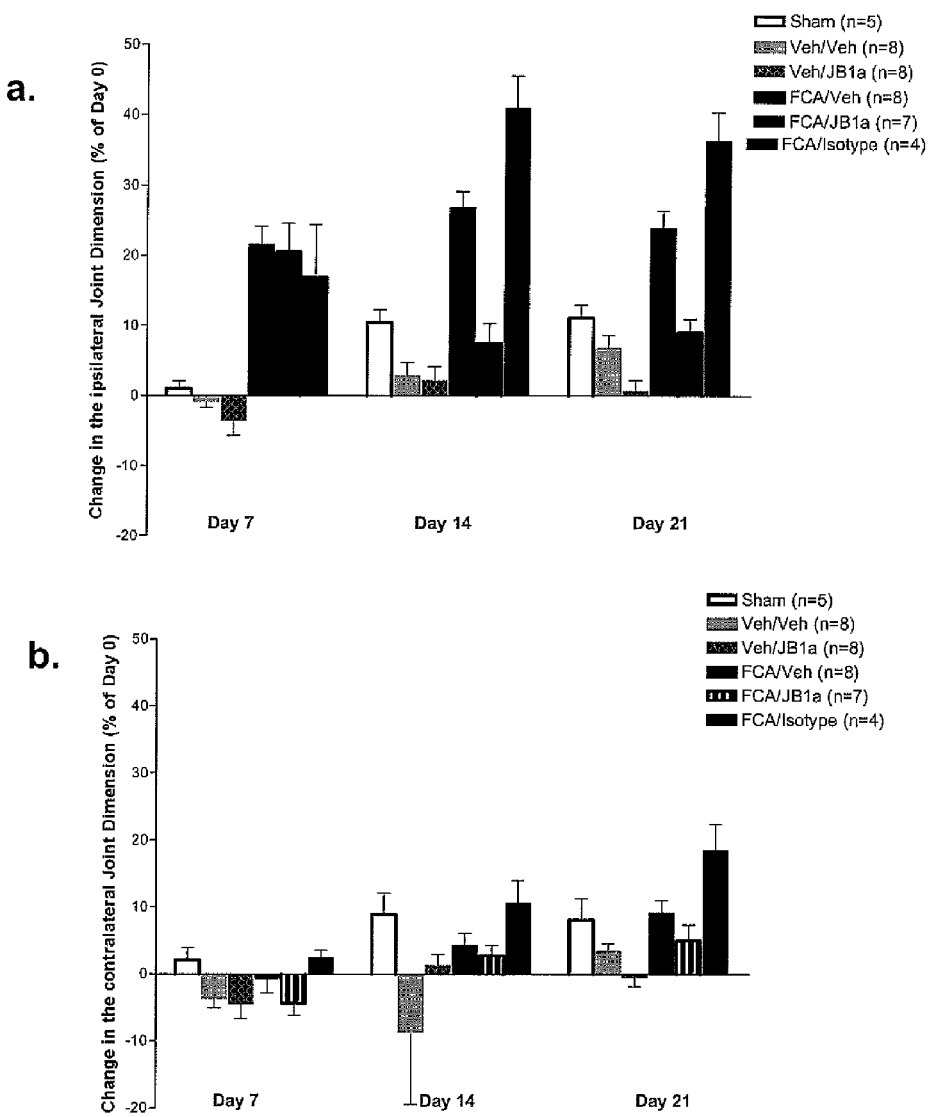
Figure 13 (a), (b)

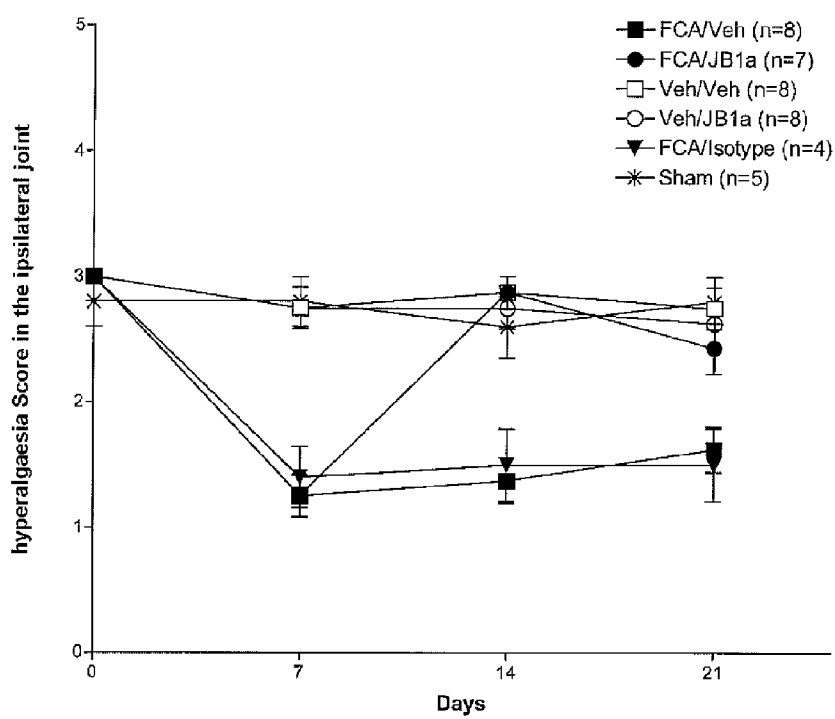
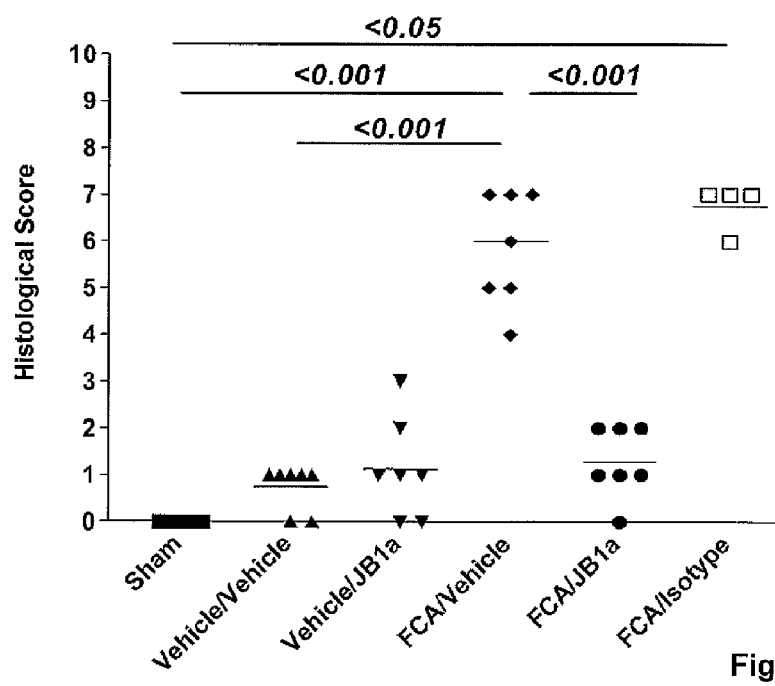
Figure 13 (c), (d)

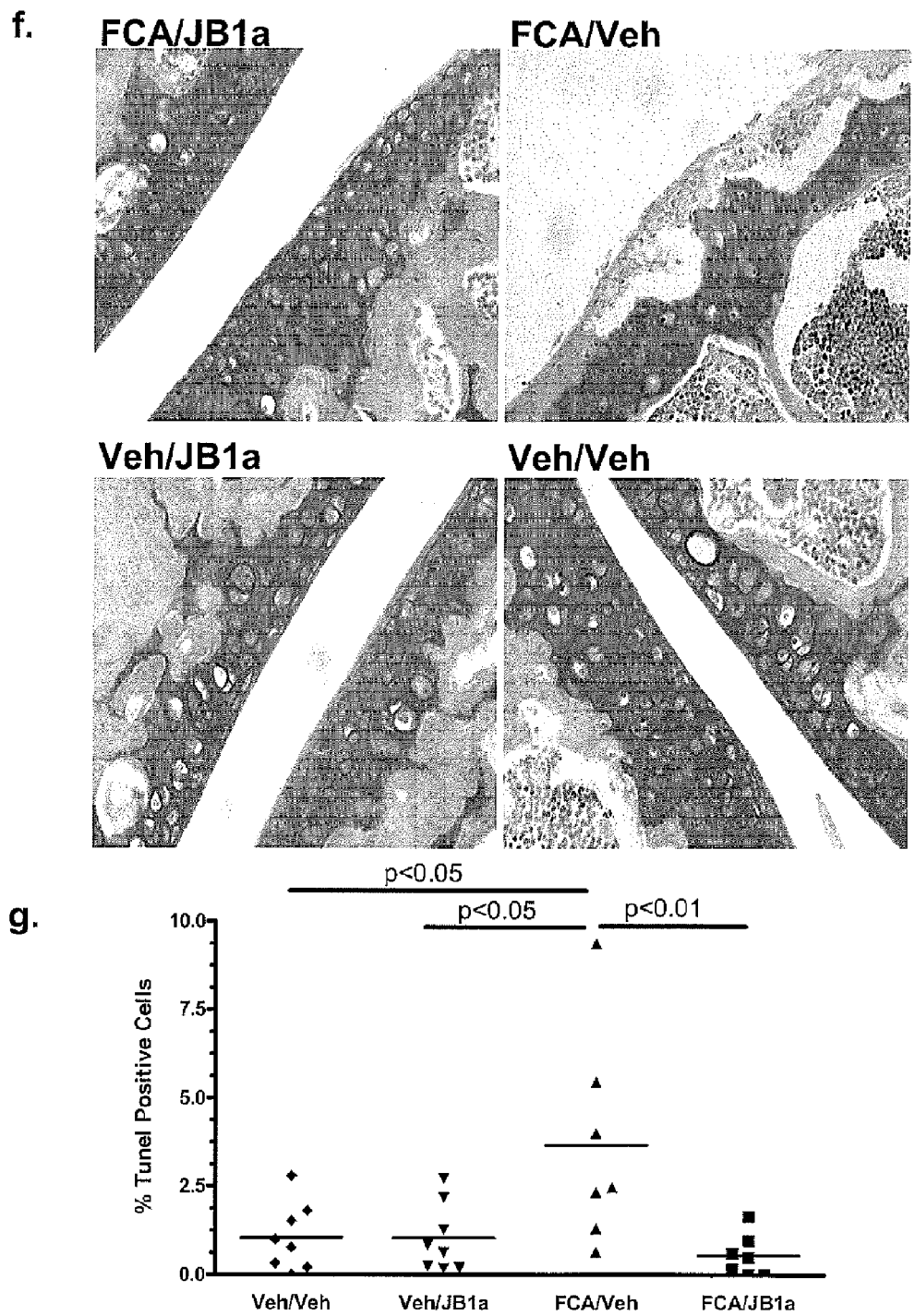
Figure 13 (f), (g)

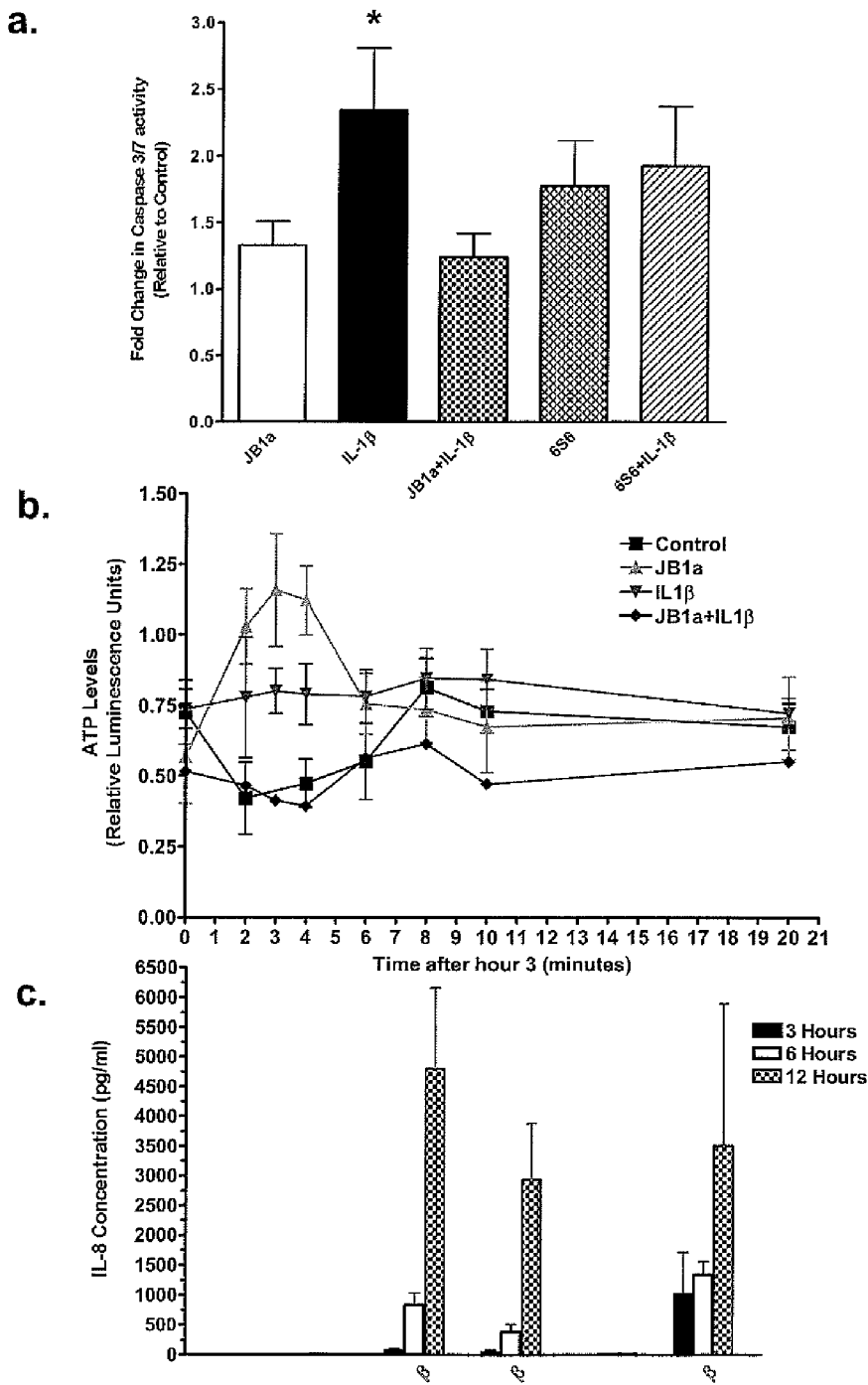
Figure 14 (a),(b) and c

6hrs          8hrs

6hrs

```
  1  mnlqpifwig lissvccvfa qtdenrclka nakscgeciq agpncgwctn stflqegmpt
 61  sarcddlcal kkkgcppddi cnprgskdik knknvtnrsk gtaeklkped ihqiqpqqlv
121  lrlrsgcpqt ftlkfkracd ypidlyylmd lsysmkddle nvkslgtdlm nemrritsdf
181  rigfgsfvek tvmpyisttp aklrnpctse qncttpfsyk nvlsltnkge vfnclvgkqr
241  isgnldspeg gfdaimqvav cgsligwrnv trllvfstda gfhfagdgkl ggivlpndgq
301  chlennmytm shyydypsia hlvqklsenn iqtifavtee fqpvykelkn lipksavgtl
361  sanssnviql iidaynslss evilengkls egvtisyksy ckngvngtge ngrkcsnisi
421  gdevqfeisi tsnkcpkkds dsfkirplgf teevevilqy icececqseg ipespkcheg
481  ngtfecgacr cnegrvgrhc ecstdevnse dmdaycrken sseicsnnge cvcgqcvcrk
541  rdntneiysg kfcecdnfnc drsnglicgg ngvckcrvce cnpnytgsac dcsldtstce
601  asngqicngr gicecgvckc tdpkfqgqtc emcqtclgvc aehkecvqcr afnkgekkdt
661  ctqecsyfni tkvesrdklp qpvqpdpvsh ckekdvddcw fyftysvngn nevmvhvven
721  pecptgpdii pivagvvagi vliglallli wkllmiihdr refakfekek mnakwdtgen
781  piyksavttv vnpkyegk
```

Figure 16

COMPOUNDS AND METHODS FOR THE MODULATION OF BETA-1 INTEGRIN FUNCTION TO MEDIATE TISSUE REPAIR

FIELD OF THE INVENTION

The present invention provides compounds and methods for the selective modulation of the ligand binding function of an integrin, in particular beta1 integrin. More specifically, there is provided a method for mediating tissue repair following insult and injury by allosterically modulating beta1 integrin. The invention further provides compounds which act as allosteric antagonists of beta 1 integrin and which modulate beta1 integrin function in order to mediate tissue repair. The invention further extends to methods for the treatment of tissue damage associated with disease conditions such as chronic obstructive pulmonary disease, arthritis, and neurodegenerative conditions.

BACKGROUND TO THE INVENTION

Integrins constitute a family of widespread heterodimeric cell surface adhesion receptors comprised of non-covalently associated alpha ($\alpha$) and beta ($\beta$) subunits. To date, 18 different alpha subunits and 8 different beta subunits have been described in vertebrates, these forming 24 distinct heterodimers. Of these heterodimers, 12 contain the beta1 ($\beta$1, beta 1, beta-1, CD29) subunit.

To date, the precise structure of beta 1 integrin has not been identified. However, a prediction of the X-ray crystalline structure of beta 1 has been produced, and is shown in FIG. 17. The alpha and beta subunit of all integrins fold forming an extracellular headpiece which is connected to the membrane by a structure which can be likened to "2 supporting legs", followed by a short transmembrane domain and cytoplasmic tail. The headpiece of the integrin heterodimer is composed of a beta propeller domain of the alpha subunit which closely interacts with the A domain of the beta subunit (the A domain also being known as the I-like domain of the beta subunit).

The affinity state of an integrin is regulated by the conformation of the headpiece. Rearrangement of the headpiece can be initiated by intrinsic ligands and by the binding of specific adaptors to the cytoplasmic domain.

The activation of beta 1 integrin is regulated in a cell-type dependent manner, and plays an important role in modulating cell functions. The avidity of an integrin is increased by the transition to an active conformational state. The specific conformational state of an integrin receptor can have a fundamental effect on integrin function. As such, in many instances, integrin conformation is more important than integrin expression levels when considering the physiological and pathological remodelling of tissue.

Integrin antagonists fall into three classes; direct inhibitors of ligand binding to the I domain of the alpha chain, allosteric inhibitors of the I domain of the alpha chain and allosteric antagonists of alpha chain/beta I-like domains (also known as the A domain).

Functional modification of beta1 integrin using antibodies is known. For example, International Patent Application Number WO 05/037313 discloses the use of compounds which modulate beta 1 integrin in order to mediate an increase in anabolism of the extracellular matrix. Such compounds are identified as being of use in tissue regeneration.

Further approaches to the modulation of beta 1 integrin functional activity focus on the modulation of beta1 integrin by means of activation or blocking of adhesion to a substrate under a defined set of conditions. Modulation of beta1 integrin in such a way has a number of limitations. Firstly, modulation is based on the understanding that integrins can exist in inactive, active and active and occupied states. Secondly, functional modulation was often achieved via different domains of the integrin. This may entail different downstream intracellular signalling, and therefore even if the effect on adhesion is similar, the functional end outcome can be different as each region appears to possess a different function. Further, beta1 integrin is known to exist in four different splice variants, with the resulting differences in the cytoplasmic domain implicating different downstream signalling.

Following extensive experimentation, the inventors have now surprisingly identified that compounds which interact with beta 1 integrin and function as antagonists of allosteric modulation have utility in tissue repair. The inventors have identified that such allosteric antagonists can function to promote tissue repair, this being characterised by the physical and/or mechanical restoration of damaged or diseased tissues through the growth of new cellular structures. Further, the inventors have further recognised that direct allosteric modulation of beta 1 integrin with a compound which functions as an allosteric antagonist can result in the reversal of functional and structural changes associated with tissue repair.

SUMMARY OF THE INVENTION

According to the first aspect of the present invention there is provided a method of modulating one or more of the biological activities of beta 1 integrin in a beta 1 integrin expressing cell or tissue in order to mediate cellular or tissue repair, comprising:

contacting the cell or tissue with an allosteric antagonist of beta 1 integrin, in an amount sufficient to reduce one or more biological activities of beta 1 integrin in the cell or tissue which causes in tissue damage or cell death.

In certain embodiments, the reduction of one or more of the biological activities of beta 1 integrin may relate to one of more of; inhibiting cell death, modulating cellular differentiation, modulating cellular mechanisms, such as inhibiting caspase activation, F-actin aggregate formation, causing fluctuations in cellular ATP levels, and increasing cellular impedance. Typically the reduction of said one or more biological activities of beta 1 integrin relates to the conformation of the beta 1 integrin being modulated such that it assumes an intermediate affinity state.

In certain embodiments of this aspect of the invention, the allosteric modulator is an allosteric antagonist which, when bound to an epitope present on beta 1 integrin, and in particular, the extracellular domain of beta 1 integrin, causes a conformational change of beta 1 integrin such that the extracellular domain of beta 1 integrin assumes a conformation defined as the intermediate affinity state. In this "intermediate conformatory state", the extracellular domain of beta 1 integrin assumes an extended conformation, however, the headpiece assumes a closed conformation.

The "intermediate affinity state" differs from the conformation of an inactive integrin where the extracellular domain assumes a low affinity bent confirmation, wherein the integrin is conformationally bent, and the headpiece is spaced approximately 5 nm from the cell membrane upon which the integrin is expressed.

The intermediate affinity state also differs from the conformation of an activated beta 1 integrin molecule wherein the integrin assumes a high affinity extended form which has an open headpiece configuration.

The change in integrin conformation is mediated by a conformational change in the extracellular domain of beta 1 integrin which is mediated by the opening or closing of the hinge angle between the A domain and the hybrid domain of beta 1 integrin. The opening of this hinge is indicative of a conformational switch to a high binding affinity. Inactive beta 1 integrin has bent conformation, wherein the headpiece is spaced approximately 5 nm from the cell membrane upon which the integrin is expressed. nm. In the activated, extended conformation, the headpiece projects from the membrane at a distance of between 20 to 25 nm. Accordingly, when in the intermediate affinity state conformation, where the extracellular domain of the integrin is extended, but the headpiece is in a closed conformation, the headpiece can be between about 6 nm to about 19 nm from the cell membrane.

The inventors have identified that when beta 1 integrin is bound by a ligand, the integrin assumes a high affinity extended conformational form. However, tissue damage and injury occurs when beta 1 integrin is in this form. The inventors have therefore surprisingly identified that modulatory compounds which alter the allostery of the beta 1 integrin, and which in particular act as allosteric antagonists to prevent the integrin assuming an active, extended form, and which instead cause the beta 1 integrin to assume a conformation associated with the integrin being in a intermediate affinity state, can reverse functional and structural effects which result in tissue injury. In particular, the functional and structural reversal of tissue injury which are observed by the inventors following allosteric antagonism of beta 1 integrin mediate tissue repair, this being defined as the physical or mechanical restoration of damaged or diseased tissues by growth of healthy new cells.

Accordingly, the provision of compounds which bind to beta 1 integrin at a site distinct from the ligand binding site, and which mediate an allosteric modulation of beta 1 integrin such that it assume the intermediate affinity conformatory state, has utility in methods for tissue repair, wound healing and tissue regeneration.

In particular, the inventors have identified that when beta 1 integrin is in the activated, extended conformation, which, for example, results when beta 1 integrin is bound by a ligand, tissue damage and injury can occur. Accordingly, the present inventors provided herewith methods and compounds which allosterically modulate beta 1 integrin such that it reverts to the intermediate affinity conformation, a conformatory state which has been identified by the inventors as mediating tissue repair.

The inventors have further identified that binding of beta 1 integrin by divalent cations such as, for example, calcium, manganese and magnesium, can result in beta 1 integrin assuming high affinity extended conformation. The inventors have identified that such divalent cations bind to the extracellular domain of beta 1 integrin at sites termed MIDAS (metal ion dependent adhesion sites), and ADMIDAS (adjacent to metal ion dependent adhesion sites).

In particular, the inventors have identified potential MIDAS sites as being present in the human beta 1 integrin amino acid sequence a residue 150 (aspartic acid), 152 (serine), 154 (serine), 249 (glutamic acid), 279 (aspartic acid). Further, ADMIDAS sites are predicted to be present at residues 157 (aspartic acid), 158 (aspartic acid), and 362 (alanine) of the amino acid sequence of human beta 1 integrin.

The inventors have identified that the binding of divalent cations to these MIDAS and ADMIDAS sites result in a conformational activation of the beta 1 integrin into an extended, high affinity conformation. In order to prevent the binding of such divalent cations to beta 1 integrin, the inventors have identified that binding beta 1 integrin with an allosteric antagonist which further prevents divalent cation binding to the MIDAS and ADMIDAS sites can have utility in the methods of the present invention, as the integrin will not assume the activated, extended conformation.

As defined herein, the term "allosteric modulator", "allosteric antagonist" or "allosteric modulator compound" relates to a compound which can allosterically modulate beta1 integrin in order to cause the beta 1 integrin to assume an intermediate affinity conformation, wherein the extracellular domain and headpiece of beta 1 integrin is neither fully bent, nor fully extended. Allosteric modulation refers to a control mechanism which alters protein behaviour wherein the binding of an allosteric modulator occurs at a binding site distinct from the active site, this resulting in a conformational change which influences protein function.

As defined herein, the term "modulates" relates to a change in the conformation or functional activity of beta 1 integrin.

The allosteric antagonist of the invention mediates a conformational change to beta 1 integrin such that it assumes a conformation defined as the intermediate affinity state. As defined herein, the term "intermediate affinity state" describes the conformation of the extracellular domain of beta1 integrin when under normal homeostatic conditions. When in this state, beta1 integrin is in an intermediate affinity binding state.

The term "normal homeostatic conditions" as used herein in relation to the conformational arrangement of beta1 integrin, relates to the structural conformation of the extracellular domain assumed by beta1 integrin which is in a conformational equilibrium between the accepted high and low affinity binding conformational states which beta1 integrin can assume. In the intermediate state, beta1 integrin is not in a completely inactive state, however "swing" out of the hybrid domain, a process required for beta1 integrin to assume a high affinity conformation, is prevented. Further, the intermediate affinity state can be further characterised in that it maintains extracellular binding.

Without wishing to be bound by theory, the inventors predict that the selective allosteric modulation of beta1 integrin such that the extracellular domain assumes an intermediate affinity binding conformation can result in a reduction in caspase activation and cell death, and thus can confer significant associated benefits in terms of tissue repair and regeneration.

This intermediate affinity conformation state is equivalent to the conformation assumed by the integrin when it is under normal homeostatic conditions. Selective allosteric modulation of the beta1 integrin, in accordance with the present invention, can induce the reversal of structural and functional changes resulting from cellular insult and injury. Such changes are important in preventing ECM degeneration and in allowing tissue repair and regeneration. The inventors have identified that complete inhibition or blocking of beta1 integrin results in cell death as the cell becomes detached from the ECM. The modulation effected by the methodology and compositions of the present invention prevents detachment of a cell from the ECM, this permitting cell repair, due to the maintenance of ECM anchoring. Accordingly, the identification by the inventors that the targeted binding of the hybrid domain of the beta1 integrin can modulate beta1 integrin allostery, this causing a marked observed therapeutic benefit in terms of the prevention of cell death following tissue insult or injury, is significant in that it promotes cell survival and permits cell/tissue repair and regeneration.

The allosteric modulation of the beta1 integrin can be characterised and/or monitored in terms of the effect on downstream signalling and function mediated by and through beta1 integrin. Accordingly, allosteric modulation of the beta1 integrin such that it assumes an intermediate affinity conformational state may be further co-characterised by the occurrence of at least one of the following which serve to reduce, prevent or revert cellular damage which may be associated with ECM degradation, cellular injury or death and disease progression: (i) remodelling of the extracellular matrix (ECM), (ii) inhibition of caspase activation, and in particular caspase 3 and caspase 7 and an associated reduction in apoptosis, (iii) suppression of F-actin aggregate formation, this in turn preventing an increase in cytoskeletal tension (iv) improved cellular energy homeostasis resulting from a reversion to normal sinusoidal oscillation of ATP levels, and associated improved levels of ATP recycling within a cell, (v) maintenance of beta1 integrin expression levels, (vi) inhibition of caveolin-1 phosphorylation, this being an indicator of an alteration of the cytomechanics of the cell and/or the degradation of the ECM and a reduction in tethering forces, which can result in clustering or aggregation of receptors, and (vii) inhibition of cell membrane physicochemical changes. (increased stiffness as a result of increased sphingomyelinase activity leading to increased ceramide content and raft formation.

Allosteric modulation of beta1 integrin in accordance with the present invention may be further characterised in that an increase in perlecan results, as well as there being an initial increase in tissue inhibitors of metalloproteinase-1 (TIMP-1) and a subsequent increase in pro-metalloproteinase-9.

In certain embodiments, the allosteric modulator compound can bind to beta1 integrin when beta1 integrin assumes any structural conformation, that is, the modulator compound can bind beta1 integrin irrespective of whether beta1 integrin assumes a low affinity (bent) or high affinity (extended) conformational state.

In certain embodiments, the allosteric modulator is selected from the group comprising of, but not limited to a: protein, peptide, peptidomimetic, nucleic acid, polynucleotide, polysaccharide, oligopeptide, carbohydrate, lipid, small molecule compound, aptamer, and naturally occurring compound such as a plant derived compound. Typically the allosteric modulator has binding specificity for beta 1 integrin and functions as an allosteric antagonist.

In certain embodiments, where the allosteric modulator is a protein, the protein is an antibody. An "antibody" is an immunoglobulin, whether natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody.

In certain embodiments, the allosteric modulator is an antibody selected from, but not limited to, the group comprising: a polyclonal antibody, a monoclonal, a humanized antibody, a chimeric antibody or a synthesized antibody. The antibody may be of an isotype selected from the group consisting of IgG, IgA, IgM, and IgE.

In certain embodiments, the antibody may bind to an epitope on beta 1 integrin with a dissociation constant (Kd) selected from the group of from about $10^{-7}$M to about $10^{-11}$M.

In certain further embodiments, where the allosteric modulator is a protein, the protein is a fusion protein, for example a fusion protein comprising an Fc domain derived from an antibody, said Fc domain being conjoined, by a linker or otherwise, to a protein fragment which has binding specificity for beta 1 integrin, and which acts as an allosteric modulator.

In certain embodiments, the allosteric modulator binds to at least one epitope present on the extracellular domain of human beta 1 integrin. In certain embodiments, the epitope which is bound by the beta 1 integrin allosteric modulator is distinct to the ligand binding epitope of beta 1 integrin.

In certain embodiments the beta 1 integrin allosteric antagonist binds to an epitope on beta 1 integrin comprising amino acid residues 82 and 87 of the mature amino acid sequence of human beta 1 integrin as defined in SEQ ID NO:1. Amino acid resides 82 (threonine) and 87 (lysine) are determined when the leader signal peptide is deducted from the defined amino acid sequence of human beta 1 integrin as defined in SEQ ID NO:1.

In certain embodiments the beta 1 integrin allosteric antagonist binds to an epitope on beta 1 integrin comprising amino acid residues 82 to 87 of the mature amino acid sequence of human beta 1 integrin as defined in SEQ ID NO:1.

In certain embodiments the beta 1 integrin allosteric antagonist binds to an epitope on beta 1 integrin comprising amino acid residues TAEKLK (SEQ ID NO:2) of the mature amino acid sequence of human beta 1 integrin as defined in SEQ ID NO:1.

In certain embodiments the beta 1 integrin allosteric antagonist binds to an epitope on beta 1 integrin comprising amino acid residues 179 to 184 of the mature amino acid sequence of human beta 1 integrin as defined in SEQ ID NO:1.

In certain embodiments the beta 1 integrin allosteric antagonist binds to an epitope on beta 1 integrin comprising amino acid residues TPAKLR (SEQ ID NO:3) of the mature amino acid sequence of human beta 1 integrin as defined in SEQ ID NO:1.

In certain embodiments the beta 1 integrin allosteric antagonist binds to an epitope on beta 1 integrin present within amino acid residues 207 to 218 of the mature amino acid sequence of human beta 1 integrin as defined in SEQ ID NO:1.

In certain embodiments the beta 1 integrin allosteric antagonist binds to an epitope on beta 1 integrin present within the hybrid domain comprising residues 60 to 139 of the mature amino acid sequence of human beta 1 integrin as defined in SEQ ID NO:1.

In certain embodiments the beta 1 integrin allosteric antagonist binds to an epitope on beta 1 integrin comprising amino acid residues 360 to 461 of the mature amino acid sequence of human beta 1 integrin as defined in SEQ ID NO:1.

The allosteric modulators may also be defined as beta 1 integrin binding compounds. A binding compound is a specific binding agent and refers to a natural or non-natural molecule that specifically binds to a target, in particular an epitope present on beta 1 integrin. Examples of suitable binding compounds for use in the present invention include, but are not limited to, proteins, peptides, peptidomimetics, nucleic acids, carbohydrates, aptamers, lipids, and small molecule compounds.

The term "specifically binds" or "binding specificity" refers to the ability of the binding compound to bind to a target epitope present on beta 1 integrin with a greater affinity than it binds to a non-target epitope. In certain embodiments, specific binding refers to binding to a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore assay. In certain embodiments, affinity is determined by a kinetic method. In certain embodiments, affinity is determined by an equilibrium/solution method.

In certain embodiments, the binding compound binds to at least one epitope present on epitope, wherein binding to this epitope results in the modulation of the allostery of beta 1 integrin. An "epitope" refers to a portion of beta 1 integrin which is capable of being recognised by and bound by a binding compound such as a small molecule or antibody by the binding region of said small molecule or antibody. Epitopes generally consist of chemically active surface groups and have specific three dimensional structural characteristics as well as specific charge characteristics. Typically, the binding compound antagonises the allostery of beta 1 integrin and as such binds to an epitope known as an inhibiting or inhibitory allosteric epitope. An "inhibiting" or "inhibitory" allosteric epitope means an epitope, that when bound by a binding compound, such as a small molecule or an antibody, results in the loss of allostery, and in particular of the ability of beta 1 integrin to assume an extended, activate conformation. An epitope present on beta 1 integrin, and which is bound by the binding compounds in order to antagonise beta 1 integrin allosteric function, may comprise 5 or more amino acid residues. In certain embodiments, the binding compounds recognise an epitope comprised of at least 5 continuous amino acid residues which is present from amino acid residues 60 to 139 and 360 to 461 of the amino acid sequence of the hybrid domain of the extracellular domain of human beta 1 integrin as defined herein in SEQ ID NO:1.

In certain embodiments, the beta1 integrin may be any member of the beta1 integrin family which comprises; beta1 integrin bound to α1, α2, α3, α7, α9, α4, α5, α8, and αv to form a heterodimer. The amino acid sequence of the hybrid domain of beta 1 integrin is identical irrespective of the particular beta 1 isoform.

In one embodiment the allosteric modulator binds to beta 1 integrin and induces a conformational change from a high affinity conformational state, wherein the extracellular domain is in an extended form with an open headpiece to an intermediate state, where the extracellular domain of beta 1 integrin is extended, but wherein the headpiece is in a closed conformation.

In an alternative embodiment, the allosteric modulator may bind beta1 integrin and induce a conformational change from an inactive state where the extracellular domain is in a bent conformation to an intermediate state.

The allosteric modulation of beta1 integrin, when bound by the allosteric modulator compound of the invention, therefore causes a modulation of the special or positional relationship of a cell to a substrate, wherein anchoring of a cell to the ECM is maintained. Such as relationship is important as adhesion of cells to their surrounding extracellular matrix (ECM) in-vivo regulates their morphology, proliferation, migration, survival and differentiation. In vitro, the interactions of cells with ECM molecules such as fibronectin result in cell attachment, spreading and the assembly of focal adhesions and actin stress fibres. The method of this aspect of the present invention may further modulate at least one of; cell attachment, cell spreading, migration, or the formation of a focal adhesion. The intracellular response of a cell to the ECM may also be modulated.

Without being bound by theory, the inventors predict that binding beta1 integrin with at least one allosteric modulator compound serves to induce a conformational change in the structure of beta1 integrin which causes beta1 integrin to assume an intermediate affinity state. This intermediate affinity state can be differentiated from the low and high affinity states which beta1 integrin is known to assume following inactivation and insult/injury respectively. Allosteric modulation of beta1 integrin which induces the assumption of an intermediate affinity state has been unexpectedly shown by the inventors to result in the prevention of ECM degradation and cell death following tissue insult or injury, with this observed cell survival allowing cell repair and regeneration processes to occur. Accordingly, cells and tissue which would have formerly have died through a process of programmed cell death, can be maintained in living form and associated repair can occur.

In particular, allosteric modulation of beta1 integrin has been identified by the inventors as being a potentially important therapeutic approach for use in tissue repair following injury or following the onset or development of autoimmune disease such as an autoimmune arthritis, such as rheumatoid arthritis or a lung condition, such as COPD, emphysema or chronic bronchitis. Pathogenesis observed following such tissue damage causes a change in the mechanical tethering of the cells to the ECM, with this in turn can change cell mechanosensing, this leading to a depletion in ATP levels due to the cessation of energy homeostasis resulting from sinusoidal oscillation of ATP levels within a cell. It has been shown herein for the first time that allosteric modulation, which causes beta1 integrin to assume an intermediate affinity state can result in a modification of cellular attachment to the underlying ECM, a reduction in mechanical stress and an increase in energy homeostasis, this further resulting in a reduction in detachment-induced apoptosis (anoikis).

Accordingly, the methods and modulatory compounds of the present invention which induce selective modulation of beta1 integrin can prevent cell death which can result from tissue insult, injury and disease. This reduction in cell death allows cells to survive, this allowing them to undergo repair and regeneration.

In one embodiment the allosteric modulator is the monoclonal antibody JB1a. The JB1a monoclonal antibody is obtainable as a commercial clone JB1a from Chemicon (Chemicon Europe Ltd, Hampshire, UK, and Millipore, catalogue number MAB-1965). The JB1a monoclonal antibody may also be referred to as the J10 monoclonal antibody.

The JB1a monoclonal antibody (JB1A mouse anti-CD29 (Integrin beta-1 subunit) IgG monoclonal antibody, unconjugated, clone JB1a, Millipore, Catalogue number MAB-1965) which is derived from the JB1a hybridoma cell line binds to an epitope between amino acid residues 82-87 of the beta1 integrin hybrid domain, irrespective of the conformational state of the receptor. This epitope may be defined as amino acid resides 62-67 when the 20 amino acid signal peptide leader sequence is removed from the defined human beta 1 integrin amino acid sequence.

The inventors have identified that the compositions and methods of the present invention have utility in the treatment of a number of conditions where tissue insult or injury occurs. These conditions include, but are not limited to, autoimmune arthritis, COPD, including emphysema and chronic bronchitis, cardiovascular disease and neurodegenerative disease.

Accordingly, a yet further aspect of the invention provides a method for the prophylaxis and/or treatment of autoimmune arthritis, the method comprising the steps of:
   providing a therapeutically effective amount an allosteric antagonist compound, wherein said allosteric modulator binds to beta1 integrin and mediates an allosteric change thereof such that the conformation of beta1 integrin assumes the intermediate affinity state, and
   administering the same to a subject in need of such treatment.

In certain embodiments, the autoimmune arthritis is at least one condition is selected from the group comprising, but not limited to: rheumatoid arthritis, inflammatory arthritis, juvenile rheumatoid arthritis, osteoarthritis and psoriatic arthritis. In further embodiments, the autoimmune arthritis may be collagen-induced arthritis.

In certain embodiments, where the autoimmune arthritis is rheumatoid arthritis, the beta 1 integrin allosteric modulator is brought into contact will a cell of the synovium, such the cells of the synovial membrane, for example, the intima or subintima.

Accordingly, a yet further aspect of the invention provides for the prophylaxis and/or treatment of chronic obstructive pulmonary disease (COPD), the method comprising the steps of:
  providing a therapeutically effective amount an allosteric antagonist compound, wherein said allosteric modulator binds to beta1 integrin and mediates an allosteric change thereof such that the conformation of beta1 integrin assumes the intermediate affinity state, and
  administering the same to a subject in need of such treatment.

In certain embodiments the chronic obstructive pulmonary disease (COPD) indication is selected from the group comprising, but not limited to: emphysema or chronic bronchitis.

Accordingly, a yet further aspect of the invention provides for the prophylaxis and/or treatment of a neurodegenerative disease, the method comprising the steps of:
  providing a therapeutically effective amount an allosteric antagonist compound, wherein said allosteric modulator binds to beta1 integrin and mediates an allosteric change thereof such that the conformation of beta1 integrin assumes the intermediate affinity state, and
  administering the same to a subject in need of such treatment.

In certain embodiments the neurodegenerative disease is selected from the group comprising, but not limited to: Alzheimer's disease (AD), mild cognitive impairment (MCI), multiple sclerosis (MS), Parkinson's disease, Amyotrophic lateral sclerosis (ALS), Huntington's disease, prion diseases such as CJD, AIDS-related dementia, encephalitis, stroke and head trauma.

Accordingly, a yet further aspect of the invention provides for the prophylaxis and/or treatment of tissue damage associated with a cardiovascular disease, the method comprising the steps of:
  providing a therapeutically effective amount an allosteric antagonist compound, wherein said allosteric modulator binds to beta1 integrin and mediates an allosteric change thereof such that the conformation of beta1 integrin assumes the intermediate affinity state, and
  administering the same to a subject in need of such treatment.

In certain embodiments, the cardiovascular disease is selected from the group comprising, but not limited to: stroke, ischemia, ischemia reperfusion and heart attack.

The invention further extends to a binding fragment derived from the JB1a monoclonal antibody, or an antibody which has binding specificity for an epitope present on beta 1 integrin, wherein binding of the antibody mediates allosteric modulation such that the beta 1 integrin assumes an intermediate conformation. For example, the allosteric antagonist may be a Fab fragment, scFV or fusion protein which is derived from, and maintains the binding specificity of, the JB1a monoclonal antibody. Furthermore, in certain embodiments, the allosteric antagonist of beta 1 integrin may be an aptamer which has binding specificity for beta 1 integrin, and which causes allosteric antagonism of the beta 1 integrin receptor. Techniques for the selection of suitable aptamers will be well known to the person skilled in the art, for example, using SELEX technology.

Accordingly the invention extends to a method of identifying and isolating nucleic acid ligands which have binding specificity for beta 1 integrin and which modulate the function of beta 1 integrin by acting as an allosteric antagonist, the method comprising the steps of:
  (a) providing a candidate mixture of nucleic acids
  (b) contacting beta 1 integrin protein with the candidate nucleic acid mixture
  (c) selecting nucleic acids which have an increased affinity to beta 1 integrin protein relative to the other candidate nucleic acids,
  (d) amplifying the selected nucleic acids in order to provide at least one nucleic acid with affinity for beta 1 integrin protein, and
  (e) selecting at least one nucleic acid therefrom which has a high affinity and specificity for beta 1 integrin protein.

As used herein, reference to "JB1a" include antibodies and binding fragment derived therefrom which have variable light, variable heavy or CRD (complementarity determining) sequences which show substantial homology with JB1a and which can be characterised in that they exhibit substantially identical binding specificity to that defined herein in relation to JB1a. In certain embodiments, the degree of homology between the amino acid resides which comprise the JB1a monoclonal antibody complementarity determining regions (CDRs) and the CDRs of other antibodies, or related binding fragments will be at least 60%, more preferably 70%, further preferably 80%, even more preferably 90% or most preferably at least 95% identical.

The invention further extends to immunoglobulins which have binding specificity for beta1 integrin, wherein binding of said immunoglobulin mediates a conformatory change which causes beta1 integrin to assume a conformation representative of an intermediate affinity state, and in particular where this binding is allosteric and effected at the hybrid domain of beta1 integrin, most preferably epitope between amino acid residues 82-87 of the human beta1 integrin hybrid domain.

In further embodiments, the allosteric modulator compound has binding specificity for the hybrid domain of beta1 integrin. The amino acid sequence of the hybrid domain is identical irrespective of the isoform of any beta1 integrin family member presently identified. In a further, specific embodiment, the allosteric modulator has binding specificity for the domain of beta1 integrin corresponding to residues 82-87 of the mature beta1 integrin. These residues have the sequence as defined in SEQ ID NO:1, namely TAEKLK (SEQ ID NO:2) (Threonine-Alanine-Glutamic Acid-Lysine-Leucine-Lysine), and can be further characterised in that they bind to this epitope irrespective of the overall conformation assumed by beta1 integrin.

For example, such allosteric modulator compounds may be small molecules (low molecular weight), or non-antibody modulating agents which are distinct from oligopeptide fragments of integrin ligands (e.g., ECM proteins, such as fibrinogen and fibronectin) and cyclic derivatives of these fragments.

More specifically, such allosteric modulator compounds may be derived from a fibronectin protein, for example the CBD portion of fibronectin, or the RGD sequence of the CBD; a vitronectin, or an analogue or an integrin binding portion of vitronectin; a laminin, or an analogue or an integrin binding portion of a laminin; a collagen, or an analogue or an integrin binding portion of a collagen; a polypeptide other than an ECM molecule which binds to a beta1 chain of integrin, e.g., a CBD-binding portion of integrin, e.g., a polypeptide selected for binding in, for example, a phage display or 2 hybrid assay; a small molecule, e.g., a small molecule capable of binding a beta1 chain of integrin, such as a CBD-binding portion of integrin. In a preferred embodiment, the method of this aspect of the invention comprises administering a nucleic acid (polynucleotide) which encodes one of the above-described agents.

In further embodiments, the allosteric modulator compound of the invention may be a disintegrin, or a variant or analogue thereof. Disintegrins are a family of naturally-occurring cysteine-rich peptides originally isolated from viper venom, but also found on cells and elsewhere, many of which contain the sequence Arg Gly Asp (RGD) as an integrin recognition site. Disintegrins are defined by their specific amino acid sequences and three-dimensional structures. "Variants" of disintegrins are disintegrins engineered to have one or more amino acids added, deleted or replaced. "Analogues" are non-peptide mimetics of disintegrins or their variants.

A further aspect of the invention provides a method for mediating tissue repair, the method comprising the step of administering to an individual in need of such treatment, a therapeutically effective amount of a compound which is an allosteric modulator of beta1 integrin, wherein the binding of the allosteric modulator to beta1 integrin induces the conformation of the beta1 integrin to assume an intermediate affinity state.

As used herein, the term 'tissue repair' means the physical or mechanical restoration or growth of damaged or diseased tissue by the repair or regeneration of tissue or cells following injury, insult, damage or trauma or following the onset of autoimmune disease or a disorder mediated by the immune system.

In one embodiment of this aspect of the invention, the method further comprises the step of administering at least one compound which inhibits matrix metalloproteinase (MMP) activity.

The method of this aspect of the invention may be used for the prophylaxis and/or treatment of any condition wherein extracellular matrix breakdown occurs. Such conditions may include; tumour invasion, infectious diseases, chronic inflammatory diseases such as rheumatoid arthritis or osteoarthritis, joint destruction in rheumatoid arthritis and osteoarthritis, periodontotitis and angiogenesis-dependent diseases such as corneal neovascularization, diabetic retinopathy, neovascular glaucoma, haemangioma, psoriasis, scleroderma and solid tumours, a neurological disease or disease of the central nervous system such as Alzheimer's disease, angiogenesis-dependent diseases, multiple sclerosis.

A yet further aspect of the invention provides a method for the prophylaxis and/or treatment of a condition which causes degeneration of the extracellular matrix, the method comprising the step of administering a therapeutically effective amount of an allosteric modulatory compound, wherein said allosteric modulator binds to beta1 integrin and mediates an allosteric change thereof such that the conformation of beta1 integrin assumes the intermediate affinity state to an individual in need of such treatment.

In one embodiment of this aspect of the invention, the method further comprises the step of administering at least one compound which inhibits matrix metalloproteinase (MMP) activity.

As herein defined, a "condition which causes degradation of the extracellular matrix" is a condition which causes or results from degenerative changes or break down to the extracellular matrix or to the cells of the extracellular matrix. Such degradation can result from the onset and progression of disease, such as infectious diseases and autoimmune or immune-mediated diseases. Further such conditions may include tumour.

In particular embodiments, the degeneration of the extracellular matrix or cells thereof comprises joint tissues, including articular cartilage or bone, intra-articular ligaments and tendons, wherein degradation leads to a loss of function. Such conditions may result from pathologies such as; tumours, chronic inflammatory diseases such as rheumatoid arthritis or osteoarthritis, a neurological disease or disease of the central nervous system such as Alzheimer's disease, angiogenesis-dependent diseases, multiple sclerosis, and ischemia.

The methods of the present invention may have further utility in the treatment and/or prophylaxis of; methods of treating inflammation; methods of treating and preventing viral infections; a method of treating shock; a method of treating arthritis; a method of suppressing immune responses; a method of treating an autoimmune disease; a method of inhibiting undesirable integrin-mediated cell-cell fusion; a method of inhibiting the formation of lesions; a method of treating psoriasis; a method of treating atherosclerosis; a method of treating diseases or conditions involving a plurality of integrin-dependent etiopathogenetic mechanisms; and a method of inhibiting the transfer of genetic material.

In addition, this aspect of the present invention further extends to a method of treating a tissue by contacting the tissue with an allosteric modulator compound according to the present invention. Such treatment improving the cellular structure of the tissue for subsequent use, as compared to tissue which is not treated with such a modulator compound. In particular, tissue which is to be transplanted into a recipient may be treated with an allosteric modulator compound according to the present invention, in order to increase the viability of the tissue.

In one embodiment of this aspect of the invention, the method further comprises the step of administering at least one compound which inhibits matrix metalloproteinase (MMP) activity to a subject in need of such treatment in order to mediate tissue repair.

In one embodiment the subject is a mammal. In a further embodiment the mammal is a human.

In one embodiment, the condition may include any condition where ECM breakdown or cell death occurs, for example such conditions may include; tumours, chronic inflammatory diseases such as rheumatoid arthritis or osteoarthritis, a neurological disease or disease of the central nervous system such as Alzheimer's disease, angiogenesis-dependent diseases, multiple sclerosis.

In a further embodiment the condition may be chronic obstructive pulmonary disease (COPD), chronic bronchitis or emphysema.

A yet further aspect of the present invention provides a pharmaceutical composition comprising a therapeutically effective amount of an allosteric modulatory compound, wherein said allosteric modulator binds to beta1 integrin and mediates an allosteric change thereof such that the conformation of beta1 integrin assumes the intermediate affinity state along with a pharmaceutically acceptable diluent, excipient or carrier.

In one embodiment of this aspect of the invention, the pharmaceutical composition may further comprise at least one compound which inhibits matrix metalloproteinase (MMP) activity.

Assays

The present invention further extends to assay methods which can be used to identify further compounds which serve to allosterically modulate beta1 integrin such that it assumes an intermediate affinity state.

Novel compounds identified using the assays of the invention as being allosteric modulators of beta1 integrin which mediate an allosteric change such that the conformation of beta1 integrin assumes the intermediate affinity state form a further independent aspect of the invention.

Accordingly, a yet further aspect of the present invention provides an assay method for the determination of an allosteric modulator compound, wherein said allosteric modulator binds beta1 integrin and mediates an allosteric change such that the conformation of beta1 integrin assumes the intermediate affinity state, said method comprising the steps of:
  providing an assay comprising beta1 integrin or a derivative thereof;
  activating beta1 integrin such that it assumes a conformation representative of a high affinity state,
  contacting a the activated beta 1 integrin with a candidate modulating agent under suitable conditions; and
  detecting a change of the conformation of beta1 integrin to an intermediate affinity state,
wherein modulation of the allostery of the beta 1 integrin from the high affinity conformational state to the intermediate affinity conformational state indicates that the candidate compound is an allosteric modulator of beta 1 integrin which has utility in mediating tissue repair.

In one embodiment the derivative of beta1 integrin may comprise an amino acid sequence comprising the hybrid domain of beta1 integrin, or a peptide fragment comprising at least residues 82-87 of the beta1 integrin hybrid domain having the amino acid sequence of SEQ ID NO:1.

In one embodiment, the contacting step is followed by an incubating step wherein the mixture obtained in the contacting step is incubated for a time period and under conditions suitable to allow interaction between the components and/or the test substance.

Further methods for identifying an allosteric modulator compound can be performed, for example, using a cell free assay. In a preferred embodiment, a compound can be identified using a cell based assay. These methods include identifying a compound based on its ability to allosterically modulate beta1 integrin this being characterised by enhancement of an adhesion-mediated activity of the cell. Examples of such adhesion mediated activities include: promoting focal adhesion assembly, promoting actin stress fibre formation; promoting an adhesion-mediated signalling pathway, e.g., a Rho dependent signalling pathway; promoting the interaction, e.g., binding, with a component of the extracellular matrix, e.g., fibronectin, vitronectin, a laminin, a collagen. In addition, the method includes identifying a compound on the basis of its ability to affect cell survival.

It is preferred that the assay be a cellular assay which may comprise cultured cells of primary or transformed cell lines, said cell lines being the result of the transfection of a cell line with an expression vector comprising the sequence or a substantial portion of the sequence a beta1 integrin polynucleotide sequence.

A yet further aspect of the present invention provides novel compounds identified from the assay methods described herein which act as allosteric modulator compounds of beta1 integrin in that they can bind to beta1 integrin and mediate an allosteric change thereof such that the conformation of beta1 integrin assumes the intermediate affinity state. Such compounds can be used in tissue repair in any tissue, for example tissue of the lung, skin, liver, kidney, nervous system, cartilage, bone and cardiovascular system. The compounds could have further utility in methods for the treatment of any condition where degradation of the ECM occurs, or where cell damage or cell death occurs, for example autoimmune conditions or infectious disease conditions and in particular in the treatment of conditions such as inflammation; viral infections shock; arthritis; suppressing immune responses; autoimmune disease; inhibiting undesirable integrin-mediated cell-cell fusion; inhibiting the formation of lesions; treating psoriasis; treating atherosclerosis; treating diseases or conditions involving a plurality of integrin-dependent etiopathogenetic mechanisms; and neurological diseases.

The present invention further provides assay methods for determining compounds which may be used to mediate tissue repair by virtue of their ability to act as allosteric modulator compounds, wherein said allosteric modulators binds to beta1 integrin and mediates an allosteric change thereof such that the conformation of beta1 integrin assumes the intermediate affinity state. As used herein, an "assay system" encompasses all the components required for performing and analysing results of an assay that detects and/or measures a particular event or events.

A variety of assays are available to detect the activity of compounds such as antibodies, peptides and chemicals which have specific binding activity to beta1 integrin examples of which are described herein. However, the precise format of the assay(s) of the invention may be varied by those skilled in the art using routine skill and knowledge. Preferred screening assays are high throughput or ultra high throughput and thus provide automated, cost-effective means of screening potential candidate compounds to identify their ability to allosterically modulate beta1 integrin such that the conformation of beta1 integrin assumes the intermediate affinity state.

Beta1 integrin allosteric modulating activity may be assessed in the assays of the invention using any suitable means. For example, the effect of the agent on MMP levels or balance, and/or the effect on apoptosis and apoptotic pathways. Exemplary assays are western blotting analyses and ELISA based assays for MMPs protein in both active and inactive forms, proteoglycans synthesis using western analyses and ELISA based assays, cell adhesion based assays, apoptosis assays using in-situ labelling, immunohistochemistry, immunofluorescence imaging and gel analyses.

In the assays of the invention, derivatives of beta1 integrin may be used. Such derivatives may comprise one or more fragments of beta1 may be used, for example the hybrid domain, or alternatively one or more binding sites of beta1 integrin may be used, for example the binding site corresponding to amino acid residues 82 to 87 of the mature beta1 integrin molecule.

Alternatively, the derivative may comprise a beta1 integrin mimetic. The skilled person is well aware of how to design such a mimetic. Briefly, a template molecule is selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the beta1 integrin.

The mimetic found by this approach can then be used in assays of the invention in place of beta1 integrin to ascertain whether the candidate compounds can allosterically modulate the beta1 integrin mimetic to identify whether said allosteric modulator binds to beta1 integrin and mediates an allosteric change thereof such that the confirmation of beta1 integrin assumes the intermediate affinity state.

The inventors have further recognised the utility of the beta1 integrin allosteric modulatory compounds of the present invention in uses for the treatment of tissue repair in any tissue, for example tissue of the lung, skin, liver, kidney, nervous system, cartilage, bone and cardiovascular system and further in relation to increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders.

Accordingly, a yet further aspect of the present invention provides for the use of an allosteric modulator of beta1 integrin which modulates the beta1 integrin into an intermediate affinity state in the preparation of a medicament for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders such as COPD or emphysema.

A yet further aspect of the present invention provides for the use of an allosteric modulator of beta1 integrin which modulates the beta1 integrin into an intermediate affinity state in the preparation for the treatment of an autoimmune disease. The autoimmune disease may be rheumatoid arthritis, or psoriasis, or multiple sclerosis.

A yet further aspect of the present invention provides the use of an allosteric modulator of beta1 integrin which modulates the beta1 integrin into an intermediate affinity state in the preparation of a medicament for mediating tissue repair and regeneration.

A yet further aspect of the present invention provides the use of an allosteric modulator of beta1 integrin which modulates beta1 integrin into an intermediate affinity state for the inhibition of caspase activation and/or apoptosis. In one embodiment the caspase is caspase 3. In a further embodiment the caspase is caspase 7.

A yet further aspect of the present invention provides the use of an allosteric modulator of beta1 integrin which modulates the beta1 integrin into an intermediate affinity state for the inhibition of caveolin-1 phosphorylation.

A yet further aspect of the invention provides a method for the inhibition of apoptosis within a cell, said effect being mediated by inhibiting or decreasing the production of at least one of caspase 3 and caspase 7, the method comprising the step of administering a therapeutically effective amount of an allosteric modulator compound which binds to beta1 integrin and mediates an allosteric change such that the conformation of beta1 integrin assumes the intermediate affinity state to an individual in need of such treatment.

A yet further aspect of the present invention provides for the use of an allosteric modulator of beta1 integrin which modulates the beta1 integrin into an intermediate affinity state and a compound which inhibits matrix metalloproteinase activity in the preparation of a combined medicament for the prophylaxis and/or the treatment of pathologies selected from the group comprising; tumours, chronic inflammatory diseases such as rheumatoid arthritis or osteoarthritis, a cardiovascular disease, a neurological disease or disease of the central nervous system such as Alzheimer's disease, angiogenesis-dependent diseases, multiple sclerosis or conditions requiring the inhibition of matrix metalloproteinase (MMP) activity.

A yet further aspect of the present invention provides a pharmaceutical composition for the prophylaxis and/or the treatment of pathologies selected from the group comprising; tumours, chronic inflammatory diseases such as rheumatoid arthritis or osteoarthritis, a neurological disease or disease of the central nervous system such as Alzheimer's disease, angiogenesis-dependent diseases, multiple sclerosis or conditions requiring the inhibition of matrix metalloproteinase (MMP) activity comprising an allosteric modulator of beta1 integrin which modulates the beta1 integrin into an intermediate affinity state and a compound which inhibits matrix metalloproteinase activity along with at least one suitable pharmaceutical excipient.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

The term "or" is used herein to mean, and is used interchangeably with, the term "and/or", unless context clearly indicates otherwise.

As used herein, the terms "about" and "approximately" shall generally mean an acceptable degree of error for the quantity measured given the nature or precision of the measurements. Exemplary degrees of error are within 20 percent (%), typically within 10%, and more typically, within 5% of a given value or range of values. In the context of a range value for an amino acid or nucleotide sequence, the term "about" includes a range that differs by 1, 2, 3, 4 or 5 residues or nucleotides at one or both end points. For example, the phrase "about amino acids 9 to 22" of a sequence can include amino acid sequences, such as 7 to 23 and 11 to 20 of the amino acid sequence specified.

The nomenclature used to describe the polypeptide constituents of the fusion protein of the present invention follows the conventional practice wherein the amino group (N) is presented to the left and the carboxy group to the right of each amino acid residue.

The expression "amino acid" as used herein is intended to include both natural and synthetic amino acids, and both D and L amino acids. A synthetic amino acid also encompasses chemically modified amino acids, including, but not limited to salts, and amino acid derivatives such as amides. Amino acids present within the polypeptides of the present invention can be modified by methylation, amidation, acetylation or substitution with other chemical groups which can change the circulating half life without adversely affecting their biological activity.

The terms "peptide", "polypeptide" and "protein" are used herein interchangeably to describe a series of at least two amino acids covalently linked by peptide bonds or modified peptide bonds such as isosteres. No limitation is placed on the maximum number of amino acids which may comprise a peptide or protein. Furthermore, the term polypeptide extends to fragments, analogues and derivatives of a peptide, wherein said fragment, analogue or derivative retains the same biological functional activity as the peptide from which the fragment, derivative or analogue is derived Furthermore the term "fusion protein" as used herein can also be taken to mean a fusion polypeptide, fusion peptide or the like, or may also be referred to as an immunoconjugate. The term "fusion protein" refers to a molecule in which two or more subunit molecules, typically polypeptides, are covalently or non-covalently linked.

As used herein, the term "therapeutically effective amount" means the amount of beta 1 integrin allosteric modulator which is required to mediate a conformational change of beta 1 integrin in order to mediate tissue repair. The tissue repair may be used to treat a cancerous condition, an autoimmune condition, such as autoimmune arthritis, a cardiovascular disease, or a neurodegenerative disease or at least one symptom thereof.

As used herein, the term "prophylactically effective amount" relates to the amount of a composition which is required to prevent the initial onset, progression or recurrence of a tissue injury in a disease condition such as a cancerous condition, an autoimmune condition, such as autoimmune arthritis, a cardiovascular disease, or a neurodegenerative disease or at least one symptom thereof, said tissue damage, insult or injury being mediated by beta 1 integrin assuming an extended conformation, in a subject following the administration of the compounds of the present invention.

As used herein, the term "subject" refers to an animal, preferably a mammal and in particular a human. In a particular embodiment, the subject is a mammal, in particular a human. The term "subject" is interchangeable with the term "patient" as used herein.

All publications, patent applications, patents, and other references mentioned herein are incorporated by reference in their entirety.

Other features and advantages of the invention will be apparent from the description, drawings and from the claims.

BRIEF DESCRIPTION OF DRAWINGS

The present invention will now be described with reference to the following examples which are provided for the purpose of illustration and are not intended to be construed as being limiting on the present invention, and further, with reference to the figures.

FIG. 1 shows the effect of porcine pancreatic elastase (PPE) on respiratory function in mice and its reversal using the anti-beta1 integrin antibody JB1a. FIG. 1(a) shows the effect of PPE on mean respiratory pressure-volume curves in mice 35 days (35 d) after instillation and its reversal by JB1a (JB) (Vehicle=Veh). FIG. 1(b) shows the reversal of PPE-induced increase in the constant k by JB1a treatment at different time points post injury. JB1a treatment once or twice following PPE-induced injury reversed the time-dependent effect on peak respiratory pressure from the pressure-volume curves (FIG. 1(c)) and the quasi-static elastase derived from a. (FIG. 1(d)). n=5-6 in 35 d (35 day) groups and n=10 in 21 d (21 day) groups, FIG. 2 shows the effect of PPE on lung structure and its reversal by JB1a treatment. FIG. 2(a) shows haematoxylin and eosin staining of lung sections from veh, PPE and JB instilled mice from 21 d (21 day) and 35 d (35 day) groups. FIG. 2(b) shows mean linear intercept measurements from the 21 d and 35 d groups. Automated stereological estimates of the number of (FIG. 2(c)) contiguous airspaces, (FIG. 2(d)) septal junctions, and (FIG. 2(e)) septal ends from the 21 day group (n=5), FIG. 3(a) shows 3D reconstructions of PPE-injured lung in the 21 day group of lung parenchyma (blue, Column I), and the expression patterns of GATA-6 (yellow) and TTF-1 (red, Column II). Column III shows an overlay of parenchyma and expression patterns of GATA-6 and TTF-1. Column IV shows a detail of (Column I) at higher magnification. Column V shows a detail of (Column II) at higher magnification. FIG. 3(b) shows TUNEL staining of lung tissue sections from 21 d (21 day) and 35 d (35 day) groups demonstrating the effect of JB1a treatment after PPE-induced lung injury. FIG. 3(c) shows the quantification of TUNEL positive cells following PPE-induced injury and JB1a treatment. n=5-6 per group, FIG. 5 shows the effect of allosteric modulation of beta1 integrin using JB1a on metalloproteinases and tissue inhibitors of metalloproteinases (MMPs) in primary human lung alveolar/mesenchymal co-cultures. FIG. 5(a) shows the effect of JB1a on MMP1 levels and activity at two different time points when added alone and in the presence of APMA, cycloheximide (CXH), neutralising antibodies against MMPs 7 and 9 and broad spectrum MMP inhibitor. FIG. 5(b) demonstrates the effects JB1a on tissue inhibitor of metalloproteinase-1 (TIMP1). FIG. 5(c) shows the effect of JB1a on the levels of inactive MMP9 (pro-MMP9). The experiment was repeated 3 times using cells derived from different patients, FIG. 6(a)-(c) shows RGB images from JB (FIG. 6(a)), PPE (FIG. 6(b)), and veh lungs (FIG. 6(c)) were pre-processed with morphological filters (FIGS. 6(d)-(f)) to aid automated edge detection and to remove noise. In FIG. 6(g)-(i) a 200 mm×200 mm frame was superimposed over preprocessed images. Only events completely inside the frame or intersecting the two inclusion edges (South-West boundaries) are considered and any events intersecting the exclusion lines (North-East boundaries) are not sampled. The number of contiguous airspaces (FIG. 6(g)-(i)), septal branches (Figure (j)-(i), white dots), and free septal ends (m-o, white dots) was determined in reticulin-stained sections of lung, FIG. 7 shows images from time-lapse movies showing the effect of vehicle (FIG. 7(a)) elastase ((FIG. 7(b), 0.6 U/ml) on F-actin (blue) and caspase 3/7 activation (red) in vitro using human lung co-culture during mechanical stretch and its inhibition by JB1a (FIG. 7(c), 1 µg/ml). Syto 16-green. A figure of the selected frames from the recording is provided), FIG. 8 shows 3D reconstructions of images of human lung co-culture after injury using elastase (b, e; 0.6 U/ml) demonstrating the formation of F-actin (blue) and caspase 3/7 activation (red). (Ganglioside GM1 for the cell membrane-green) and its inhibition by JB1a (c, f; 1 µg/ml). Vehicle (a, d), FIG. 10(a) shows the effect of elastase-induced injury (0.3 U/ml) on sphingomyelinase activity in human lung co-culture during mechanical stretch at 2-12% amplitude at different time points and its inhibition by JB1a (2 ug/ml) (n=3-4). FIG. 10(b) shows the level of sphingomyelinase activity and kinetics in in-vivo mouse lung after injury using elastase (0.2 U/g body weight) demonstrating the an increase in the level of sphingomyelinase after 35 days and its inhibition by JB1a (3 mg/kg on days 21 and 28) (n=5), FIG. 13(a) shows the effect of two doses of JB1a on FCA-induced ipsilateral joint dimension increase. FIG. 14(b) shows the effect of two doses of JB1a on the contralateral joint dimension after FCA intra-articular injection. FIG. 13(c) shows the effects of JB1a on FCA-induced hyperalgesia. FIG. 13(d) shows the effects of JB1a on the reversal of abnormal histological scores of the ipsilateral joints induced by FCA. FIG. 13(e) shows the haematoxylin and eosin staining of median sections from Vehicle (Veh), FCA, JB1a, isotype and sham treated mice. FIG. 13(f) shows alcian blue staining of the ipsilateral articular joint demonstrating the reversal effects of JB1a on FCA-induced glycosaminoglycan loss and metachromasia. FIG. 13(g) shows a graph of the quantification of the effect of JB1a on FCA-induced chondrocytes cell death, FIG. 14 shows the effects of IL-1beta-induced injury and JB1a treatment on caspase activity, ATP levels and IL-8 concentration. FIG. 14(a) shows a bar chart indicating that JB1a inhibits IL-1beta-induced caspase 3/7 activation (n=9). Data from all time points for a given treatment were pooled as the effect of time was not significant. FIG. 14(b) shows a graph illustrating IL-1 beta (10 ng/ml) effects on ATP post 3 hours IL-1beta-induced injury and the effect of JB1a on IL1beta-induced ATP changes (each curve represents n=2, each done in triplicates). c. IL-1beta effect on IL8 levels and its partial reversal by JB1a (n=3, each done in duplicates), FIG. 15(a) shows the effect of beta-amyloid fibrils on primary cortical neurons. Beta amyloid fibrils induced caspase activation (arrowhead) and raft formation (arrow). Both effects were inhibited by JB1a. FIG. 15(b) shows JB1a inhibition of amyloid fibril effects were accompanied by morphological changes, FIG. 16 shows SEQ ID NO:1, this being the amino acid sequence of human beta 1 integrin (Genbank Accession Number P05556 (Integrin beta-1 precursor (Fibronectin receptor subunit beta) Integrin VLA-4 subunit beta, CD29 antigen))

DETAILED DESCRIPTION OF THE INVENTION

Figure 3:
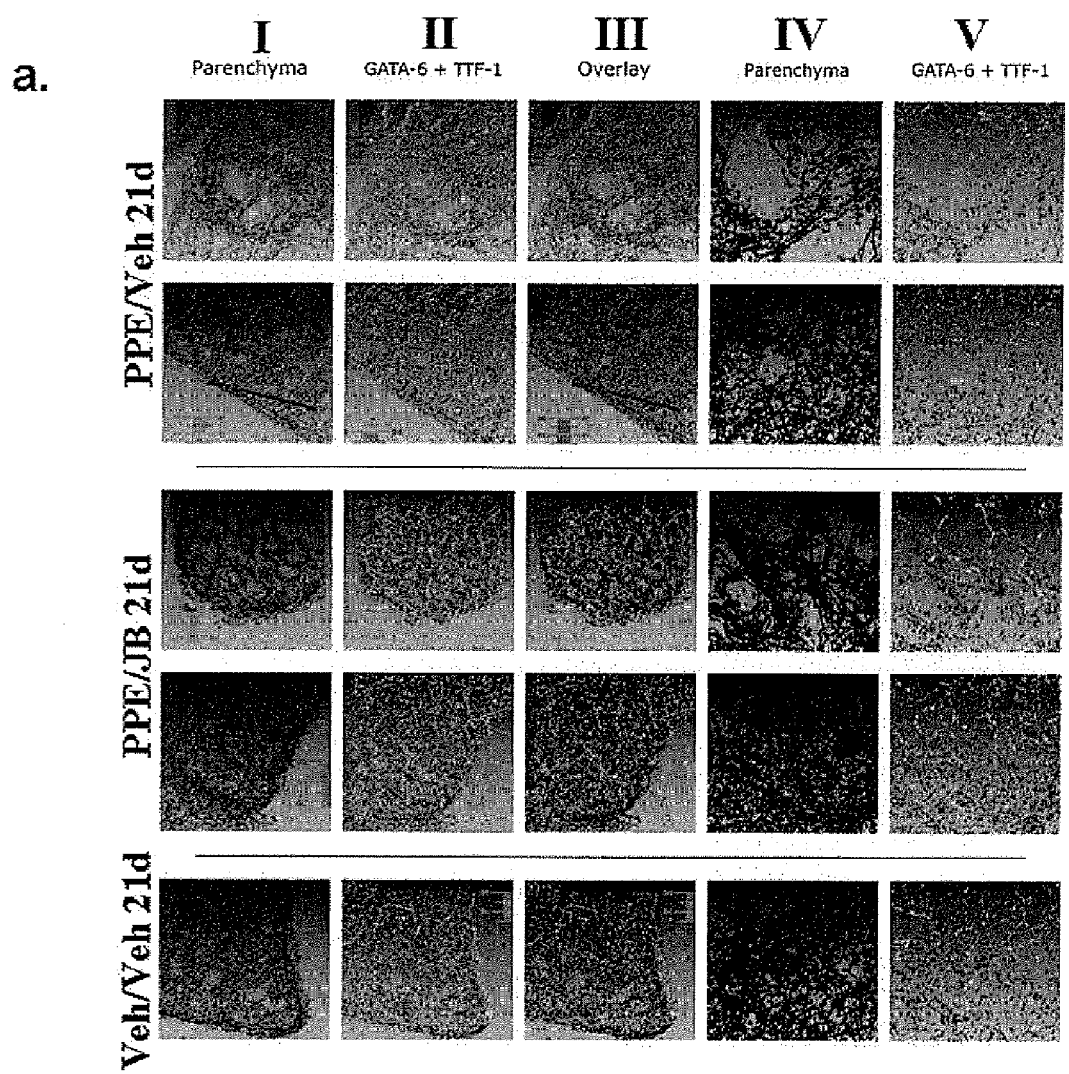
FIG. 3 shows the effect of allosteric modulation of beta1 integrin GATA-6 and TTF-1 expression after PPE-induced.

The present invention relates to compounds and methods for use in allosterically modulating beta 1 integrin in order to mediate tissue repair.

The amino acid sequence of human beta 1 integrin is provide in FIG. 16 as SEQ ID NO:1. The 798 amino acid sequence of beta 1 integrin is available from the Genbank database of sequences, under Genbank Accession Number P05556 ((Integrin beta-1 precursor (Fibronectin receptor subunit beta) Integrin VLA-4 subunit beta, CD29 antigen).

The key region involved in ligand recognition and binding is the top face of the A domain. This domain contains a metal ion dependent adhesion site (MIDAS). The A domain of beta integrin is linked to the immunoglobulin-like hybrid domain. The hybrid domain acts as a lever, wherein the angle between the A domain and hybrid domain controls beta 1 integrin receptor conformation and, accordingly, ligand binding affinity. The "legs" of the integrin are composed of multiple globular domains known as EGF-repeats (epidermal like growth factor repeats), which incorporate two knee-like joints referred to as genu. The EGF-repeats are linked to cytoplasmic tail domains via a single transmembrance pass.

Ligand binding has been shown to induce the opening (or an increase) in the angle between the A and hybrid domains of beta 1 integrin in the integrin headpiece. The opening of this hinge is indicative of the switch to a high binding affinity. A further site which is of importance in affinity regulation is the metal ion dependent adhesion site (MIDAS) within the A domain. A MIDAS site is also thought to be present in the alpha chains containing the I domain. Integrin-ligand interactions have been shown to be affected by the binding of divalent cations, such as magnesium, manganese and calcium at these MIDAS sites. For example, the binding of calcium is shown to have an inhibitory effect on beta 1 integrin by stabilising the low-affinity conformation of beta 1 integrin.

Integrins are known to undergo global structural rearrangement upon activation, with this structural rearrangement resulting in the exposure of ligand binding sites. The overall strength of cellular adhesiveness or avidity is governed by affinity and valency. Valency relates to the density of the receptor and its ligand on the cell surface, as well as the special and geometric arrangement and movement.

Integrins can be summarised as having three main possible structural conformations of the extracellular domain. These are (i) a low affinity, bent conformation, (ii) an intermediate affinity state which is characterised by an extended conformation, with a bent headpiece, and (iii) a high affinity, extended form, wherein ligand binding induces the headpiece to extend in an open conformation.

The function of beta 1 integrin has been studied using a genetic approach. These studies have shown that beta 1 integrin has an effect on cell survival and proliferation, as well as remodelling of the extra-cellular matrix. These effects are both cell type and development stage type dependent.

Inactive integrins are conformationally bent and the headpiece is approximately 5 nm away from the membrane. Upon activation, integrins undergo a switchblade-like extension, this resulting in the integrin transforming from a bent state to an extended state. This extended state increases the accessibility of the headpiece to interact with ligands. For example, the binding of fibronectin to the alpha5beta1 integrin was shown to induce an open conformation, by means of an 80 degree increase in the angle of the hybrid domain of the beta subunit relative to the I-like (A) domain.

The separation of the alpha and beta subunit legs is a critical step in inside-out integrin activation, which results in transformation of the extended conformation and allowing headpiece-ligand engagement. Disrupting the integrin heterodimeric transmembrane helix-helix interface activates ligand binding mainly by increasing the monomeric affinity for ligand, and not the receptor valency (i.e. clustering). This separation is initiated by the heterodimer intersubunit dissociation between their transmembrane and cytoplasmic domains. Activation and opening of the beta 1 integrin MIDAS can result from the swing-out of the beta subunit hybrid domain, pulling on the C-terminal alpha helix of the beta 1 domain in a manner similar to a bell rope. At this level of extension, the integrin headpiece projects at 20 to 25 nm above the plasma membrane, making the receptor ligand competent. Both the EGF-like and hybrid domains are key in transducing the cytoplasmic tail rearrangements into separation and straightening of the integrin ectodomain. This is because when the hybrid domain undergoes a sing-out motion through inside-out signalling, it causes a partial opening of the beta 1 integrin I-like domain, and ligand binding occurs leading to outside-in activation.

Inside-out activation of integrins entails changes in the conformation initiated at the cytoplasmic clasp and transmitted to the headpiece MIDAS domain via the leg domains. Outside-in activation is a term which describes the activation occurring when ligand binding to the headpiece domain induces changes in the headpiece as well as in the orientation of the leg domains and the cytoplasmic regions. High-affinity states can be artificially induced by chemically locking extended and open integrin conformations or by stabilising these states with monoclonal antibodies prior to binding.

There are multiple cation binding sites present in both the alpha and beta integrin subunits. Divalent cations have been shown to induce a conformational relaxation in the integrin, this resulting in exposure of ligand binding sites. These sites lie near the interface between the alpha beta-propeller and the beta subunit A (I-like) domain.

Figure 17:
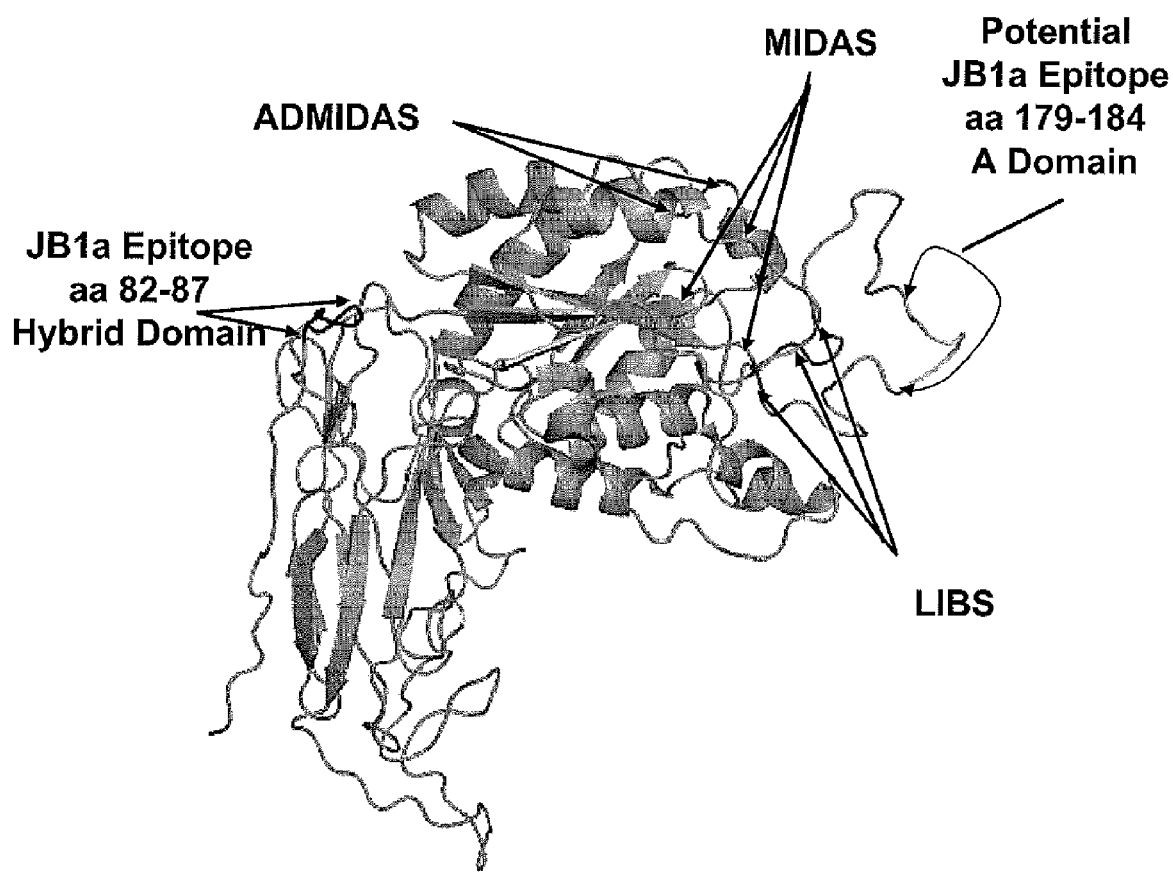
FIG. 17 shows the predicted crystalline structure of human beta 1 integrin.

One such site lies in the beta subunit A domain and is known as the metal ion dependent adhesion site (MIDAS). Another cation binding site is known as the ADMIDAS (adjacent to the MIDAS). The ADMIDAS is important in stabilising the active conformation of the integrin, since mutations in this site inhibit integrin activation and conformational changes are markedly increased. The predicted position of the MIDAS and ADMIDAS sites in the crystal structure of beta 1 integrin is shown in FIG. 17.

The extracellular matrix (ECM) interacts with integrins and modifies their function. In turn, integrins are key regulators of the ECM. Their main functions are cell-ECM and cell-cell adhesion. One hallmark feature is ability of integrins to process signals bidirectionally across the cell membrane. Additionally, integrins are mechanotransducers, converting mechanical signals to biochemical changes. These properties give integrins key roles in cell growth, differentiation, migration, and survival.

Integrins in general, including the beta1 subfamily, are known to exhibit global structural rearrangement and exposure of ligand binding sites upon activation. The overall strength of cellular adhesiveness or avidity is governed by affinity and valency; the latter governed by the density of the receptor and its ligand on the cell surface as well as the spatial and geometric arrangement and movement of the integrin.

Heterodimers of beta1 integrin bind collagens ($\alpha 1$, $\alpha 2$), laminins ($\alpha 1$, $\alpha 2$, $\alpha 3$, $\alpha 7$, $\alpha 9$) and fibronectin ($\alpha 3$, $\alpha 4$, $\alpha 5$, $\alpha 8$, $\alpha v$). Furthermore, beta1 integrin can also bind metalloproteinases (MMPs) such as MMP2 and MMP9 and affect their activation state.

Several pathological processes involve tissue remodelling and degradation including; tumour invasion, joint destruction in rheumatoid arthritis and osteoarthritis, periodontotitis and angiogenesis-dependent diseases such as corneal neovascularization, diabetic retinopathy, neovascular glaucoma, haemangioma, psoriasis, scleroderma and solid tumours. Basement membrane and interstitial connective tissue make up the ECM, which is composed of collagen, proteoglycans and adhesion glycoproteins. ECM provides a physical support to cells and tissues and cell-ECM interactions regulate cell growth, differentiation and migration. ECM degrading enzymes include matrix metalloproteases (MMPs), urokinase, tissue plasminogen activator, cathepsins, trypsins and heparanases. The integrin-mediated function of adhesion is important for a variety of physiological and pathological responses. The extent of adhesion is controlled by integrin signalling.

Antibodies

An "antibody" is an immunoglobulin, whether natural or partly or wholly synthetically produced. The term also covers any polypeptide, protein or peptide having a binding domain that is, or is homologous to, an antibody binding domain, particularly that of the JB1a monoclonal antibody. Such binding compounds can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd, and a bi-specific antibody. So called "domain antibodies" may also be produced, as can binding fragments based on or derived from Camelid or shark antibodies.

As antibodies can be modified in a number of ways, the term "antibody" should be construed as covering any binding member or compound having a binding domain with the required binding specificity as defined hereinbefore. The antibody may be a monoclonal antibody, or a fragment, derivative, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in European Patent Application Publication Number EP 0,120,694 and European Patent Application Publication Number EP 0,125,023.

The constant region of the antibody may be of any suitable immunoglobulin subtype, however it is preferred that the antibody subtype is IgG1. However, in alternative embodiments, the subtype of the antibody may be of the class IgA, IgM, IgD and IgE where a human immunoglobulin molecule is used. Such an antibody may further belong to any sub class e.g. IgG1, IgG2a, 2b, IgG3 and IgG4. In further embodiments, the constant region may be derived from an immunoglobulin subtype from a non-human source such as any other animal, in particular a mouse.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi-specific antibody, which may be multivalent or multispecific fragments constructed by gene fusion.

A fragment of an antibody or of a polypeptide for use in the present invention, for example, a fragment of the JB1a antibody, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids. A preferred group of fragments are those which include all or part of the CDR regions of monoclonal antibody JB1a.

A "derivative" of such an antibody or polypeptide, or of a fragment of a JB1a antibody means an antibody or polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having interferon alpha binding activity. Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

The term "antibody" includes antibodies which have been "humanised". Methods for making humanised antibodies are known in the art. Methods are described, for example, in Winter, U.S. Pat. No. 5,225,539. A humanised antibody may be a modified antibody having the hypervariable region of a monoclonal antibody such as JB1a and the constant region of a human antibody. Thus the binding member may comprise a human constant region.

The variable region other than the hypervariable region may also be derived from the variable region of a human antibody and/or may also be derived from a monoclonal antibody such as JB1a. In such case, the entire variable region may be derived from murine monoclonal antibody JB1a and the antibody is said to be chimerised. Methods for making chimerised antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184,187, GB 2,188,638A or EP-A-239,400. A hybridoma or other cell producing an antibody may be subject to genetic mutation or other changes, which may or may not alter the binding specificity of antibodies produced.

Production of Antibodies

Certain methodologies for producing antibodies which have an affinity and binding specificity for beta 1 integrin are described hereinbefore.

The antibodies provided by the present invention may be provided by a number of techniques. For example, a combinatorial screening technique such as a phage display-based biopanning assay may be used to in order to identify amino acid sequences which have binding specificity to the binding epitopes of the invention. Such phage display biopanning techniques involve the use of phage display libraries, which are utilised in methods which identify suitable epitope binding ligands in a procedure which mimics immune selection, through the display of antibody binding fragments on the surface of filamentous bacteria. Phage with specific binding activity are selected. The selected phage can thereafter be used in the production of chimeric, CDR-grafted, humanised or human antibodies.

In further embodiments, the antibody is a monoclonal antibody may be produced using any suitable method which produces antibody molecules by continuous cell lines in culture. Suitable methods will be well known to the person skilled in the art and include, for example, the method of Kohler and Milstein (Kohler et al. Nature, 256, 495-497. 1975), Chimeric antibodies or CDR-grafted antibodies are further provided within the scope of the present invention. In further embodiments, the antibodies of the invention may be produced by the expression of recombinant DNA in host cell.

In further embodiments, humanized antibodies are also provided. Humanized antibodies may be produced by the method of Winter as described in U.S. Pat. No. 5,585,089.

In further certain embodiments, the monoclonal antibodies may be human antibodies, produced using transgenic animals, for example, transgenic mice, which have been genetically modified to delete or suppress the expression of endogenous murine immunoglobulin genes, with loci encoding for human heavy and light chains being expressed in preference, this resulting in the production of fully human antibodies.

The antibodies or antibody fragments of and for use in the present invention may also be generated wholly or partly by chemical synthesis. The antibodies can be readily prepared according to well-established, standard liquid or, preferably, solid-phase peptide synthesis methods, general descriptions of which are broadly available and are well known by the person skilled in the art. Further, they may be prepared in solution, by the liquid phase method or by any combination of solid-phase, liquid phase and solution chemistry.

Another convenient way of producing antibodies or antibody fragments suitable for use in the present invention is to express nucleic acid encoding them, by use of nucleic acid in an expression system.

Nucleic acid for use in accordance with the present invention may comprise DNA or RNA and may be wholly or partially synthetic. In certain aspects, nucleic acid for use in the invention encodes antibodies or antibody fragments for use in the invention as defined above. The skilled person will be able to determine substitutions, deletions and/or additions to such nucleic acids which will still provide an antibody or antibody fragment of the present invention.

Nucleic acid sequences encoding antibodies or antibody fragments for use with the present invention can be readily prepared by the skilled person using the information and references contained herein and techniques known in the art (for example, see Sambrook et al. (1989), and Ausubel et al, (1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The nucleic acid may be comprised as constructs in the form of a plasmid, vector, transcription or expression cassette which comprises at least one nucleic acid as described above. The construct may be comprised within a recombinant host cell which comprises one or more constructs as above. Expression may conveniently be achieved by culturing under appropriate conditions recombinant host cells containing the nucleic acid. Following production by expression the antibody or antibody fragments may be isolated and/or purified using any suitable technique, then used as appropriate.

Systems for cloning and expression of a polypeptide in a variety of different host cells are well known. Suitable host cells include bacteria, mammalian cells, yeast, insect and baculovirus systems. Mammalian cell lines available in the art for expression of a heterologous polypeptide include Chinese hamster ovary (CHO) cells, HeLa cells, baby hamster kidney cells, NS0 mouse myeloma cells. A common, preferred bacterial host is *E. coli*. The expression of antibodies and antibody fragments in prokaryotic cells such as *E. coli* is well established in the art. Expression in eukaryotic cells in culture is also available to those skilled in the art as an option for production of a binding member.

General techniques for the production of antibodies are well known to the person skilled in the field, with such methods being discussed in, for example, Kohler and Milstein (1975) Nature 256: 495-497; U.S. Pat. No. 4,376,110; Harlow and Lane, Antibodies: a Laboratory Manual, (1988) Cold Spring Harbor, the contents of which are incorporated herein by reference.

Techniques for the preparation of recombinant antibody molecules is described in the above references and also in, for example, EP 0,623,679 and EP 0,368,684, which are incorporated herein by reference.

In preferred embodiments of the invention, recombinant nucleic acids comprising an insert coding for a heavy chain variable domain and/or for a light chain variable domain of antibodies are employed. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or a light chain variable domain of antibodies can be enzymatically or chemically synthesised nucleic acids having the authentic sequence coding for a naturally-occurring heavy chain variable domain and/or for the light chain variable domain, or a mutant thereof.

Recombinant DNA technology may be used to improve the antibodies of the invention. Thus, chimeric antibodies may be constructed in order to decrease the immunogenicity thereof in diagnostic or therapeutic applications. Moreover, immunogenicity within, for example, a transgenic organism such as a pig, may be minimised, by altering the antibodies by CDR grafting in a technique analogous to humanising antibodies. Examples of such techniques are described in EP 0,239,400 to Winter.

In order to reduce immunogenicity within a recipient, the invention may employ recombinant nucleic acids comprising an insert coding for a heavy chain variable domain of an antibody fused to a human constant domain. Likewise the invention concerns recombinant DNAs comprising an insert coding for a light chain variable domain of an antibody fused to a human constant domain κ or λ.

Antibodies may moreover be generated by mutagenesis of antibody genes to produce 5 artificial repertoires of antibodies. This technique allows the preparation of antibody libraries. Antibody libraries are also available commercially. Hence, the present invention advantageously employs artificial repertoires of immunoglobulins, preferably artificial scFv repertoires, as an immunoglobulin source in order to identify binding molecules which have specificity for the epitope of the present invention.

Antibody Selection Systems

Immunoglobulins which are able to bind to the epitope of the present invention and which accordingly may be used in the methods of the invention can be identified using any technique known to the skilled person. Such immunoglobulins may be conveniently isolated from libraries comprising artificial repertoires of immunoglobulin polypeptides. A "repertoire" refers to a set of molecules generated by random, semi-random or directed variation of one or more template molecules, at the nucleic acid level, in order to provide a multiplicity of binding specificities. Methods for generating repertoires are well characterised in the art.

Any library selection system may be used in conjunction with the invention. Selection protocols for isolating desired members of large libraries are known in the art, as typified by phage display techniques. Such systems, in which diverse peptide sequences are displayed on the surface of filamentous bacteriophage, have proven useful for creating libraries of antibody fragments (and the nucleotide sequences that encode them) for the in vitro selection and amplification of specific antibody fragments that bind a target antigen. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straight forward.

Methods for the construction of bacteriophage antibody display libraries and lambda phage expression libraries are well known in the art (for example, McCafferty et al. (1990) Nature 348 552-554. One particularly advantageous approach has been the use of scFv phage-libraries (see for example Huston et al., 1988, Proc. Natl. Acad. Sci. USA).

An alternative to the use of phage or other cloned libraries is to use nucleic acid, preferably RNA, derived from the B cells of an animal which has been immunised with the selected target, e.g. beta 1 integrin.

Isolation of V-region and C-region mRNA permits antibody fragments, such as Fab or Fv, to be expressed intracellularly. Briefly, RNA is isolated from the B cells of an immunised animal, for example from the spleen of an immunised mouse, and PCR primers used to amplify VH and VL cDNA selectively from the RNA pool. The VH and VL sequences thus obtained are joined to make scFv antibodies. PCR primer sequences may be based on published VH and VL sequences.

Peptidomimetics

Whilst numerous strategies to improve the pharmaceutical properties of peptides found to exert biological effects are known in the art including, for example, amide bond replacements, incorporation of non-peptide moieties, peptide small molecule conjugates or backbone cyclisation, the optimisation of pharmacological properties for particular peptides still presents those involved in the optimisation of such pharmaceutical agents with considerable challenges.

Peptides of and for use in the present invention may be modified such that they comprise amide bond replacement, incorporation of non peptide moieties, or backbone cyclisation. Suitably if cysteine is present the thiol of this residue is capped to prevent damage of the free sulphate group. Suitably a peptide of and for use in the present invention may be modified from the natural sequence to protect the peptides from protease attack.

Suitably a peptide of and for use in the present invention may be further modified using at least one of C and/or N-terminal capping, and/or cysteine residue capping. Suitably a peptide of and for use in the present invention may be capped at the N terminal residue with an acetyl group.

Suitably a peptide of and for use in the present invention may be capped at the C terminal with an amide group. Suitably the thiol groups of cysteines are capped with acetamido methyl groups.

Pharmaceutical Compositions

As described above, the present invention compounds which allosterically modulate beta1 integrin such that is assumes an intermediate affinity state. Pharmaceutical compositions for use in accordance with the present invention may comprise, in addition to active ingredient (i.e. an allosteric modulator of beta1 integrin which induces the beta1 integrin to assume an intermediate affinity state), a pharmaceutically acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be, for example, oral, intravenous, intranasal or via oral or nasal inhalation.

Dose

The modulatory compounds of the present invention are preferably administered to an individual in a "therapeutically effective amount", this being sufficient to show benefit to the individual. The actual amount administered, and rate and time-course of administration, will depend on the nature and severity of the condition being treated.

Prescription of treatment, e.g. decisions on dosage etc, is ultimately within the responsibility and at the discretion of general practitioners, physicians or other medical doctors, and typically takes account of the disorder to be treated, the condition of the individual patient, the site of delivery, the method of administration and other factors known to practitioners. The optimal dose can be determined by physicians based on a number of parameters including, for example, age, sex, weight, severity of the condition being treated, the active ingredient being administered and the route of administration.

Small Molecules

In various further aspects, the present invention relates to screening and assay methods for use in identifying compounds which act as allosteric modulators of beta 1 integrin activity. Certain further aspects extend to the compounds identified thereby, wherein said binding compounds have affinity and binding specificity for the epitope of the invention.

A substance identified an allosteric modulator of beta 1 integrin may be a peptide or may be non-peptide in nature, for example a peptidomimetic as described hereinbefore. However, non-peptide "small molecules" are often preferred for many in-vivo pharmaceutical uses. Accordingly, a mimetic or mimic of a compound which acts as an allosteric modulator of beta 1 integrin for use in the present invention may be designed for pharmaceutical uses.

The designing of mimetics to a known pharmaceutically active compound is a known approach to the development of pharmaceuticals based on a "lead" compound. This might be desirable where the active compound is difficult or expensive to synthesise, or where it is unsuitable for a particular method of administration. For example, peptides are not well suited as active agents for oral compositions and administration as they are degraded by proteases present in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, for example by substituting each amino acid residue in turn. These parts or residues constituting the active region of the compound are known as its "pharmacophore".

Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

In a variant of this approach, the three-dimensional structure of beta 1 integrin extracellular domain, or a compound which binds thereto, and which acts as an allosteric modulator is modelled. This can be especially useful where the ligand and/or binding partner change conformation on binding, allowing the model to take account of the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in-vivo or clinical testing.

In certain embodiments, the mimetic binding compound may be a natural or synthetic chemical compound used in drug screening programmes. Extracts of plants which contain several characterised or uncharacterised components may also be used.

A candidate binding compound which has affinity and binding specificity to beta 1 integrin may be isolated and/or purified, manufactured and/or used to modulate beta 1 integrin allosteric activity.

In yet further aspects, the invention extends to the use of combinatorial library technology (Schultz, J S (1996) Biotechnol. Prog. 12:729-743) which provides an efficient way of testing a potentially vast number of different substances for ability their ability to bind to an epitope or to modulate the activity of a ligand which binds to an epitope. Prior to, or as well as, being screened for modulation of activity, test substances may be screened for ability to interact with the polypeptide, e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trail and error depending upon the type of compound used. Typically, from about 0.01 to 100 nM concentrations of inhibitor compound may be used, for example from 0.1 to 10 nM. Greater concentrations may be used when a peptide is the test substance.

Combination Medicaments

The present invention extends to combinational therapies wherein compositions or methods relates to the administration of an allosteric modulator of beta 1 integrin according to the invention, which is administered to a subject in combination with at least one further therapeutic compound which serves to, for example, suppress the immune response which mediates tissue damage or injury.

Typically the primary and secondary therapeutic compositions are given contemporaneously. In certain embodiments, the primary therapeutic composition (i.e. the beta 1 integrin allosteric modulator) and the secondary therapeutic compounds are administered simultaneously. In certain further embodiments, they are administered sequentially.

Treatment/Therapy

The term 'treatment' is used herein to refer to any regime that can benefit a human or non-human animal. The treatment may be in respect of an existing condition or may be prophylactic (preventative treatment). Treatment may include curative, alleviation or prophylactic effects.

More specifically, reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

Administration

The allosteric modulatory compound of the present invention, such as an antibody or protein may be administered alone but will preferably be administered as a pharmaceutical composition, which will generally comprise a suitable pharmaceutical excipient, diluent or carrier selected depending on the intended route of administration. The allosteric modulator may be administered to a patient in need of treatment via any suitable route.

Routes of administration may include; parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebuliser or inhaler, or by an implant.

The composition may also be administered via microspheres, liposomes, other microparticulate delivery systems or sustained release formulations placed in certain tissues including blood. Suitable examples of sustained release carriers include semi-permeable polymer matrices in the form of shared articles, e.g. suppositories or microcapsules.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7 the entire disclosures of which is herein incorporated by reference.

Mimetics

A substance identified as an allosteric modulator of beta1 integrin may be peptide or non-peptide in nature. Non-peptide "small molecules" are often preferred for many in vivo pharmaceutical uses. Accordingly, a mimetic or mimic of the substance (particularly is a peptide) may be designed for pharmaceutical uses. The designing of mimetics to a known pharmaceutically active compound is a known approach to the development of pharmaceuticals based on a "lead" compound. This might be desirable where the active compound is difficult or expensive to synthesise of where it is unsuitable for a particular method of administration, e.g. peptides are not well suited as active agents for oral compositions as they tend to quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used I this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the led compound. The mimetic or mimetics found by this approach can then be screened to see whether they have the target property, or to what extent they exhibit it. Further optimisation or modification can then be carried out to arrive at one or more final mimetics for in vivo or clinical testing.

Mimetics of substances identified as having ability to modulate the confirmation of beta1 integrin are included within the scope of the present invention. A polypeptide, peptide or substance which can modulate the confirmation of beta1 integrin according to the present invention may be provided in a kit, e.g. sealed in a suitable container which protects its contents from the external environment. Such a kit may include instructions for use.

EXAMPLES

Example 1

Allosteric Modulation of Beta1 Integrin Function Reverses Functional Impairment and Lung Injury in a Mouse Model of Emphysema

Chronic Obstructive Pulmonary Disease (COPD) is characterised by poorly reversible and progressive airflow limitation associated with chronic bronchitis and emphysema. There are no effective treatments for emphysema to halt, slow or reverse the disease.

There is also limited information on how the lung is remodeled in emphysema. The extracellular matrix (ECM) interacts with integrins and modifies their function. In turn, integrins are key regulators of the ECM. Integrins bind metalloproteinases (MMPs), these being key enzymes in ECM homeostasis, and thus affects their activation state.

Excision of beta1 integrin gene in cardiac myocytes resulted in postnatal cardiac fibrosis, depressed cardiac function and increased myocardial glucose metabolism leading to spontaneous heart failure. Conditional deletion of beta1 integrin in the intestinal epithelium of mice causes a significant increase in epithelial proliferation without affecting cell adhesion.

Although transgenic approaches have highlighted the crucial role for beta1 integrin, they do not elucidate more subtle functions, such as those controlled by avidity regulation.

Materials and Methods

PPE-induced air space enlargement model in mice

Female C57/BL6 mice (6-8 weeks old) were instilled intra-tracheally with porcine pancreatic elastase as detailed before. At day 14 or 21, mice were treated intra-tracheally with the anti-integrin antibody JB1a at 3 mg/kg in sterile PBS. The dose chosen is equivalent to the dose of clinically used antibodies against $\alpha_4\beta_1$ integrin (Miller D H, et al. 2003). Control group was instilled initially with PBS and at day 14 or 21 with PBS. For the group treated at day 14, the animals were terminated at day 21 as follows: The animals were anaesthetised using sodium pentobarbitone (45 mg/kg), paralysed using pancuronium bromide (0.8 mg/kg) and tracheostomised and ventilated using a small animal ventilator (Flexivent, SCIREQ, Montreal) at 8 ml/kg and a rate of 150 breaths/minute and positive end expiratory pressures (PEEP) of 3.5 cm $H_2O$.

The pressure-volume curve was obtained during inflation and deflation in a stepwise manner by applying volume perturbation incrementally during 16 seconds. The pressure signal was recorded and the pressure-volume (P-V) curve calculated from the plateau of each step. The constant K was obtained using the Salazar-Knowles equation and reflects the curvature of the upper portion of the deflation P-V curve. Quasi-static elastance reflects the static elastic recoil pressure of the lungs at a given lung volume. It was obtained by calculating the slope of the linear part of P-V curve.

After the measurements, the animals were sacrificed and bronchoalveolar lavage collected. The bronchoalveolar lavage was centrifuged at 2000 rpm for 10 minutes and the supernatants lyophilised and analysed for metalloproteinase-12 (clone M19, polyclonal goat IgG, Santa Cruz) by Western blotting.

Histochemistry

The lungs were removed and formalin-fixed at a pressure of 25 cm $H_2O$, paraffin-embedded and sectioned at 4 µm thickness. Sagittal sections were used from each animal for histological and immunohistochemical assessment of damage, and morphometric analysis (mean linear intercept, Lm). Images from 10 fields per section were digitised using Image-Pro plus (version 5.1) and micropublisher 3.3 RTV camera connected to a Zeiss axioskope with 10× objective. The field size was 0.83 µm×0.63 µm. Mean linear intercept was calculated from each field (horizontal and vertical) by dividing the length of the line by the number of alveolar intercepts.

Gordon and Sweet's Reticulin stain was performed on 3 µm deparaffinised sections as a method of visualising collagen distribution in both injured and vehicle-treated lung. Briefly, sections were oxidised with 0.5% potassium permanganate, bleached with 1% oxalic acid, and treated with 2.5% ammonium iron (III) sulphate and a 5% silver nitrate/1.5% sodium hydroxide solution prior to reduction with 10% unbuffered formaldehyde. Visualisation of reticulin fibres was accomplished via treatment with 0.1% sodium chloroaurate and 3% sodium thiosulphate solutions. Sections were counterstained with neutral red prior to mounting.

Image Processing and Stereological Analysis

Colour images of 3 µm reticulin-stained sections were subjected to automated image processing methods developed in-house using Image Pro Plus (Media Cybernetics). Briefly, a greyscale image representing the green channel (which shows the highest differentiation from background) was obtained by splitting the RGB channels. Sobel edge detection operators, dilation-erosion and erosion-dilation algorithms were used to enhance the image and to remove 'salt and pepper' noise. An area of interest measuring 200 µm×200 µm was overlaid over a digitally-captured image of a reticulin-stained section and only events completely inside the frame or intersecting the two inclusion edges of the frame's left and lower aspects (South-West) were included. Events intersecting the right and upper aspects (North-East) of the frame were excluded, as were blood vessels other than the capillaries of the alveolus. 2D objects that were counted using this method included alveolar septal junctions, free septal ends, and contiguous airspaces. A total of 15 non-overlapping frames were included per section as this was sufficient to achieve a running mean. The mean number of events on sections obtained from vehicle-treated (n=5), PPE-treated (n=5), and JB1a-treated (n=5) mice were scored as a function of area (counts per 200 µm×200 µm field of view).

Immunohistochemistry

3 µm paraffin sections of lung were deparaffinised, rehydrated, and washed in water. For TTF-1 (clone 8G7G3/1, DAKO) immunohistochemistry, a microwave antigen retrieval method was used (3×5 minute 700 W microwave treatments, in 10 mM citrate buffer, pH 6.0). GATA-6 (H-92 rabbit polyclonal IgG, Santa Cruz) immunohistochemistry required proteinase K pretreatment (20 µg/ml, 20 minutes, 37° C.). Endogenous peroxidase activity was blocked with 3% hydrogen peroxide in water. Endogenous biotin was blocked with Avidin/Biotin Blocking Kit (Vector). Sections were blocked with either M.O.M IgG Blocking Reagent (Vector) or DAKO Protein Block Serum-Free (used for rabbit polyclonal antibodies) prior to incubation with primary antibody (diluted 1:50) overnight at 4° C. The following day, sections were washed 5 times in TBST (Tris-Buffered Saline pH 7.6, with 0.1% Tween 20) prior to incubation with biotinylated secondary antibody (30 minutes) and DAKO Strept-ABComplex/HRP (20 minutes). Immunohistochemical staining was visualised using DAB chromogen, a haematoxylin counterstain was used for sections other than those used to generate 3D reconstructions. Sections were washed, dehydrated and mounted in DPX. Negative controls omitted the primary antibody step.

3D Reconstructions 10 consecutive 3 μm sections were used to generate 3D reconstructions of tissue parenchyma. Odd (1, 3, 5 . . . ) sections were labelled with GATA-6 whilst even (2, 4, 6 . . . ) sections were labelled with TTF-1. Digitally captured images were obtained with a QCapture Pro imaging system and a brightfield microscope (Zeiss Axioskop, 20× objective lens) and were patched into larger images (3×3), which were interleaved to form their original order in an image stack prior to alignment using Adobe Photoshop 7.0.1. TIFF images were cropped, resized (6000×6000 pixels) and image stacks were imported into Amira 4.0 for isosurface rendering, which was accomplished at threshold values sufficient to detect either immunohistochemical label or tissue parenchyma. Isosurfaces were coloured either red (TTF-1), blue (parenchyma) or yellow (GATA-6) for enhanced visualisation.

Apoptosis Measurement

Terminal Deoxyribonucleotidyl Transferase (TdT)-Mediated dUTP Nick End Labelling (TUNEL) was assessed in sections using the Red ApopTag™ Kit (Chemicon). Data for the quantification of positively stained apoptotic nuclei was acquired using the x40 oil objective of a Zeiss 510 Axiovert confocal microscope system (Carl Zeiss Ltd, Welwyn Gardens City, Herts, UK). The stage-tiling utility was employed for the collection of 4×4 tiled images, equivalent to a total area of 0.921 mm×0.921 mm, imaged from a lung section of ~8 mm×8 mm (two tiles each from right and left lobes). Images of mainly alveolar tissue were constructed. The images were then converted to 8-bits grey scale and ImageJ was used to count total number of cells. TUNEL positive cells were counted manually.

F-actin Staining in 35 Day Mouse Lungs

Separate experiments were performed where lung tissue was fixed using fixed volume of 4% paraformaldehyde for 1 hour at 37° C. The tissue was then immersed in 40% sucrose in PBS overnight at 4° C. The lung tissue blocks were embedded into OCT and frozen. Cryostat sections (4 microns) were stained using Alexa-fluor phalloidin and TO-PRO3 (Molecular Probes). Images were acquired using Zeiss Axioskope using a x63 oil achroplan objective and analysed using LSM 5 Image software.

Caspase 3/7 Activity Measurements Using Human Mesenchyme and Epithelial Cell Co-culture In Vitro Adult human lung fibroblasts (CCD-8Lu) were seeded onto collagen I coated BioFlex 6 well plates at $0.5 \times 10^6$/well. The following day, NCI-H441 were seeded on top of the fibroblasts at the same density. NCI-H441 cells possess alveolar type II cell characteristics. Cells were starved with media containing 0.1% FCS. The plates were subjected to stretching at 0-5%, 0-10% or 2-10% sinusoidal stretch at 1 Hz for 6 hours. Control plates on plastic or bioflex plates without stretch were also included. PPE was added at 0.06 or 0.3 U/ml alone or in combination with JB1a (1 μg/ml) and ZVAD-fmk at 10 or 20 μM. At the end of the 6 hour period, the media was aspirated and caspase 3 activity assayed using Caspase-Glo™ 3/7 (Promega) according to the manufacturers' instructions. Separate experiments were performed at up to 6 hours of stretching where the cells were fixed with 4% paraformaldehyde and stained using Alexa-fluor phalloidin and TO-PRO3 (Molecular Probes). Images were acquired using Zeiss Axioskope using a x63 water achroplan objective and analysed using LSM 5 Image software.

In a separate set of experiments lung fibroblasts and epithelial cells were seeded onto 96 multi-well plates as described above. The cells were starved in media containing 0.1% FCS then in DMEM-glucose-free with 0.1% FCS for 45 minutes before treating with (i) PPE at 0.3 U/ml alone or (ii) PPE preceded by JB1a (1 μg/ml). At the end of the experiment, ATP levels were measured using a bioluminescent ATP kit (Perkin Elmer).

Human Lung Explant Culture and Human Lung Cell Isolation

Human lung tissue specimens were obtained (and approved by NHS ethics committee and with consent) and cultured as either 20-30 mg explant strips or cells. Alveolar epithelial cells were isolated as described before (Elbert et. al., 1999 and Murphy et al., 1999). The cells were then plated onto Transwells of 0.3 um pore size (Sigma) and maintained in culture using 1:1 DMEM/F12:Small airway growth media (Cambrex BioScience Wokingham Ltd.) containing 1% foetal calf serum. The remaining tissue was treated with DMEM containing 40% foetal calf serum to inactivate the digestive enzymes and then washed using HEPES buffer. To isolate fibroblasts and smooth muscle cell populations, the tissue was then incubated in DMEM containing 1 mg/ml collagenase, 0.5% trypsin and 200 U/g DNAsI and maintained at 5% in an $CO_2$ incubator. The cell suspension was washed as above and cells seeded on multiwell culture plates and maintained in DMEM containing 10% foetal calf serum.

Cultures were subjected to serum starving overnight in a medium containing 0.1% foetal calf serum. Some collagenase digested plated cells were co-cultured with isolated alveolar epithelial cells Transwells at the time of commencing the starvation.

Functional modifying antibody against beta1 integrin (Chemicon, clone JB1a, $IgG_1$; also commercially available as JB1A mouse anti-CD29 (Integrin beta-1 subunit) IgG monoclonal antibody, unconjugated, clone JB1a, Millipore, Catalogue number MAB1965) was added to the cultures at a concentration of 1.44 and 0.48 μg/ml. The beta1 integrin stimulatory antibody clone TS2/16 (IgG1) was also added at 0.9 μg/ml for 1 hour to demonstrate the specificity of the JB1a action. After antibody addition to the cells in culture, the medium was aspirated and the cell layer rinsed twice with ice-cold PBS. The media was aspirated and preserved after the addition of protease inhibitors at −80° C. In additional experiments, the effect of protein synthesis inhibition on beta1 integrin mediated proteoglycan increase was tested by pretreating the human lung derived cells with 25 μM cycloheximide. The effect of non-specific activation of metalloproteinases on beta1 integrin mediated proteoglycan increase was tested by pretreating the human lung derived cells with 0.5M APMA (aminophenylmercuric acetate). To investigate the involvement of selected metalloproteinases in initiating the response observed with beta1 integrin, specific neutralising antibodies for metalloproteinase-7 (1:1000, goat IgG, R&D systems) and metalloproteinase-9 (1:1000 of clone 6-6B, mouse IgG1, Oncogene Research Products) were used. A broad spectrum inhibitor of metalloproteinases was also used at 2.3 nM (metalloproteinase inhibitor III, Calbiochem).

SDS-PAGE was also used to separate the denatured proteoglycan and proteins from the tissue concentrated tissue culture supernatants. Perlecan antibody immunoreactive to non-degraded forms of perlecan was used (7B5, mouse IgG1, Zymed Laboratories). Metalloproteinase-1 (clone 41-1E5, IgG2a against amino acids 332-350 of human metalloproteinase-1), inactive metalloproteinase-9 (clone 7-11C, mouse IgG1) and TIMP1 (clone 7-6C1, mouse IgG1) antibodies were all derived from Oncogene Research Products.

Time-lapse Studies

Cells were cultured as described in methods at 50,000 cell/membrane onto collagen I Bioflex membranes using silicone gaskets of 10 mm diameter. Cells were starved with media containing 0.1% FCS and Syto 16 (Molecular Probes). The media was removed and Alexa-Fluor 647 labelled G-actin (100 μg/membrane) from rabbit was loaded using Influx (Molecular Probes). The cells were loaded with PhiPhiLux-G2D2 for visualisation of caspase activation (OncoImmune). The membrane was then mounted onto the StageFlexer (Flex-Cell), placed on the stage of an upright Leica-TCS-NT confocal microscope system (Leica Microsystems GmbH, Heidelberg, Germany) and subjected to 2-10% cyclic stretch at 1 Hz for up to 6 hours. Images were collected simultaneously from 3 channels at 1 minute intervals, using the x10 lens. The resulting time-lapse movies were collated and analysed with Imaris software (Bitplane AG, Switzerland). At various time points during the study, the membrane was held static while serial optical sections were acquired, the three fluorescent channels supplemented by the collection of the brightfield channel image.

Three-dimensional Confocal Microscopy

NCI-H441 cells and human lung fibroblasts were cultured as described above onto collagen I-coated glass cover slips at 20,000 cells within an area of 5 mm in diameter. The media was removed and Alexa-Fluor 647 labelled G-actin (30 μg/coverslip) from rabbit was loaded using Influx (Molecular Probes). The cells were loaded with PhiPhiLux-G2D2 for visualisation of caspase activation (OncoImmune) and FL-ganglioside 1 (GM1, Molecular probes) to visualise the plasma membrane. Images were collected through 4 separate channels (GM1: λ=488, caspase λ=568, actin: λ=647 nm and brightfield) using x63 water lens and Zeiss LSM510 CLSM microscope. The resulting images were analysed with Imaris software (Bitplane AG, Switzerland). Three-dimensional images were reconstructed.

Caveolin-1 Extraction and Analyses

NCI-H441 cells and human lung fibroblasts were cultured as described above. Media was changed prior to the experiment to 0.1% FCS containing media. Vehicle, PPE (0.3 U/ml) or PPE in the presence of JB1a (1 μg/ml) containing media was added onto the cells for 2 hours. Cells were extracted using lysis buffer composed of 50 mM Tris-HCl (pH 7.5), 1 mM EDTA, 1 mM $Na_3VO_4$ containing 1% Triton X-100 and protease inhibitors (Roche) for 1 hour at 4° C. and sheared repeatedly using 22 G needle on ice. Total protein was quantified using Bradford's assay method (BioRad). The extracts (1 ml) were mixed with equal volume of 85% w/v sucrose in extraction buffer without Triton X-100 and layered with 2 ml of 35% w/v sucrose in buffer and then 1 ml of 5% w/v sucrose in buffer. The gradients were prepared at 4° C. The gradients were then centrifuged at 38,000 rpm for 16 hours at 4° C. Fractions were collected from the top (0.4 ml fractions) and separated onto 13% SDS-PAGE and transferred onto nitrocellulose membranes then probed for β1 integrin using JB1a (Chemicon), caveolin-1 (BD Biosciences), phosphorylated caveolin-1 (Cell Biosciences) and talin (Sigma-Aldrich), and developed with HRP-conjugated secondary antibodies using the ECL-plus chemiluminescence system (Amersham Biosciences).

Sphingomyelinase Activity Measurements In Vivo and In Vitro

Adult human lung fibroblasts (CCD-8Lu) were seeded onto collagen I coated BioFlex 6 well plates at $0.5 \times 10^6$/well. The following day, NCI-H441 were seeded on top of the fibroblasts at the same density. Cells were starved with media containing 0.1% FCS. The plates were subjected to stretching at 2-10% sinusoidal stretch at 1 Hz for 5, 10, 15 and 30 minutes. PPE was added at 0.3 U/ml alone or in combination with JB1a (2 μg/ml). At the end of stimulation, the media was aspirated and sphingomyelinase was were extracted using 200 ul buffer composed of 20 mM HEPES, 1 mM sodium fluoride, 0.1 mM sodium molybdate, EDTA-free protease inhibitors (Roche) and 0.2% Triton x-100 (pH 7.4). Sphingomylinase activity was assayed using the amplex red assay (Molecular Probes) according to manufacturer's instructions.

In separate in vivo experiments, mouse lung tissue (35 day group) was frozen using liquid nitrogen. The tissue was then sliced at 40 um thick section using a cryostat and extracted using the above mentioned sphingomyelinase buffer for 1 hour. Sphingomyelinase activity was assayed over time using the amplex red assay (Molecular Probes). The activity was calculated according to wet tissue weight.

Lipid Raft Formation in Vitro

In a separate set of experiments lung fibroblasts and epithelial cells were seeded onto collagen I-coated glass coverslips at 20,000 cells within an area of 5 mm in diameter. The media was removed and the dye laurdan was added. The lipophilic probe, 2-dimethylamino-6-lauroyl-naphthalene or Laurdan (Molecular Weight 353.54, 100 mg or 0.28 mmoles, Aldrich-Sigma), was prepared in DMSO (Sigma) to give a 6 mM stock solution (dissolve 100 mg in 47 ul). 1 ul of Laurdan stock solution was added per coverslip in the dark at 37° C., and incubated for 15 minutes.

Laurdan fluorescence was excited with a titanium-sapphire laser. Laurdan intensity images were recorded simultaneously with emission in the range of 400-460 nm and 470-530 nm for the two channels, respectively. The relative sensitivity of the two channels was verified by exposing control cells to 1 mg/ml methyl-beta-cyclodextrin for 1 hour to deplete lipid rafts Images were collected using x63 water lens and Zeiss LSM510 CLSM microscope. The resulting images were analysed with Imaris software (Bitplane AG, Switzerland). Three-dimensional images were reconstructed.

The excitation generalized polarization (GPex) spectra were derived from the following equation.

$$GPex = (I_{440} - I_{490})/(I_{440} + I_{490})$$

where $I_{440}$ and $I_{490}$ are the intensities at each excitation wavelength, from 320 to 410 nm, using a fixed emission of 440 and 490 nm, respectively.

Electric Cell-Substrate Impedance Sensing (ECIS) Measurements

Epithelial-mesenchymal human lung cell cultures were grown on collagen I pre-coated ECIS-arrays (model 8W10E, Applied BioPhysics, Troy, N.Y.), which consist of 8 wells with 10 electrodes deposited on the bottom of each well (Applied-Biophysics, Inc. Troy, N.Y.). ECIS-measurements were performed via the ECIS™ Model 1600 (Applied BioPhysics, Troy, N.Y.). Both data acquisition and processing were performed using the ECIS Data Analysis Software supplied by Applied Biophysics (Troy, N.Y.).

Media (DMEM/F12: MEM at 1:1 containing 0.1 foetal bovine serum) was added and a baseline was established for 2 hours. The media was then changed to one containing: PBS, porcine pancreatic elastase (0.3 U/ml), JB1a (2 ug/ml) or a combination of elastase and JB1a monoclonal antibody. ECIS measurements were carried out for at least 4 hours at 37° C. and 5% $CO_2$ at 30 Hz and 1 recording/minute.

ECIS Instrumentation

The sensing area within a single well of the 8-well ECIS arrays consists of 10 active working electrodes in parallel that are distributed over the bottom of the well, and a counter electrode much bigger in surface area. A non-invasive alternating current (<1 μA) is applied to the electrodes which are electrically connected via the electrolytes of the cell culture medium above the cells. The ECIS device reads the associated voltage drop across the system (in-phase with the current) and determines the electrical resistance of the cell-covered electrodes. Previous studies have indicated that the resistance measured is most sensitive to monitor the establishment of cell-cell junctions as a function of time.

Experimental Protocols and Results

The experimentation first considered whether beta1 integrin allosteric modulation altered the ECM. This experimentation focused on perlecan because of its known role in basement membrane integrity.

In a co-culture of primary human alveolar epithelial cells with lung interstitial cells, the anti-beta1 integrin antibody JB1a caused an increase in perlecan (FIG. 5(a)); a change that persisted for 24 hours and was partially sensitive to pre-treatment with cycloheximide and the non-specific MMPs activator aminophenylmercuric acetate (APMA). Treatment with neutralising anti-MMPs 7 and 9 antibodies failed to produce a similar increase in perlecan expression. The changes in perlecan in response to JB1a were accompanied by an increase in tissue inhibitors of metalloproteinase-1 (TIMP1) initially (FIG. 5(b)) and pro-MMP-9 subsequently (FIG. 5(c)).

The results therefore indicate that JB1a-induced changes in proteoglycan are not solely due to alteration in the MMP/TIMP balance. Similar responses in human lung explants and the alveolar cell line, NCI-H441, were also obtained and were specific to JB1a treatment (data not shown). As controls, it was shown that the anti-beta1 integrin antibody TS2/16, which binds the 207-218 amino acid sequence, and 6S6 clone, which binds a discontinuous unmapped epitope, had no effect on proteoglycans.

In order to investigate whether allosteric modulation of beta1 integrin was of therapeutic value in a model of emphysema, mice were treated with the anti beta1 integrin monoclonal antibody, JB1a, or vehicle, either once on day 14 (21 day group, 21d) or on days 21 and 28 (35 day group, 35d) after elastase instillation and the achievement of maximal air space enlargement on the basis of a pilot time course study and previous reports. Diseases such as emphysema, where remodelling is a key feature were assessed. Both JB1a and 6S6 clones bind beta1 integrin in mouse tissues (U. Cavallaro, et al., Nat. Cell Biol. 3, 650-657 (2001)). An additional group receiving elastase and the isotype control IgG1, MOPC21, was performed and showed no reversal of elastase-induced structural damage (data not shown). The clone 6S6 did not induce repair in vivo (data not shown).

A marked leftward shift in the respiratory pressure-volume curve (PV) in response to elastase was observed, and there was a progressive increase in the PV shape exponential constant, k, particularly in the 35 day group (FIG. 1(a)-(b)). This shift was reversed by JB1a treatment (FIG. 1(a)-(b), for 35 day data, 21 day data not shown). Furthermore, the effect of elastase treatment on the peak pressures and quasi-static elastance derived from the PV curves were significantly reversed by JB1a treatment (FIGS. 1(c) and 1(d)).

Lung morphometry demonstrated that JB1a treatment also reversed elastase-induced air space enlargement (FIGS. 2(a) and 2(b)). The explanation for the discrepancy between the functional and structural differences of the 21 day and 35 day treatment groups reflects the presence of inflammation, noted histologically only in the 21 day group. The functional reversal was accompanied by reversal in elastase-induced damage to elastic fibres (data not shown).

To study the effect of JB1a on regeneration of lung and alveolar septation, we used image analysis of histological sections from the 21 day group to determine the number of contiguous airspaces, septal junctions and septal ends (FIGS. 2(c)-(e), FIG. 6 for method). Elastase pre-treatment decreased the number of contiguous airspaces and was reversible by JB1a treatment (FIG. 2(c)). In addition, elastase pre-treatment caused a decrease in the number of septal junctions which was partially reversed by JB1a (FIG. 2(d)). No change was seen in the number of septal ends (FIG. 2(e)). Using 3D image reconstructions of expression pattern of TTF-1 and GATA-6 in 21 day group animals, two transcription factors which control septation 13; 14, we found that GATA-6 expression increased following elastase pre-treatment (FIG. 3(a)). Treatment with JB1a induced increased numbers of TTF-1 expressing cells, and attenuated the GATA-6 upregulation associated with elastase-injury.

Allosteric modulation of beta1 integrin affects both mitosis and cell death. Since cell death has been implicated in COPD progression, the prevalence of TUNEL positive cells in mouse lung at days 21 and 35 following injury with or without JB1a treatment was evaluated. There was a significant increase in TUNEL positive cells in the lung both at 21 days and 35 days post-elastase instillation: this was significantly reduced by subsequent treatment with JB1a (FIGS. 3(b) and (c)).

Figure 4:
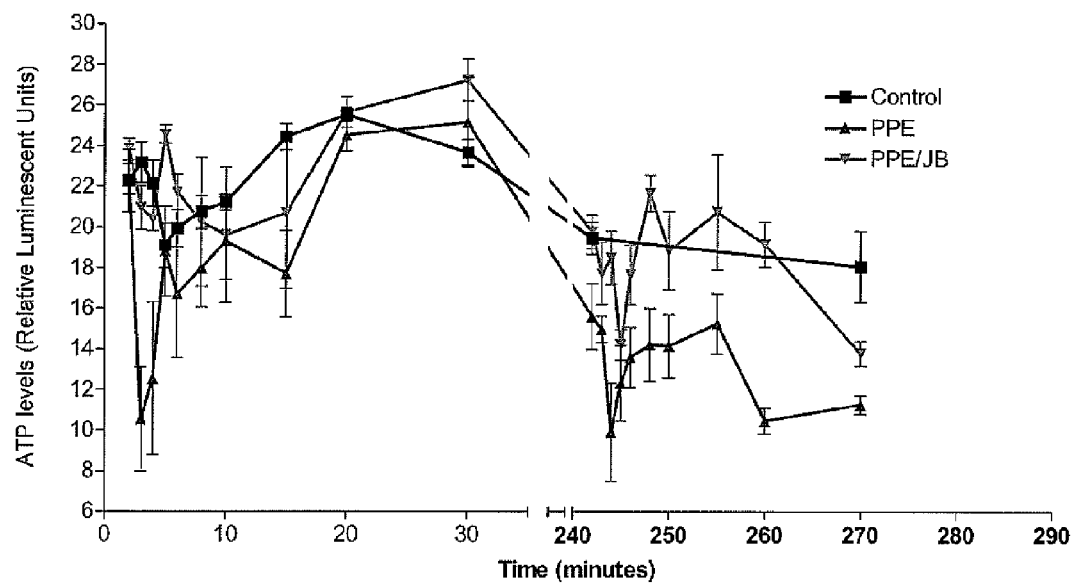
FIG. 4 shows the effects of PPE-induced injury and JB1a treatment on caspase levels (FIG. 4(a)), F-actin (FIG. 4(b)) and ATP levels (FIG. 4(c)) in-vitro using human lung co-culture during with mechanical stretch for 6 hours. The effects of PPE-induced injury alone and in the presence of JB1a treatment on beta1 integrin (FIG. 4(d)), caveolin-1 FIG. 4(e)) and phosphorylated caveolin-1 levels (FIG. 4(f)) in membrane fractions. Representative blots from n=4. Loading controlled by total amount of protein before gradient separation.
Figure 6:
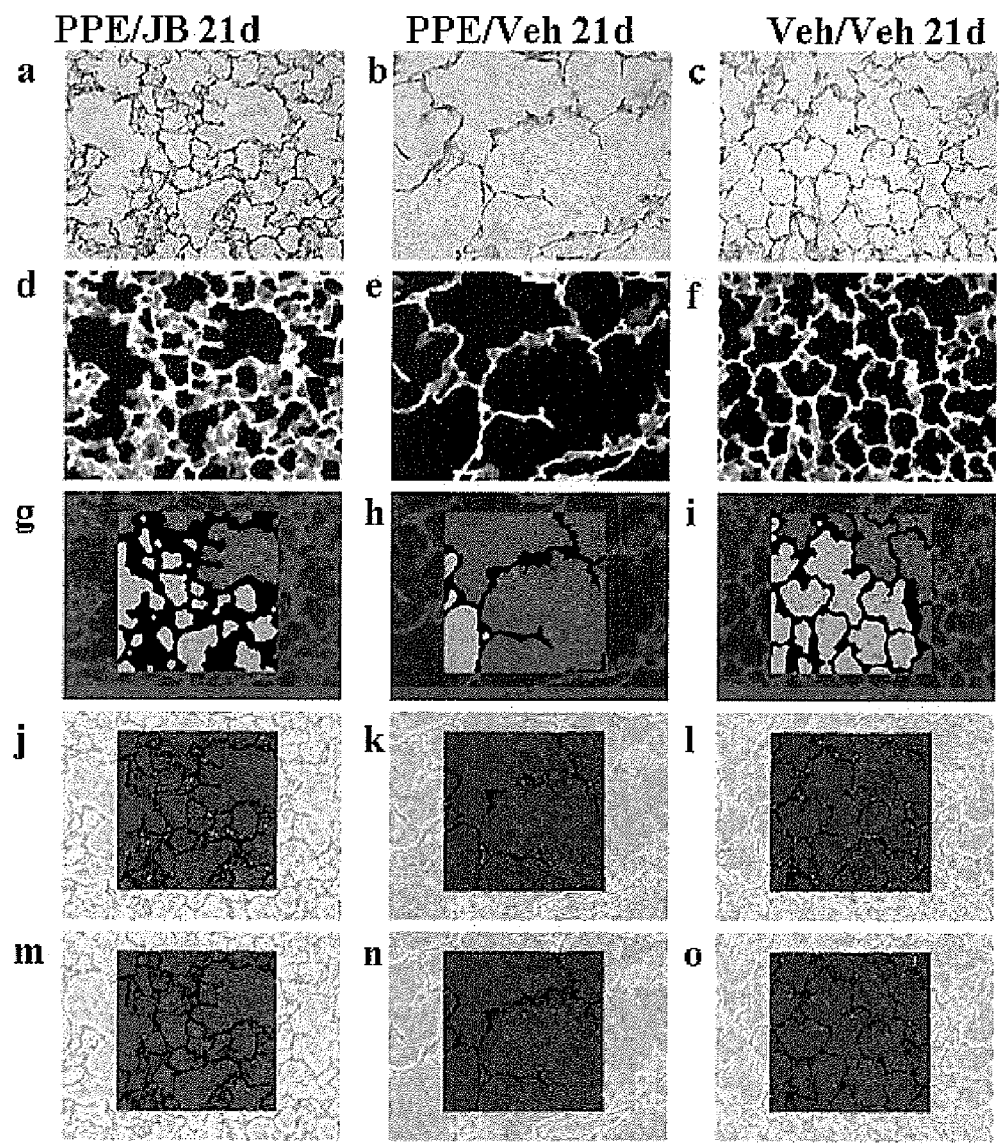
FIG. 6 shows automated image processing of the septal junctions, septal ends, and contiguous airspaces in the pulmonary acinus in the 21 day group.
Figure 9:
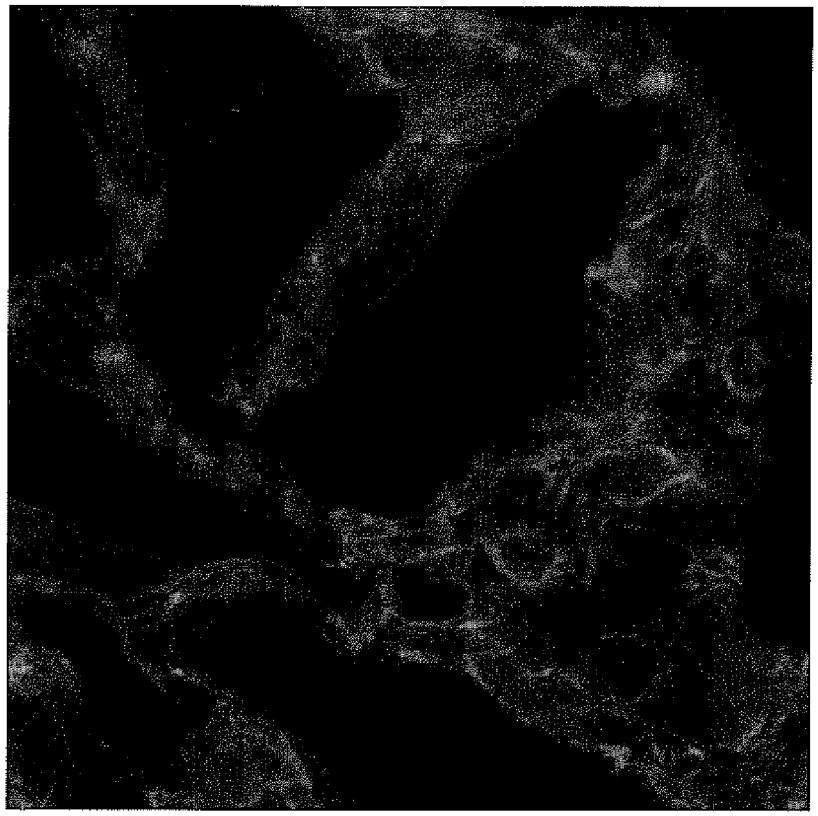
FIG. 9 shows 3D reconstruction of images of in-vivo mouse lung after injury using elastase (b, c) (0.2 U/g body weight) demonstrating the formation of F-actin (green) after 35 days and its inhibition by JB1a (d, e)(3 mg/kg on days 21 and 28). (a: vehicle instilled animals). Each figure is from a separate animal.

Elastase can induce apoptosis of epithelial cells secondary to altered attachment (anoikis), accompanied by alteration in mitochondrial permeability and caspase activation. In a co-culture of adult human lung fibroblasts overlayered with NCI-H441 cells, under cyclic mechanical stimulation, we showed that elastase treatment caused a significant increase in caspase 3 and 7 activity. Addition of JB1a to the cultures inhibited elastase-induced caspase activation in a similar fashion to the broad spectrum caspase inhibitor, ZVAD-fmk (FIG. 4(a)). Furthermore, it was found that elastase treatment increased F-actin aggregates, changes inhibited by both JB1a and ZVAD-fmk (FIG. 4(b)). In time-lapse studies 3D reconstructions, it was demonstrated that the increase in F-actin formation during the course of elastase-induced injury which was followed by activation of caspase 3 and 7 (FIGS. 7(a)-(c) and 8). These findings are supportive of the notion that cytomechanics determine cell fate and effect repair.

Formation of F-actin from monomeric G-actin is energy dependent and under ATP depletion conditions, there is a net conversion of monomeric G-actin to polymeric F-actin. We measured ATP levels in co-cultures in response to elastase and JB1a. Elastase reduced the levels of ATP, a response inhibited by JB1a (FIG. 4(c)).

Beta1 integrin-mediated adhesion has been shown to regulate cholesterol-rich membrane microdomain internalisation mediated by phospho-caveolin-1. In co-cultures, elastase significantly reduced cell membrane-associated beta1 integrin levels and induced phosphorylation of caveolin-1 within two hours; changes inhibited by JB1a (FIG. 4(d)).

It has previously been shown that the administration of beta4 thymosin, an actin-sequestering protein, promoted cardiac repair after ischemia-reperfusion injury. Changes in actin dynamics also affect mitochondrial function and the release of reactive oxygen species eliciting death signals. Additionally, gene disruption of caveolin-1, which is known to be involved in integrin clustering and activation, results in pulmonary fibrosis and impairment in liver regeneration after partial hepatectomy which was reversible by treatment with glucose, indicating the probable importance of energy preservation.

In conclusion, it is suggested that elastase-induced progressive damage is partly due to anoikis resulting from an increase in cytoskeletal tension caused by increased actin polymerisation, rendering the cell rigid and susceptible to physiological forces. Without being bound by theory, the inventors predicts that the allosteric modulation could effect alteration in the receptor focal density leading to changes in cytoskeletal organisation and cell membrane composition hence affecting cell behaviour and fate.

Conclusions

The present experimentation has identified a novel cellular mechanism for mediating repair in cases of lung injury caused by emphysema. The surprising advances in understanding made by the inventors in relation to the role of beta1 integrin in emphysema and how altering its allostery facilitates structural and functional repair have elucidated a novel mechanism of cellular injury in emphysema to which a therapeutic approach for treatment can be applied.

Significant components of the mechanism of action of beta1 integrin-mediated repair include the following:

A. The role of the actin cytoskeleton in beta1 integrin mediated repair in lung emphysema and in particular (i) the in-vitro findings which show an alteration in actin polymerisation, and (ii) the observation that changes in receptor movement can cause membrane disruption thus wounding the cell membrane. Integrin engagement in addition to calcium influx can cause a wide range of responses one of which is initiation of actin polymerisation to form a "sealant" to be filled later with membrane microdomains. It has been reported that the induction of calcium oscillations rather than the net concentration protects from injury in adult tissue; a feature present in the developing tissues. The present experimentation has shown a similar phenomenon in ATP oscillation in two independent injury models. This part identifies the role of allosteric changes in beta1 integrin and its effects on cellular mechanics and cytoskeletal alterations in repair after injury in the lung.

B. The role of receptor clustering and/or altered diffusibility in injury and beta1 integrin repair. Recently, beta1 integrin-mediated adhesion was shown to regulate cholesterol-rich membrane microdomain internalisation mediated by phospho-caveolin-1. Gene disruption of caveolin-1 in mice resulted in pulmonary fibrosis as well as cytoskeletal changes and inhibition of focal adhesion kinases in-vitro. It has also been shown that in these mice there is impairment in liver regeneration after partial hepatectomy which was reversible by treatment with glucose. Experimentation was conducted in which epithelial-mesenchymal co-cultures were exposed to vehicle, elastase alone or in the presence of allosteric modifying anti-beta1 integrin antibody. Elastase induced caveolin-1 phosphorylation and this effect was inhibited by allosteric modulation of beta1 integrin. Furthermore, elastase resulted in a significant reduction in membrane associated beta1 integrin levels in two hours. Association of beta1 integrin with lipid-rich domains 3 hours after the addition of elastase was not detected. However, the presence of phospho-caveolin-1 in the heavy fractions of extracts from the elastase-injured cultures was detected. The addition of allosteric modifying anti-beta1 integrin antibody inhibited the elastase-induced changes.

Sphingomyelin is a ubiquitouse lipid of cell membranes with the plasma membrane containing 70-90% of total cellular content. Sphingomyelin is hydrolysed by sphingomyelinases (SMase) into ceramide and phosphocholine. Ceramide is degraded into sphingosine and fatty acid by ceramidases. To date there are five SMase isoforms; alkaline SMase, lysosomal acidic SMase (aSMase), secreted $Zn^{2+}$-dependent acidic SMase, membrane-bound $Mg^{2+}$-dependent SMase (nSMase), and cytosolic $Mg^{2+}$-independent SMase. The SMase isoforms differ in their subcellular localization, tissue specificity, and enzymatic properties. The role of aSMase and ceramide synthesis in platelet-activating factor, endotoxin or acid instillation induced acute lung injury.

Ceramide is a lipid "second messenger" molecules involved in the regulation of cell differentiation and TNF and Fas-induced apoptosis as well as stress-induced apoptosis. The alteration in composition of lipid raft transforms into a gel-like state and thus alters its viscosity and diffusion properties rendering it more rigid. Changing the tether in lipid rafts leads to further change in ceramide content and fusion of ceramide microdomains to form rigid ceramide-enriched membrane platforms.

Changes in the activity of SMase could also be altered in the mitochondria leading to increase ceramide synthesis. This could cause changes in the membrane permeability which could effect a change in mitochondrial membrane potential, volume and leakage of molecules such as cytochrome C. Time-lapse confocal microscopy studies of human epithelial/mesenchymal co-cultures using mitochondrial dyes and the membrane potential indicator dye JC-1 were performed. It was observed that elastase affected mitochondrial membrane potential and caused mitochondrial swelling. Additional experiments using fluorescent mitochondrial dye revealed signs of swelling in response to elastase injury which was reversed by treatment with the anti-beta1 integrin antibody, JB1a. This demonstrates that beta1 integrin allosteric modulation induced repair in lung injury as a result of inhibiting membrane disruption due to clustering of cell surface receptors and/or altered membrane composition (due to increase ceramide) rendering it biophysically rigid.

C. The effect of changes in the actin cytoskeleton in emphysematous injury on transcription and translation as determined by (i) the presence of polymerised cytoskeleton scaffolding can affect the half-life of intracellular molecules such as mRNA. Reports have linked alteration in cytoskeleton-associated mRNA pool secondary to differentiation or integrin binding. An investigation of the downstream effectors of beta1 integrin in allosteric modification-induced repair in the lung is in preparation. The potential for such experiments are the identification of effectors which could provide additional specific targets in repair and regeneration.

The effect of beta1 integrin-induced repair after injury using therapeutic antibodies in vitro and in vivo on cytoskeleton-associated mRNA done using microarray technology (Affymetrix). Human co-cultures and in vivo lung tissue subjected to injury alone or injury and repair via beta1 integrin allosteric modification then subjected to selective extraction buffers (Cytoskeleton, Inc.) followed by RNA extraction as detailed before (A. Brock, S. Huang, D. E. Ingber, *BMC. Cell Biol.* 4, 6 (2003)). All procedures will include the appropriate controls. The RNA will be reverse transcribed and labelled before hybridising it on microarrays. RT-PCR of identifiable genes will be done subsequently for confirmation. These experiments will identify effector gene translation downstream of beta1 integrin induced repair after injury.

This will be further determined by (ii) the effect beta1 integrin-mediated repair effect on nuclear actin and its effect on chromatin. Actin plays a direct role in gene transcription. It has been found to associate with components of ATP-dependent chromatin remodelling complexes, RNP particles, and the three RNA polymerases in the cell nucleus. Various actin subtypes have been reported to be in the nucleus such as β-actin monomeric, oligomeric, and filamentous). Experiment will focus on determining the effect beta1 integrin mediated repair after elastase-induced injury in vitro using human and mouse co-cultures on the association of nuclear actin with chromatin. This will be done using promoter chromatin immunoprecipitation-on-chip (ChIP-on-chip). The immunoprecipitation will be conducted using antibodies against actin and actin-binding proteins (Abcam). Further experiments using the wild type and mutant beta1 integrin expressing cells will be conducted. This will demonstrate further effector genes downstream of beta1 integrin and their involvement in repair.

Figure 11:
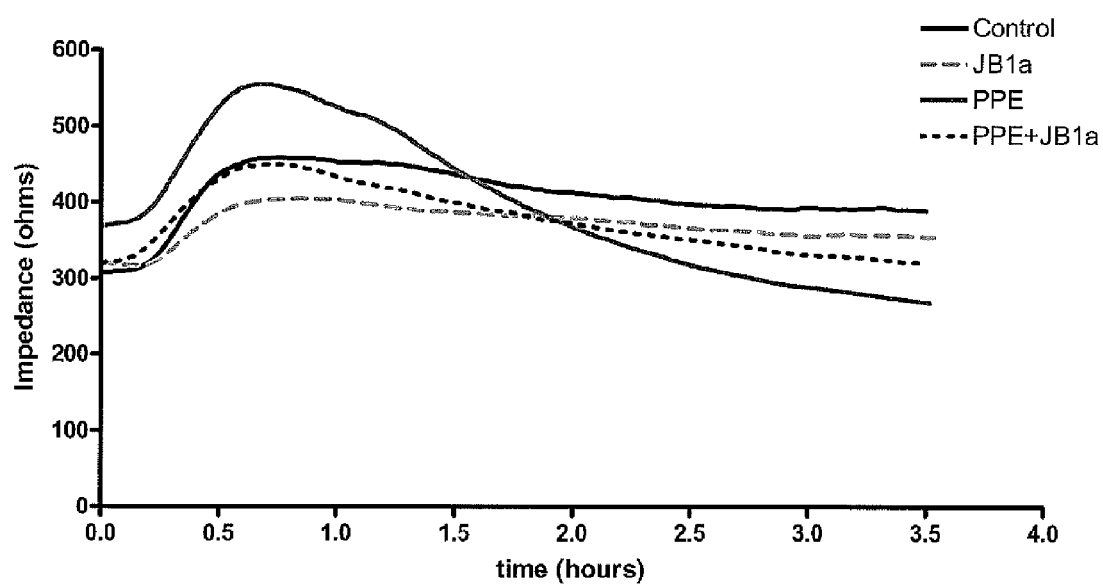
FIG. 11 shows the effect of elastase-induced injury (0.6 U/ml) on raft formation using laurdan in human lung co-culture and its inhibition by JB1a (2 ug/ml). The intensity of laurdan emission at 488 nm indicates increase in lipid rafts after elastase-induced injury. Methyl-beta-cyclodextrin was used as a control as it depletes cholesterol thus reducing the intensity of laurdan at 488 nm.

In vitro experiments using epithelial-mesenchymal cultures to measure the activity of neutral sphingomyelinase have demonstrated that there was a transient increase in activity in the presence of elastase which was blocked by JB1a (FIG. 10). Furthermore, there was an increase in lipid rafts in the presence of elastase; an effect reversed by JB1a (FIG. 11).

Changes in the activity of SMase could also be altered in the mitochondria leading to increase ceramide synthesis. This could cause changes in the membrane permeability.

Figure 12:
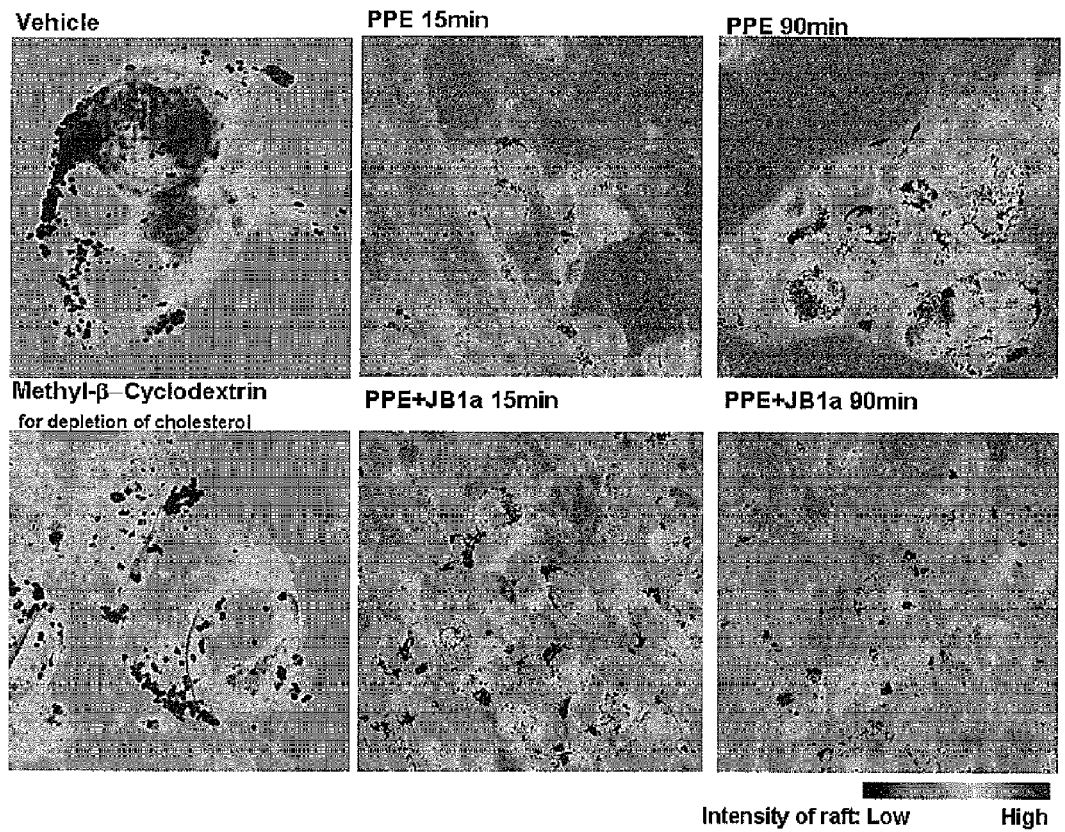
FIG. 12 shows the effect of elastase-induced injury (0.3 U/ml) on electrical impedance of human lung co-culture and its inhibition by JB1a (2 ug/ml). The experiment was repeated 3 times and each was done in duplicate. Each well had 8 sampling electrodes. The figure is one representative experiment.

ECIS core technology, which is based on a technique of measuring the change in impedance of a small electrode to AC current flow, was used. Cells are attached and spread into an 8 individual wells (with 10 identical electrodes in each well), and then the current flows in the spaces under and between the cells, as the cell membrane are normal insulators. The base of the device has an array of gold film electrodes that connect to the ECIS electronics to each of the 8 wells. Firstly, pre-treatment was performed as a baseline for 2 hours prior to treatment to ensure that the drop in impedance induced by the change of media was recoverable. Elastase was then added, this resulting in an initial surge in mechanical impedance above control levels followed by time-dependent decrease at a rate faster than control and JB1a treated-elastase injured cells. Both effects were blocked by the JB1a monoclonal antibody (FIG. 12). These observations demonstrates that betas allosteric modulation induced repair in lung injury as a result of inhibiting membrane disruption due to clustering of cell surface receptors and/or altered membrane composition (due to increase ceramide) rendering it biophysically rigid.

Summary

The results of this example confirm that beta integrin is an effective target for tissue repair and regeneration in emphysema. The results show that allosteric modulation of beta1 integrin using a single dose of monoclonal antibody, induced functional and structural reversal of elastase-induced lung injury in vivo, and found that similar matrix remodelling changes occurred in human lung tissue. The results further identified inhibition of elastase-induced caspase activation, F-actin aggregate formation and changes in cellular ATP levels. This was accompanied by maintenance of beta1 integrin levels and inhibition of caveolin-1 phosphorylation. We propose that allosteric modulation of beta1 integrin-mediated mechanosensing prevents cell death associated with lung injury and progressive emphysema, thus allowing cells to survive and for repair and regeneration to ensue.

Example 2

Functional Modulation of Beta1 Integrin via the Hybrid Domain Reverses Articular Cartilage Injury and Functional Impairment in a Mouse Model of Arthritis Rheumatoid arthritis (RA) affects 0.8-1% of the population in developed countries. It is characterised by synovial proliferation and infiltration of inflammatory cells. This occurs in conjunction with angiogenesis leading to the formation of inflammatory pannus which contributes to bone erosion and cartilage thinning. The pathogenesis of RA has not been clearly defined. However, studies suggest that CD4+ T cell-mediated autoimmune responses play a critical role in the pathogenesis of RA. In addition, interferon gamma producing Th1 cells are though to be pivotal in the development of autoimmune arthritis in both humans and animal models.

Current disease-modifying anti-rheumatic drug therapies have been shown to slow joint destruction in only a subpopulation of patients. Novel approaches have focused on specific modulation of the inflammatory response by targeting cytokines and their receptors. More recently, PI3Kγ inhibitors have been reported to suppress joint inflammation and damage in a mouse model of RA. To date there has been no treatment targeting chondrocytes.

Articular cartilage is avascular tissue and is devoid of nerves and lymphatics. Cartilage extracellular matrix (ECM) homeostasis is dependent upon the interaction between chondrocytes and their surrounding ECM via cell surface adhesion receptors such as integrins. Normal chondrocytes express integrins $\alpha_1\beta_1$, $\alpha_5\beta_1$, $\alpha_v\beta_5$, $\alpha_v\beta_3$, and $\alpha_3\beta_1$. In-vitro studies have demonstrated the importance of the interaction of β1 integrin with ECM during mesenchymal condensation and chondrocytes differentiation. The administration of anti beta1 integrin antibodies to mouse limb mesenchymal buds has been previously shown to inhibit the formation of cartilage nodules. Furthermore, beta1 integrin inhibition in cartilage explants and also specific deletion of the beta1 integrin gene in mice in-vivo has been shown to cause a reduction in growth and collagen X deposition, accompanied by abnormal chondrocytes size, disorganised actin and increased apoptosis.

Without being bound by theory, the inventors hypothesise that in injury, beta integrin activation may occur as a result of fragmentation of the ECM. This might lead to cytoskeletal abnormalities, mitochondrial changes, altered ATP homeostasis and increased susceptibility to apoptosis. Failure of removal of apoptotic debris could act as a proinflammatory stimulus. In this setting integrin disengagement could be of therapeutic value.

Materials and Methods

Induction of Arthritis In-vivo

Animals were injected with either Freund's Complete Adjuvant (FCA, 100 µg in 20 µl) from *Mycobacterium tuberculosis* in paraffin oil (Sigma) or vehicle (heavy liquid paraffin oil; controls). Briefly, injections were carried out by transiently anaesthetising the animal (3% halothane in oxygen), a small incision was made over the stifle joint to allow visual identification of the patella tendon then using a 30-gauge needle mounted on a 50-µl Hamilton syringe, FCA, vehicle or JB1a (20 µl) was injected under the patella tendon and directly into the synovial space of the stifle joint. The animals were treated with JB1a (mouse anti-human IgG1, Chemicon), isotype control (IgG1, MOPC21, Sigma) or vehicle twice at weekly intervals starting at day 7 post FCA or injection (days 7 and 14). Sham animals were also included.

Assessment of Arthritis

Animals were weighed, the diameter across the joint (left and right), just below the level of the patella, was measured weekly according to previously described method. Measurements were taken once a week prior to the injection on that day. Subjective measures were used to correlate an increased hyperalgesia score with an applied pressure to the joint induced by the injection of FCA and its reversal by JB1a. The scale was 0 (normal, high pressure applied) to 3 (very hyperalgesic, very low pressure applied). Testing involved squeezing the joint between thumb and forefinger and determining the amount of pressure required for the animal to withdraw the limb (normal end-point) or vocalise (rare).

Histopathology

Animals were killed ($CO_2$) on day 21 and the left (injected, ipsilateral) and right (control, contralateral) stifle joints surgically removed for histology. Tissues were fixed for 48 hours in 10% neutral buffered formalin then decalcified using 15% EDTA (pH 7) in 10% neutral buffered formalin for 2 weeks. Samples were embedded in paraffin wax then cut (8 µm sections) and stained haematoxylin/eosin and alcian blue (pH 1.0)/brilliant red. Images from the haematoxylin/eosin and alcian blue stained sections were digitised using Image-Pro plus (version 5.1) and micropublisher 3.3 RTV camera connected to a Zeiss axioskope with 5× objective (haematoxylin/eosin) and 20× objective (Alcian blue). The severity of the synovial inflammation, joint damage, metachromasia and pannus tissue formation were arbitrarily and subjectively scored on an analogue scale (0=no abnormality detected; 1=very slight to maximum; and 3=very marked), as previously described.

Apoptosis Measurement

Terminal Deoxyribonucleotidyl Transferase (TdT)-Mediated dUTP Nick End Labelling (TUNEL) was assessed in sections using the Red ApopTag™ Kit (Chemicon). Data for the quantification of positively stained apoptotic nuclei was acquired using the x40 oil objective of a Zeiss 510 Axiovert confocal microscope system (Carl Zeiss Ltd, Welwyn Gardens City, Herts, UK). Images of cartilage mainly tissue were constructed. The images were then converted to 8-bits grey scale and ImageJ (NIH) was used to count total number of cells. TUNEL positive cells were counted manually.

Human Articular Chondrocytes In-vitro

Primary normal adult human chondrocytes derived from the knee joint were cultured according to supplier's instructions. Cells were cultured for 2 weeks in 1.2% alginic acid (Keltone LV) in normal saline (3 weeks for bead experiments) polymerised using 102 mM $CaCl_2$. Cells were dispersed on the day of experiment from the alginate using 55 mM sodium citrate and allowed to attach onto plastic for 6 hours before being starved with DMEM/F12 media containing 0.1% FCS for 1 hour. IL-1β (carrier-free, R&D) was added at 10 ng/ml alone or in combination with JB1a (1 µg/ml) and the anti-beta1 integrin antibody, 6S6 (1 µg/ml). At the end of the 3, 6, 12 or 24 hour period, the media was aspirated and preserved and caspase 3 activity assayed using Caspase-Glo™ 3/7 (Promega) according to the manufacturers' instructions.

In a separate set of experiments chondrocytes were dispersed and seeded onto 96 multi-well plates as described above. The cells were starved in media containing 0.1% FCS then in DMEM-glucose-free with 0.1% FCS before treating with (i) IL-1β (10 ng/ml) alone, (ii) IL-1β at 10 ng/ml and JB1a (1 µg/ml) (iii) JB1a (1 µg/ml) alone or (iv) control. At the third hour, ATP levels were measured minute-by-minute using a bioluminescent ATP kit (Perkin Elmer).

Data Analysis and Statistics

Data were collected and analysed using Microsoft Excel, GraphPad Prism and SPSS. One way and multi-way ANOVA followed by unpaired t-tests were used to analyse differences between the means of normally distributed groups. When the sample size for each group was too small or the data was not normally distributed then the non-parametric Mann-Whitney U-test was used. Where significance was not achieved in two-way ANOVA for the effect of time, data were pooled for a given treatment from across all time points. For repeated measure values, a repeated measure ANOVA was used followed by post-hoc test. The medians of two or more groups of non-parametric data were analysed with a Kruskal-Wallis test, and post-hoc analysis was done using Dunn's multiple comparison. A P-value of less than 0.05 was considered significant, and where possible, the actual P-value was quoted to show proximity to the 0.05 limit. All values are presented as means or scatter.

Experimental Protocol and Results

Preliminary work performed by the inventors demonstrated the ability of specific inhibitory anti-beta1 integrin antibodies to induce an increase in ECM proteoglycans in human chondrocytes (data not shown).

To evaluate whether the modulation of beta1 integrin function facilitated repair, a modified unilateral model of arthritis in mice induced by intra-articular administration of Freund's complete adjuvant (FCA, 100 ug) was studied (Gauldie, S. D., et al. *J. Neurosci. Methods* 139, 281-291 (2004)). This model resembles chronic rheumatoid arthritis but does not cause marked significant systemic effects or mobility and body weight changes.

Mice injected with FCA showed a significant increase in their ipsilateral joint diameter and hyperalgesia score on days 7, 14 and 21 compared to either vehicle-treated or sham animals (FIG. 12(*a*)). In mice injected with FCA followed by intra-articular injection of 60 mg of JB1a on days 7 and 14, the increase in the ipsilateral joint diameter and hyperalgesia score was abolished on days 14 and 21. The contralateral joint diameter and the hyperalgesia scores showed no significant change (FIG. 12(*b*),(*c*)).

Histologically, mice injected with FCA showed joint inflammation with cellular infiltrate, synovial proliferation, pannus formation and cartilage erosion (FIG. 12(*d*),(*e*),(*f*)). The JB1a treated group showed a significant amelioration in histological markers of damage; with a marked reduction in synovial thickness and cellular infiltrate. This was accompanied by the reversal of cartilage thinning and reduced pannus formation. No adverse effects were seen after the treatment with JB1a. This indicates that the reduction in hyperalgesia scores is not simply the result of previously described blockade of neuropathic pain by functional inhibition of beta1 integrin.

The prevalence of TUNEL positive cells in mouse joints following injury and treatment was then investigated. The experiments were performed in order to ascertain whether chondrocyte apoptosis and failure of removal of apoptotic bodies by phagocytosis may itself provoke further inflammation and autoimmunity. The results showed that background prevalence of apoptosis was low, and there was a significant increase in TUNEL positive cells in the ipsilateral joints: this was significantly reduced by treatment with JB1a monoclonal antibody (FIG. 12(*g*)).

To investigate the role of beta1 integrin in chondrocyte injury, primary human chondrocytes derived from the knee joint were cultured in 1.2% alginic acid for 2 weeks, then dispersed and allowed to attach to plastic before study.

Figure 13:
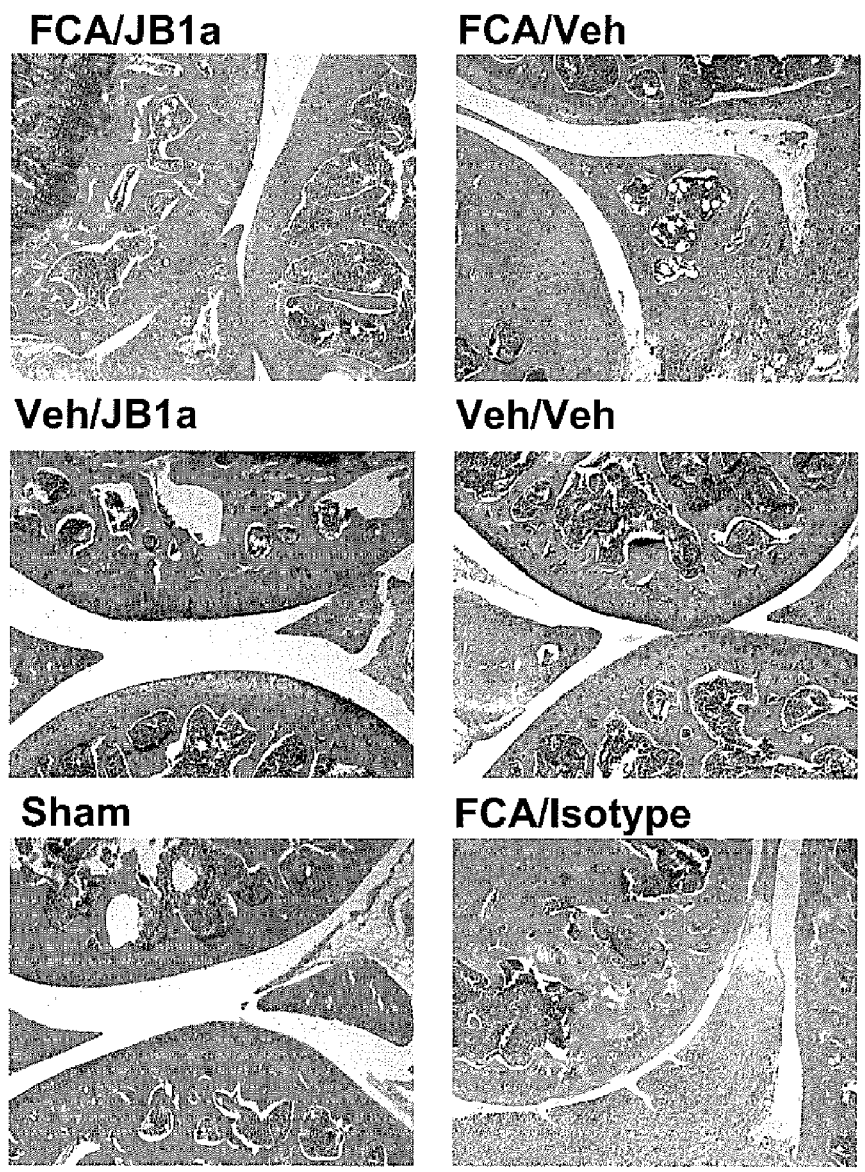
FIG. 13 shows the effects of Freund's complete adjuvant (FCA) on the function and structure of joints in mice and its reversal by JB1a treatment.

FIG. 13(*a*) demonstrates that IL-1 beta (10 ng/ml) causes a significant increase in caspase 3/7 activity. Treatment with the anti-beta1 integrin antibody (1.5 µg/ml), JB1a, a monoclonal antibody with binding specificity to an epitope present in the hybrid domain, alone had no effect on caspase 3/7 activity ((JB1A mouse anti-CD29 (Integrin beta-1 subunit) IgG monoclonal antibody, unconjugated, clone JB1a, Millipore, Catalogue number MAB-1965)). However, when IL-1beta was added with JB1a, caspase 3/7 activation was abolished.

Similar responses were obtained in experiments conducted using primary human chondrocytes cultured in alginic acid beads for 3 weeks (data not shown). The anti-beta1 integrin antibody 6S6 (1 µg/ml) which is also an adhesion blocking antibody, caused activation of caspase 3/7 activity. The epitope for this antibody is discontinuous but has not been mapped. In addition to blocking adhesion, it has been described to induce homotypic aggregation.

A further antibody, JBS5 directed against $\alpha_5\beta_1$ (alpha5beta1) integrin also causes clustering and induces inflammation 17. We found that IL-1β (iL-1beta) stimulated the secretion of IL-8 in a time-dependent manner (FIG. 13(b)). This response was reduced by 50% in the presence of JB1a. Interestingly, although the 6S6 clone had no effect on its own, when added with IL-1beta, it amplified the IL-1beta induced IL-8 secretion at both 3 and 6 hours.

Changes in ATP affect both cytoskeletal dynamics particularly actin polymerisation. ATP and actin have also been described to affect mitochondrial membrane potential and cell survival. It was demonstrated that the addition of IL-1beta (10 ng/ml) to chondrocytes in vitro, reduced ATP concentration in extended time-course studies and abrogated its sinusoidal oscillation at earlier time points (FIG. 13(c)). When IL-1beta was added with JB1a, the oscillation of ATP levels was restored although the mean concentration was reduced. The significance of this is unknown.

The present example used the JB1a monoclonal antibody which is thought to bind to beta1 integrin at an epitope defined by the amino acid sequence 82-87 of the hybrid domain. The epitope is non-conformation dependent. Although this clone is defined as an adhesion blocking antibody, the nature of the functional modification remains obscure. This definition does not take into account the multiple states of integrins, their multifunctional domains and splice variants. From our studies modulation of function via differing epitopes entailed a different outcome. The therapeutic effect was achieved via modulation of the hybrid domain.

JB1a epitope convey an allosteric modulation of beta1 integrin which stabilises the receptor in the physiological low affinity state of the receptor by preventing the swing out of the domain. Although the resulting conformation maintains extracellular matrix binding, both the association and dissociation constants are partially affected raising the possibility that JB1a is a partial antagonist.

This experiment shows that in articular chondrocytes, beta1 integrin has a pivotal role in energy homeostasis and cell survival. Without wishing to be bound by theory, the inventors hypothesise that upon local injury, degradation of the extracellular matrix results in "aggregation" of cell surface receptors; one of which is beta1 integrin. Macro- or micro-aggregation could initiate an outside-inside signalling and cytoskeletal engagement. This in turn alters the cellular mechanical properties by increasing F-actin formation, decreasing ATP recycling, and cell surface tethering forces; all of which are known to contribute to mitochondrial and cellular damage. Taken together with the accompanying findings in emphysema, this provides new and unexpected insights into the principles of cellular injury and disease progression, leading to the identification of novel targets for therapeutics.

Summary

The results of Example 2 illustrate that direct modulation of beta1 integrin using the monoclonal antibody JB1a causes functional and structural amelioration of adjuvant-induced arthritis in vivo. It was further shown that such changes are associated with a reduction in chondrocyte apoptosis and restitution of normal cellular ATP fluctuation.

Example 3

Functional Modulation of Beta1 Integrin Inhibits Beta Amyloid Fibril-induced Cell Death The main pathological hallmarks of Alzheimer's disease are the formation of extracellular amyloid plaques, intracellular neurofibrillary tangles, and neurodegeneration. Amyloid plaques are mainly composed of tangles of beta amyloid peptide which is believed to play a causal role in Alzheimer's disease.

It has been demonstrated that amyloid beta deposition and neurotoxicity in human cortical primary neurons is mediated through alpha2beta1 and alphaVbeta1 integrins. It was further claimed that blocking beta1 integrin inhibits amyloid fibril formation via functional inhibition of adhesion via beta1 integrin. Although the beta 1 integrin binding epitope of the JB1a monoclonal antibody maps to the hybrid region of beta 1 integrin, there is a possibility that it may recognise another sequence in the A domain almost sandwiched between the MIDAS and the ADMIDAS (FIG. 17). Whether the real epitope could be discontinuous and/or combinatorial, remains unclear. Indeed the hybrid domain has been implicated in allosteric alteration and targeting residues within this region induced a low affinity physiological conformation.

Figure 15:
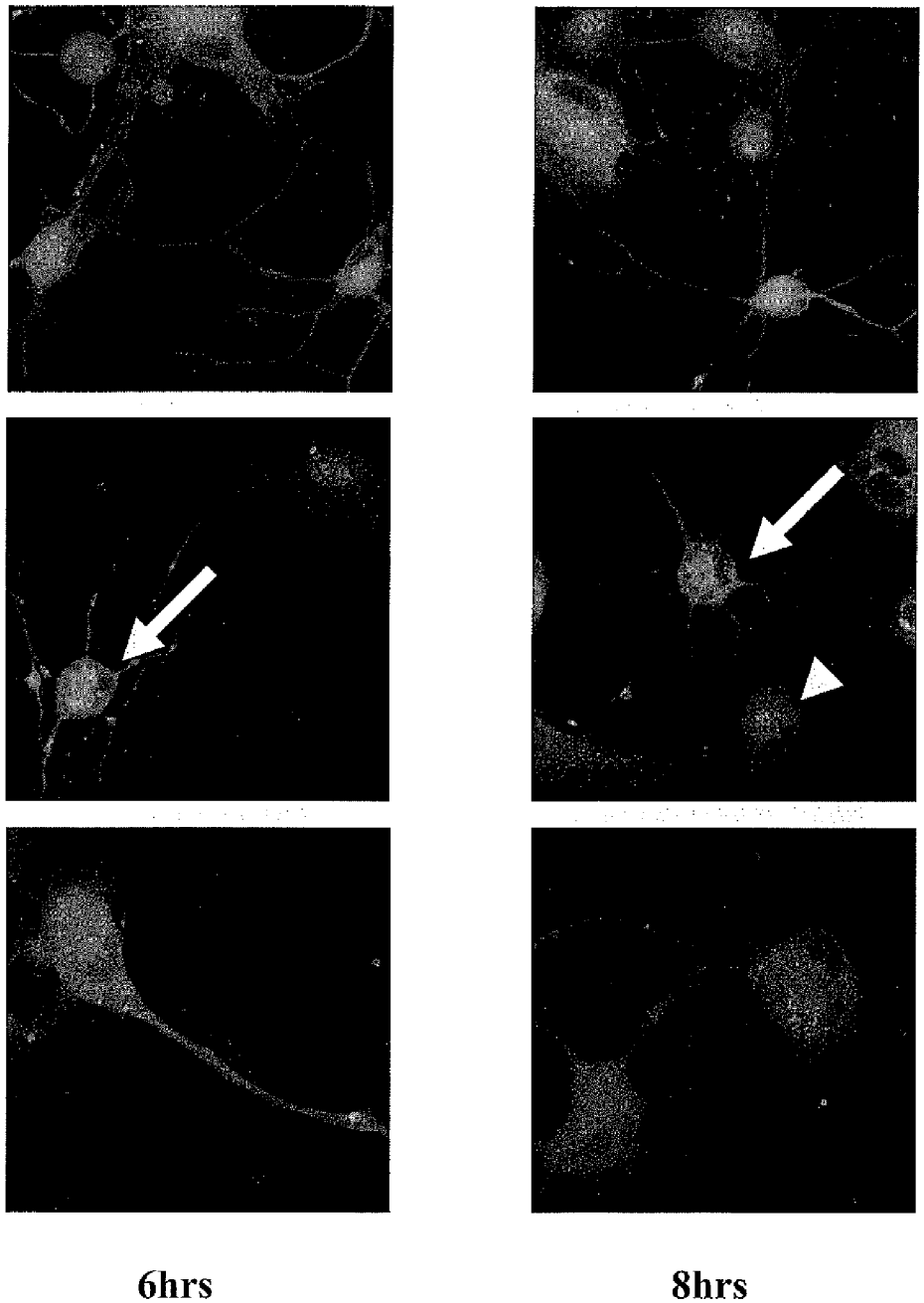
Figure 15:
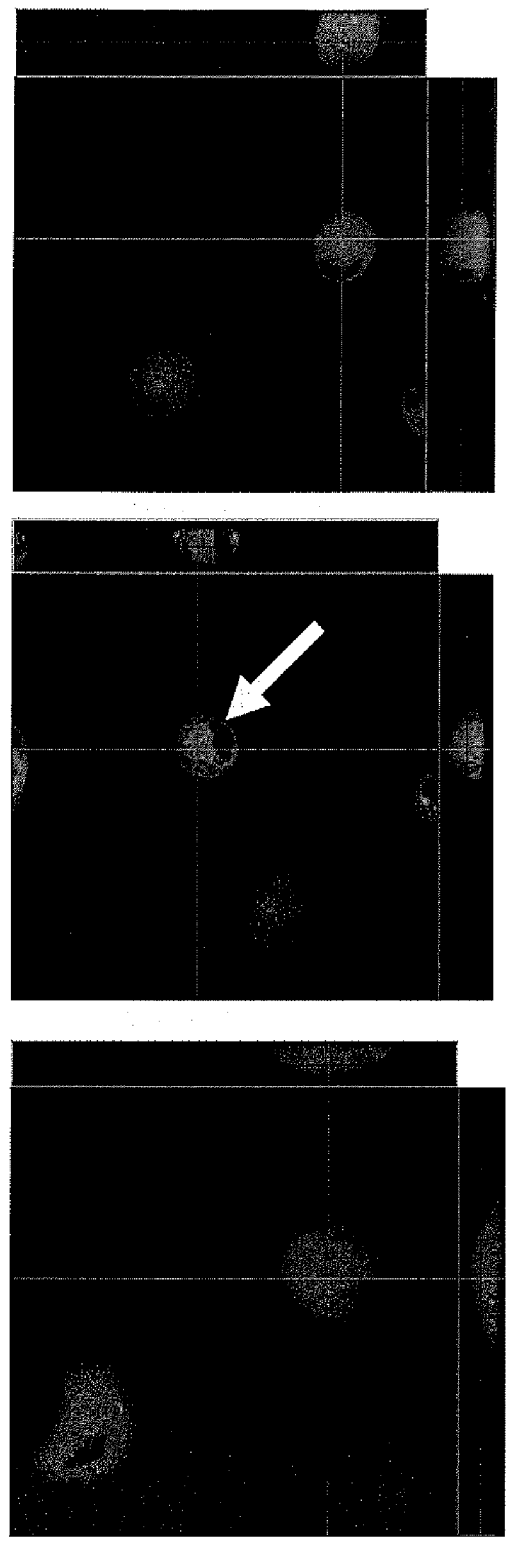

In cultured primary human cortical neurons, 1-42 beta amyloid induced caspase 3/7 activation and an increase in GM1 staining indicative of raft formation (FIG. 15). Allosteric modulation of beta1 integrin using the JB1a monoclonal antibody ((JB1A mouse anti-CD29 (Integrin beta-1 subunit) IgG monoclonal antibody, unconjugated, clone JB1a, Millipore, Catalogue number MAB-1965) conferred protection against beta amyloid-induced apoptosis. This study further indicated that there was a marked morphological change in the presence of JB1a.

Experimental Methods

Primary human cortical neuron cultures: The HCN2 cell line was obtained from the American Type Culture Collection (ATCC). HCN2 cells were cultured in Dulbecco's modified Eagle's medium containing 10% fetal bovine serum. The cells were maintained at 37° C. in 5% $CO_2$.

For differentiation experiments, cells were cultured on collagen-coated glass coverslips. Differentiation of these neuronal cells was induced by adding fresh medium containing 25 ng/ml beta-nerve growth factor (NGF), 20 nM phorbol-12-myristate-13-acetate (PMA) and 0.5 mM 3-isobutyl-1-methylxanthine (IBMX). When the neurons differentiated and developed neurotic processes, the effect of amyloid was examined as detailed below.

Three-dimensional Time-Lapse Confocal Microscopy

The media was removed and Alexa-Fluor 647 labelled G-actin (30 μg/coverslip) from rabbit was loaded using Influx (Molecular Probes). The cells were loaded with PhiPhiLux-G2D2 for visualisation of caspase activation (1/50 dilution, Oncolmmune) and FL-ganglioside 1 (1/100 dilution) GM1, Molecular probes) to visualise the plasma membrane rafts. The cells were treated with vehicle, 10 uM amyloid-beta fibrils (1-42) (American Peptide Co., Sunnyvale, Calif.), or amyloid fibrils and JB1a (2 ug/ml). Images were collected every 30 through 4 separate channels (emissions: GM1: λ=488, caspase λ=568, actin: λ=647 and brightfield) using x63 water lens and Zeiss LSM510 CLSM microscope. The resulting images were analysed with Imaris software (Bitplane AG, Switzerland). Three-dimensional images were reconstructed.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention. Reference to any prior art in this specification is not, and should not be taken as, an acknowledgment or any form of suggestion that this prior art forms part of the common general knowledge in any country.

What is claimed is:

1. An assay for identifying compounds modulating beta 1 integrin into an intermediate affinity state conformation, said assay comprising the steps of:
   providing a candidate compound that has binding specificity for beta 1 integrin,
   bringing the candidate compound into contact with beta 1 integrin, and
   determining the presence of modulation of beta 1 integrin into an intermediate affinity state conformation by the candidate compound by monitoring for:
   (i) suppression of F-actin aggregate formation and a decrease in cytoskeletal tension;
   (ii) improved cellular energy homeostasis; and
   (iii) maintenance of beta 1 integrin expression levels,
   wherein the presence of modulation of the beta 1 integrin into the intermediate affinity state conformation is characterized by:
   (1) suppression of F-actin aggregate formation and a decrease in cytoskeletal tension;
   (2) improved cellular energy homeostasis resulting from a reversion to sinusoidal oscillation of ATP levels and associated improved levels of ATP recycling within a cell; and
   (3) maintenance of beta 1 integrin expression levels,
   and further wherein the presence of said candidate compound characteristic is indicative of modulation of beta 1 integrin into the intermediate affinity state.

2. The method of claim 1, wherein the intermediate affinity state conformation of beta 1 integrin is characterised in that the extracellular headpiece of beta 1 integrin is neither bent such that the headpiece is at a distance of around 5 nm from the membrane of the cell on which the beta 1 integrin is provided, nor in an open extended conformation wherein the headpiece projects at a distance of greater than 25 nm from the membrane of the cell on which the beta 1 integrin is provided.

3. The method of claim 1, wherein the candidate compound binds to an epitope on beta 1 integrin comprising amino acid residues 82 and 87 of the mature amino acid sequence of human beta 1 integrin as defined in SEQ ID NO:1.

4. The method of claim 1, wherein the candidate compound binds to the extracellular domain of human beta 1 integrin.

5. The method of claim 1, wherein the candidate compound binds to an epitope on beta 1 integrin within amino acid residues 82 to 87 of human beta 1 integrin as defined in SEQ ID NO:1.

6. The method of claim 1, wherein the candidate compound is selected from the group consisting of a protein, a peptidomimetic, a nucleic acid and a small molecule.

7. The method of claim 1, wherein the candidate compound is an antibody or a fragment thereof.

* * * * *

SEQUENCE LISTING

<160> NUMBER OF SEQ ID NOS: 3

<210> SEQ ID NO 1
<211> LENGTH: 798
<212> TYPE: PRT
<213> ORGANISM: Homo sapiens

<400> SEQUENCE: 1

```
Met Asn Leu Gln Pro Ile Phe Trp Ile Gly Leu Ile Ser Ser Val Cys
 1               5                  10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
             35                  40                  45

Thr Asn Ser Thr Phe Leu Gln Glu Gly Met Pro Thr Ser Ala Arg Cys
 50                  55                  60

Asp Asp Leu Glu Ala Leu Lys Lys Lys Gly Cys Pro Pro Asp Asp Ile
 65                  70                  75                  80

Glu Asn Pro Arg Gly Ser Lys Asp Ile Lys Lys Asn Lys Asn Val Thr
                 85                  90                  95

Asn Arg Ser Lys Gly Thr Ala Glu Lys Leu Lys Pro Glu Asp Ile His
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Thr Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335
```

```
Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
            355                 360                 365

Gln Leu Ile Ile Asp Ala Tyr Asn Ser Leu Ser Ser Glu Val Ile Leu
            370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
            435                 440                 445

Gly Phe Thr Glu Glu Val Glu Val Ile Leu Gln Tyr Ile Cys Glu Cys
            450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
            515                 520                 525

Gly Glu Cys Val Cys Gly Gln Cys Val Cys Arg Lys Arg Asp Asn Thr
            530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
            595                 600                 605

Gly Arg Gly Ile Cys Glu Cys Gly Val Cys Lys Cys Thr Asp Pro Lys
610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
            675                 680                 685

Ser His Cys Lys Glu Lys Asp Val Asp Asp Cys Trp Phe Tyr Phe Thr
            690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
            755                 760                 765
```

```
Glu Lys Met Asn Ala Lys Trp Asp Thr Gly Glu Asn Pro Ile Tyr Lys
    770             775                 780

Ser Ala Val Thr Thr Val Val Asn Pro Lys Tyr Glu Gly Lys
785                 790                 795

<210> SEQ ID NO 2
<211> LENGTH: 6
<212> TYPE: PRT
<213> ORGANISM: Homo sapiens

<400> SEQUENCE: 2

Thr Ala Glu Lys Leu Lys
1               5

<210> SEQ ID NO 3
<211> LENGTH: 6
<212> TYPE: PRT
<213> ORGANISM: Homo sapiens

<400> SEQUENCE: 3

Thr Pro Ala Lys Leu Arg
1               5
```